(12) United States Patent
Pullela et al.

(10) Patent No.: US 6,852,742 B2
(45) Date of Patent: Feb. 8, 2005

(54) 1,4-DIHYDROPYRIDINE AND PYRIDINE COMPOUNDS AS CALCIUM CHANNEL BLOCKERS

(75) Inventors: Phani Kumar Pullela, Bangalore (IN); Paramashivappa Rangappa, Bangalore (IN); Srinivasa Rao Alapati, Bangalore (IN); Pillarisetti V. Subbarao, Bangalore (IN); Jeffrey A. Bibbs, San Diego, CA (US)

(73) Assignee: Vittal Mallya Scientific Research Foundation, Bangalore (IN)

( * ) Notice: Subject to any disclaimer, the term of this patent is extended or adjusted under 35 U.S.C. 154(b) by 0 days.

(21) Appl. No.: 10/346,195

(22) Filed: Jan. 14, 2003

(65) Prior Publication Data

US 2004/0006110 A1 Jan. 8, 2004

Related U.S. Application Data

(60) Provisional application No. 60/350,331, filed on Jan. 18, 2002, and provisional application No. 60/363,463, filed on Mar. 11, 2002.

(51) Int. Cl.$^7$ ...................... C07D 213/02; A61K 31/44
(52) U.S. Cl. ...................... 514/354; 514/194; 514/355; 514/356; 546/273.4; 546/315; 546/321
(58) Field of Search .............................. 546/273.4, 315, 546/321; 514/194, 354, 355, 356

(56) References Cited

FOREIGN PATENT DOCUMENTS

| EP | 0 220 653 A2 | 5/1987 |
|---|---|---|
| EP | 0 493 782 A2 | 7/1992 |

OTHER PUBLICATIONS

Kumar et al, Molecular Pharmacology, vol. 61, No. 3, pp. 649–658, 2002.*
Akaike, N. et al., Low–voltage–activated calcium current in rat aorta smooth muscle cells in primary culture, J. Physiol. 416:141–160 (1989).
Bean, B. P., Nitrendipine block of cardiac calcium channels: high affinity binding to the inactivated state. Proc. Natl. Acad. Sci. USA 81:6388–6392 (1984).
Bech–Hansen, N. T. et al., Loss–of–function mutations in a calcium channel $\alpha_1$–subunit gene in Xp11.23 cause incomplete X–linked congenital stationary night blindness, Nat. Genet. 19:264–267 (1984).
Bourinet, E. et al., Splicing of alpha–1a subunit gene generates phenotypic variants of P–and Q–type calcium channels, Nat. Neurosci. 2:407–415 (1999).
Carbone, E. and H. D. Lux, A low voltage–activated, fully inactivating Ca channel in vertebrate sensory neurones, Nature 310:501–502 (1984).
Catterall, W. A., Structure and regulation of voltage–gated $Ca^{2+}$ channels, Annu. Rev. Cell. Dev. Biol. 16:521–555 (2000).

Chaung, R.S.I., et al., Inhibition of T–type voltage gated calcium channel by a new scorpion toxin, Nature Neuroscience, 1:668–674 (1998).
Clozel, J. P., et al., Discovery of main pharmacological properties of mibefradil (Ro 40–5967), the first selective T–type calcium channel blocker, Journal of Hypertension 15:S17–S25 (1997).
Dubel, S. J. et al., Molecular cloning of the alpha–1 subunit of an omega–conotoxin–sensitive calcium channel, Proc. Natl. Acad. Sci. USA. 89:5058–5062 (1992).
Dunlap, K. et al., Exocytototic $Ca^{2+}$ channels in mammalian central neurons, Trends. Neurosci. 18:89–98 (1995).
Fingl et al. in, The Pharmacological Basis of Therapeutics, Ch. 1 p. 1 (1975).
Goldmann, S. and J. Stoltefuss, 1,4–Dihydropyridines: effects of chirality and conformation on the calcium antagonist and calcium agonist activities, Angewandte Chemie International Edition (English) 30:1559–1578 (1991).
Janis, R. A. and Triggle, D. J., Drugs acting on calcium channels, in Calcium Channels: Their Properties, Functions, Regulation and Clinical Relevance, ch. 13, pp. 195–249 (1990).
Janis, R.A., and D. J. Triggle, New developments in $Ca^{2+}$ channel antagonists, Journal of Medicinal Chemistry, 26:775–785 (1983).
Klugbauer, N. et al., Molecular diversity of the calcium channel alpha 2 delta subunit, J. Neurosci. 19:684–691 (1999).
Klugbauer, N. et al., A family of gama–like calcium channel subunits, FEBS Lett. 470:189–197 (2000).
Kumar, P.P. et al., Synthesis and Evaluation of a New Class of Nifedipine Analogs with T–Type Calcium Channel Blocking Activity, Molecular Pharmacology 61–6:649–657 (2002).
Lacinova, L. et al., Regulation of the calcium channel alpha 1G subunit by divalent cations and organic blockers, Neuropharmacology 39:1254–1266 (2000).
Lacinova, L. et al., Low voltage activated calcium channels: from genes to function, Gen. Physiol. Biophys. 19:121–136, Review (2000).
Loev, B., et al., "Hantzsch–type" dihydropyridine hypotensive agents, Journal of Medicinal Chemistry 17:956–965 (1974).

(List continued on next page.)

Primary Examiner—Zinna Northington Davis
(74) Attorney, Agent, or Firm—Knobbe Martens Olson & Bear LLP

(57) ABSTRACT

The present invention is directed in part towards methods of modulating the function of calcium channels with pyridine- or 1,4-dihydropyridine-based compounds. In addition, the invention describes methods of preventing and treating protein kinase-related abnormal conditions in organisms with a compound identified by the invention. Furthermore, the invention pertains to pyridine- or 1,4-dihydropyridine-based compounds and pharmaceutical compositions comprising these compounds.

53 Claims, No Drawings

OTHER PUBLICATIONS

McRory, J. E. et al., Molecular and functional characterization of a family of rat brain T–type channels, J. Biol. Chem. 275:3999–4011 (2001).

Mehrke, G. et al., The Ca++ channel blocker Ro 40–5967 blocks differently T–type and L–type Ca++ channels, Journal of Pharmacology and Experimental Therapeutics 271:1483–1488 (1994).

Neelands, T. R. et al., Functional expression of L–, N–, P/Q–, and R–type calcium channels in the human NT2–N cell line, J. Neurophysiol. 84(6):2933–2944 (2000).

Nilius, B. et al., A novel type of cardiac calcium channel in ventricular cells, Nature 316:443–446 (1985).

Nowycky, M. C. et al., Three types of neuronal calcium channel with different calcium agonist sensitivity, Nature 316:440–443 (1985).

Palmer, R. et al., Synthesis and x–ray crystal structure of 1,4–dihydro–2,6–dimethyl–4–(2'–isopropylphenyl)–3,5–pyridine–dicarboxylic acid dimethyl ester: a nifedipine analogue, Bioorganic & Medicinal Chemistry Letters 6–18:2173–2176 (1996).

Peterson, B. Z. and Catterall, W. A., Calcium binding in the pore of the L–type calcium channels modulates high affinity dihydropyridine binding, J. Biol. Chem. 270:18201–18204 (1995).

Peterson, B.Z. et al., Calmodulin is the $Ca^{2+}$ dependent inactivation of L–type calcium channels, Neuron 22:549–558 (1999).

Pragnell. M. et al., Calcium channel beta–subunit bindings to a conserved motif in the I–II cytoplasmic linker of the alpha 1–subunit, Nature (London) 368:67–70 (1994).

Richard, S. et al., Inhibition of T–type calcium currents by dihydropyridines in mouse embryonic dorsal root ganglion neurons, Neuroscience Letters 132:229–234 (1991).

Rovnyak, G.C. et al., Calcium entry blockers and activators: conformational and structural determinants of dihydropyrimidine calcium channel modulators, Journal of Medicinal Chemistry 38:199–129 (1995).

Soong, T. W. et al., Structure and functional expression of a member of low voltage–activated calcium channel family, Science (Washington DC) 260:1133–1136 (1993).

Stea, A. et al., Voltage gated calcium channels, in Handbook of Receptors and Channels; Ligand– and Voltage–Gated Ion Channels (North RA ed.) CRC Press, Inc., Boca Raton, Florida 113–152 (1995).

Takahashi, K. et al., Kinetic properties of T–type– $Ca^{2+}$ currents in isolated rat hippocampal CA1 pyramidal neurons, J. Neurophysiol. 65:148–155 (1991).

Tottene, A. et al., Functional diversity of P–type and R–type calcium channel in a rat cerebellar neurons, J. Neurosci. 16:6353–6363 (1996).

Tsien et al., Multiple types of neuronal calcium channels and their selective modulation, TINS 11:431–438 (1988).

Tsien, R. W. et al., Molecular diversity of voltage dependent $Ca^{2+}$ channels. Trends. Pharmacol. Sci. 12:349–354 (1991).

Wheeler, D.B. et al., Roles of N–type and Q type $Ca^{2+}$ channels in supporting hippocampal synaptic transmission, Science (Washington DC) 264:107–111 (1994).

Williams, M. E. et al., Structure and functional expression of alpha1, alpha2, and beta subunits of novel human neuronal calcium channel subtype, Neuron 8:71–84 (1992).

Zamponi, G. W., Antagonist binding sites of voltage–dependent calcium channels, Drug Development Research 42:131–143 (1997).

* cited by examiner

1,4-DIHYDROPYRIDINE AND PYRIDINE COMPOUNDS AS CALCIUM CHANNEL BLOCKERS

RELATED APPLICATIONS

The present application claims priority to U.S. Provisional Application Ser. No. 60/350,331, filed Jan. 18, 2002, by P. K. Pullela, et al., and entitled "1,4-DIHYDROPYRIDINE COMPOUNDS AS CALCIUM CHANNEL BLOCKERS," and U.S. Provisional Application Ser. No. 60/363,463, filed Mar. 11, 2002, by P. K. Pullela, et al., and entitled "1,4-DIHYDROPYRIDINE COMPOUNDS AS CALCIUM CHANNEL BLOCKERS," both of which are incorporated by reference herein in their entirety, including any drawings.

BACKGROUND OF THE INVENTION

1. Field of the Invention

The present invention relates to certain 1,4-dihydropyridine and pyridine compounds that can modulate the activity of calcium channels. These compounds can also be used for the treatment of diseases, such as cardiovascular disease or neurological disorders, that are associated with calcium channels.

2. Description of the Related Art

The pharmacological function and importance of calcium antagonists or calcium channel blockers, has been well documented. See, for example, R. A. Janis and D. J. Triggle "New developments in $Ca^{2+}$ channel antagonists" Journal of Medicinal Chemistry, 26, 775–785 (1983). Among the calcium antagonists, 4-aryl-1,4-dihydropyridine-3,5-dicarboxylic diesters (DHPs) of the nifedipine type have become almost indispensable for the treatment of cardiovascular diseases. For a review on Structure Activity Relations (SAR) see, S. Goldmann and J. Stoltefuss "1,4-Dihydropyridine: Effects of chirality and conformation on the calcium antagonist and calcium agonist activities" Angewandte Chemie International Edition (English) 30, 1559–1578 (1991). It was well documented that substitution on 4-phenyl ring is very crucial for pharmacological activity. Substituents at ortho or meta position improve the activity, whereas para substitution invariably decrease the activity. It was also published that bulkiness of ortho substituent, improves the calcium antagonist activity. B. Loev, M. M. Goodman, K. M. Snader, R. Tedeschi, E. Macko, "Hantzsch-Type Dihydropyridine hypotensive Agents", Journal of Medicinal Chemistry 17, 956–965 (1974).

Voltage-gated calcium channels are large transmembrane proteins that regulate the intracellular concentration of calcium ions. They are classified into high (HVA) and low (LVA) voltage-activated channels according to the membrane potential at which they are activated. E. Carbone and H. D. Lux. "A low voltage activated, fully inactivating Ca channel in vertebrate sensory neurons" Nature, 310, 501–502, (1984): B. Nilius, P. Hess, J. B. Lansman and R. W. Tsien A novel type of cardiac calcium channel in ventricular cells. Nature, 316, 443–446. (1985).; M. C. Nowycky, A. P. Fox, R. W. Tsien. "Three types of neuronal calcium channels with different calcium agonist sensitivity" Nature 316, 440–443 (1985). LVA channels open and inactivate very fast, but deactivate about 10–100 times slower than HVA calcium channels. HVA channels require stronger membrane depolarizations to activate and can be divided further into N, P/Q,R and L-types based on their pharmacological properties. LVA channels can be detected in various tissues such as heart, brain, dorsal root ganglia and adrenal gland. The use of different search algorithms on mammalian expressed sequence tagged cDNAs or on similar sequences of the nematode Caenorhabditis elegans led to the identification of several genes, three of which encoded LVA calcium channels (T-type channels) and they have been named as ($\alpha_{1G}$, $\alpha_{1H}$, $\alpha_{1I}$; see Review, L. Lacinova, N. Klugbauer, F. Hofmann "Low voltage activated calcium channels: from genes to function" Gen. Physiol. Biophys., 19, 121–136, (2000). Of the above stated types of calcium channels, L-type channels received wide attention. Among the L-type channel blockers, Dihydropyridines (DHP) is the most widely studied. But, most of the DHPs are not selective against T-type channels and DHPs inhibiting the T-type channels is still sparse.

Voltage-gated calcium channels are important regulators of calcium influx in a number of cell types. Calcium entry through these channels activates a plethora of intracellular events, from the broad stimulation of gene expression, calcium-dependent second messenger cascades, and cell proliferation, to the specific release of neurotransmitter within the nervous system, and contraction in smooth and cardiac muscle (Tsien et al., 1988)(Wheeler et al., 1994); (Dunlap et al., 1995); (Tsien et al., 1991). A number of different types of calcium channels have been identified in native tissues and divided based on their biophysical profiles into low voltage activated (LVA) and high voltage activated (HVA) channels (Nowycky et al., 1985); (Tsien et al., 1991). LVA channels first activate at relatively hyperpolarized potentials and rapidly inactivate (Akaike et al., 1989); (Takahashi et al., 1991). By contrast, HVA channels require stronger membrane depolarizations to activate and can be divided further into N, P/Q-, R and L-types based on their pharmacological properties (for review, see (Stea et al., 1995); (Zamponi, 1997)). Molecular cloning has revealed that HVA channels are heteromultimers comprised of a pore forming $\alpha_1$ subunit plus ancillary $\alpha_2$-$\delta$, $\beta$ and possibly $\gamma$ subunits (Pragnell et al., 1994); (Klugbauer et al., 1999); (Klugbauer et al., 2000); for review, see (Catterall, 2000), whereas LVA channels appear to contain only the $\alpha_1$ subunit (Lacinova et al., 2000)). To date, ten different types of calcium channel $\alpha_1$ subunits have been identified and shown to encode the previously identified native calcium channel isoforms. Expression studies show that alternative splicing of $\alpha_{1A}$ generates both P- and Q-type $Ca^{2+}$ channels (Bourinet et al., 1999), $\alpha_{1B}$ encodes N-type channels (Dubel et al., 1992)) $\alpha_{1C}$, $\alpha_{1D}$ and $\alpha_{1F}$ are L-type channels (Williams et al., 1992b); (Bech-Hansen et al., 1998), $\alpha_{1G}$, $\alpha_{1H}$ and $\alpha_{1I}$ form T-type channels (i.e., McRory et al., 2001) and $\alpha_{1E}$ may encode R-type channels (Soong et al., 1993); (Tottene et al., 1996), and $\alpha_{1S}$ encodes the skeletal muscle L-type channel isoform (Tanabe et al., 1987).

Dihydropyridine (DHP) antagonists of L-type calcium channels are widely used therapeutics in the treatment of hypertension, angina, arrhythmias, congestive heart failure, cardiomyopathy, atheriosclerosis, and cerebral and peripheral vascular disorders (Janis and Triggle, 1990) CRC Press, Cleveland. DHPs having a tendency to selectively block and enhance native L-type calcium channel activity. B. P.(Bean, 1984).; B. .Z. (Peterson and Catterall, 1995). In addition to L-type channel activity, some of the DHPs are sensitive to T-type channel activity. (N. Akaike, H. Kanaide, T, Kuga, M, Nakamura, J. Sadoshima and Tomoike "Low Voltage Activated Calcium Current in rat Aorta Smooth Muscle Cells In Primary Cultur" J Physiol. 416, 141–160, (1989).

SUMMARY OF THE INVENTION

Disclosed are compounds of Formulae I and II

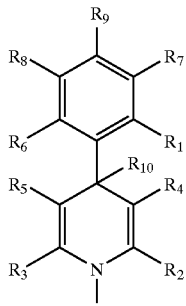
(I)

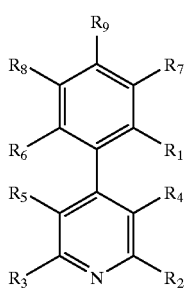
(II)

or a pharmaceutically acceptable salt, amide, ester, or prodrug thereof, where a) $R_1$ is an straight-chain, branched, or cyclic alkyl group having greater than eight carbon atoms;

b) $R_2$–$R_9$ are each independently selected from the group consisting of hydrogen, halogen, perhaloalkyl, nitro, amino, a diazo salt, optionally substituted lower alkyl, optionally substituted lower alkylene, optionally substituted lower alkoxy, optionally substituted lower alkoxyalkyl, optionally substituted lower alkoxyalkoxy, optionally substituted lower mercaptyl, optionally substituted lower mercaptoalkyl, optionally substituted lower mercaptomercaptyl, —C(O)OH, —OC(O)H, —C(O)OR, —OC(O)R, —C(S)OR, —OC(S)R, —C(O)SR, —SC(O)R, —C(S)SR, —SC(S)R, C-amido, N-amido, and optionally substituted five- or six-membered heteroaryl ring or optionally substituted six-membered aryl or heteroaryl ring, where the lower alkyl and the lower alkylene moieties are each independently and optionally substituted with one or more substituents selected from the group consisting of halogen, perhaloalkyl, nitro, amino, hydroxy, alkoxy, sulfhydryl, thioether, cyano, amido, ester, and

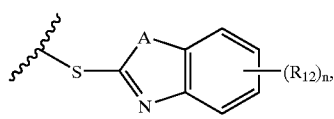

where A is selected from the group consisting of oxygen, sulfur, and —NH and $R_{12}$ is selected for the group consisting of hydrogen, hydroxy, alkoxy, haloalkoxy, halogen, haloalkyl, perhaloalkyl, nitro, amino, and a diazo salt, and n is between 0–4; and where the ring moieties are each independently and optionally substituted with one or more substituents selected from the group consisting of lower alkyl, lower alkylene, c) $R_{10}$ and $R_{11}$ in the compound of Formula I are each independently selected from the group consisting of hydrogen and lower alkyl.

Also disclosed is a method of modulating the activity of a calcium channel in a cell comprising the step of contacting the cell with a compound as described above.

In addition, disclosed is a method of treating a disease associated with a cellular calcium channel comprising identifying a subject in need of such treatment; and administering to the subject a therapeutically effective amount of a compound as described above.

Furthermore, pharmaceutical compositions are disclosed comprising a compound as described above, and a physiologically acceptable carrier, diluent, or excipient, or a combination thereof.

DETAILED DESCRIPTION OF THE PREFERRED EMBODIMENT

Here, we report a novel series of DHP derivatives (dialkyl1,4-dihydro-4-(2'-alkoxy-6'-pentadecylphenyl)-2,6-dimethyl-3,5-pyridine dicarboxylates). These compounds will exhibit activity as calcium channel antagonists, and can be used for the various purposes for which these types of compounds are known.

I. Compounds of the Invention

Thus, an aspect of the present invention relates to a compound of Formula I or Formula II

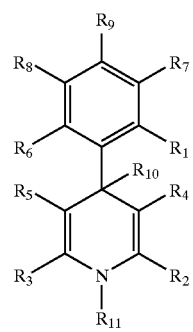
(I)

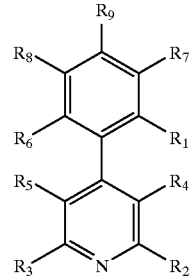
(II)

or a pharmaceutically acceptable salt, amide, ester, or prodrug thereof, where a) $R_1$ is an straight-chain, branched, or cyclic alkyl group having greater than eight carbon atoms;

b) $R_2$–$R_9$ are each independently selected from the group consisting of hydrogen, halogen, perhaloalkyl, nitro, amino, a diazo salt, optionally substituted lower alkyl, optionally substituted lower alkylene, optionally substituted lower alkoxy, optionally substituted lower alkoxyalkyl, optionally substituted lower alkoxyalkoxy, optionally substituted lower mercaptyl, optionally substituted lower mercaptoalkyl, optionally substituted lower mercaptomercaptyl, —C(O)OH, —OC(O)H, —C(O)OR, —OC(O)R, —C(S)OR, —OC(S)R, —C(O)SR, —SC(O)R, —C(S)SR, —SC(S)R, C-amido, N-amido, and optionally substituted five- or six-membered heteroaryl ring or optionally substituted six-membered aryl or heteroaryl ring,
where the lower alkyl and the lower alkylene moieties are each independently and optionally substituted with one or more substituents selected from the group consisting of halogen, perhaloalkyl, nitro, amino, hydroxy, alkoxy, sulfhydryl, thioether, cyano, amido, ester, and

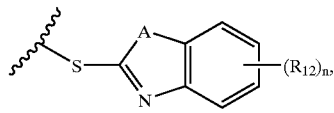

where A is selected from the group consisting of oxygen, sulfur, and —NH and $R_{12}$ is selected for the group consisting of hydrogen, hydroxy, alkoxy, haloalkoxy, halogen, haloalkyl, perhaloalkyl, nitro, amino, and a diazo salt, and n is between 0–4; and
where the ring moieties are each independently and optionally substituted with one or more substituents selected from the group consisting of lower alkyl, lower alkylene, c) $R_{10}$ and $R_{11}$ in the compound of Formula I are each independently selected from the group consisting of hydrogen and lower alkyl.

In another aspect, the invention relates to a compound of Formula I or Formula II

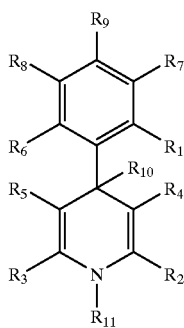

(I)

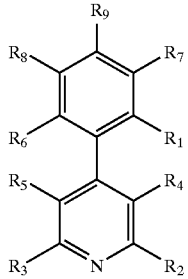

(II)

or a pharmaceutically acceptable salt, amide, ester, or prodrug thereof, where
a) $R_1$ is an straight-chain, branched, or cyclic alkyl group having greater than eight carbon atoms;
b) $R_2$–$R_9$ are each independently selected from the group consisting of hydrogen, halogen, perhaloalkyl, nitro, amino, a diazo salt, optionally substituted lower alkyl, optionally substituted lower alkylene, optionally substituted lower alkoxy, optionally substituted lower alkoxyalkyl, optionally substituted lower alkoxyalkoxy, optionally substituted lower mercaptyl, optionally substituted lower mercaptoalkyl, optionally substituted lower mercaptomercaptyl, —C(O)OH, —OC(O)H, —C(O)OR, —OC(O)R, —C(S)OR, —OC(S)R, —C(O)SR, —SC(O)R, —C(S)SR, —SC(S)R, C-amido, N-amido, and optionally substituted five- or six-membered heteroaryl ring or optionally substituted six-membered aryl or heteroaryl ring,
where the lower alkyl and the lower alkylene moieties are each independently and optionally substituted with one or more substituents selected from the group consisting of halogen, perhaloalkyl, nitro, amino, hydroxy, alkoxy, sulfhydryl, thioether, cyano, amido, ester, and

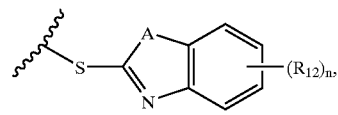

where A is selected from the group consisting of oxygen, sulfur, and —NH and $R_{12}$ is selected for the group consisting of hydrogen, hydroxy, alkoxy, haloalkoxy, halogen, haloalkyl, perhaloalkyl, nitro, amino, and a diazo salt, and n is between 0–4; and
where the ring moieties are each independently and optionally substituted with one or more substituents selected from the group consisting of lower alkyl, lower alkylene, c) $R_{10}$ and $R_{11}$ in the compound of Formula I are each independently selected from the group consisting of hydrogen and lower alkyl;

provided that:
when $R_1$ is $C_{15}H_{31}$, $R_2$ and $R_3$ are both $CH_3$, $R_4$ is $C(O)OCH(CH_3)_2$, and $R_6$ is either $OCH_3$, $OCH_2CH_3$, or $OCH(CH_3)_2$, then $R_5$ is not $C(O)OCH_3$, $C(O)OCH_2CH_3$, or $C(O)OCH(CH_3)_2$; or
when $R_1$ is $C_{15}H_{31}$, $R_2$ and $R_3$ are both $CH_3$, $R_4$ is $C(O)OCH_2CH_3$, and $R_6$ is either $OCH_3$ or $OCH_2CH_3$, then $R_5$ is not $C(O)OCH_3$ or $C(O)OCH_2CH_3$; or
when $R_1$ is $C_{15}H_{31}$, $R_2$ and $R_3$ are both $CH_3$, $R_6$ is $OCH(CH_3)_2$, and $R_4$ is either $C(O)OCH_3$ or $C(O)OCH_2CH_3$, then $R_5$ is not $C(O)OCH_3$ or $C(O)OCH_2CH_3$.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —(R)$_n$—COOR', where R and R' are optionally substituted and are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are optionally substituted and are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 40 carbon atoms (whenever it appears herein, a numerical range such as "1 to 40" refers to each integer in the given range; e.g., "1 to 40 carbon atoms" means that the alkyl group may consist of 1 carbon atom, 2 carbon atoms, 3 carbon atoms, etc., up to and including 40 carbon atoms, although the present definition also covers the occurrence of the term "alkyl" where no numerical range is designated). The alkyl group may also be a medium size alkyl having 1 to 20 carbon atoms. The alkyl group could also be a lower alkyl having 1 to 5 carbon atoms. The alkyl group of the compounds of the invention may be designated as "$C_1$–$C_4$ alkyl" or similar designations. By way of example only, "$C_1$–$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent may be substituted with one of the above substituents.

The substituent "R" or "R'" appearing by itself and without a number designation refers to an optionally substituted substituent selected from the group consisting of alkyl, cycloalkyl, aryl, heteroaryl (bonded through a ring carbon) and heteroalicyclic (bonded through a ring carbon).

An "alkoxy" group refers to a RO— group, where R is as defined herein.

An "alkoxyalkyl" group refers to a R'OR— group, where R and R' are as defined herein.

An "alkoxyalkoxy" group refers to a ROR'O— group, where R is as defined herein.

An "mercaptyl" group refers to a RS— group, where R is as defined herein.

An "mercaptoalkyl" group refers to a R'SR— group, where R and R' are as defined herein.

An "mercaptomercaptyl" group refers to a RSR'S— group, where R is as defined herein.

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonarnido" group refers to a X$_3$CS(=O)$_2$NR— group with X and R as defined herein.

An "O-carbamyl" group refers to a —OC(=O)—NR, group with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

Unless otherwise indicated, when a substituent is deemed to be "optionally substituted," it is meant that the substituent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In certain embodiments, in the compound of Formula I or II, $R_1$ is an optionally substituted alkyl group having greater than or equal to ten carbon atoms. In other embodiments, $R_1$ has greater than or equal to twelve carbon atoms, whereas in other embodiments, $R_1$ has greater than or equal to fifteen carbon atoms. In some embodiments, $R_1$ is a $C_{10}$ straight-chain alkyl group, or a $C_{11}$ straight-chain alkyl group, or a $C_{12}$ straight-chain alkyl group, or a $C_{13}$ straight-chain alkyl group, or a $C_{14}$ straight-chain alkyl group, or a $C_{15}$ straight-chain alkyl group. In certain embodiments In certain embodiments, $R_2$ and $R_3$ are each independently an optionally substituted alkyl group. In some embodiments, $R_2$ and $R_3$ are the same, whereas in other embodiments, they are different. In certain embodiments, $R_2$ and $R_3$ are lower alkyl. In certain compounds of Formula I or II, $R_2$ and $R_3$ are each independently selected from methyl, ethyl, or isopropyl. Embodiments of the present invention include those in which $R_2$ and $R_3$ are the same and they both are methyl.

In certain embodiments, $R_4$ is

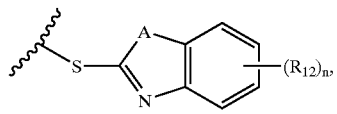

where A is selected from the group consisting of oxygen, sulfur, and —NH and $R_{12}$ is selected from the group consisting of hydrogen, hydroxy, alkoxy, haloalkoxy, halogen, haloalkyl, perhaloalkyl, nitro, amino, and a diazo salt, and n is between 0–4.

A "diazo salt" is a group of formula —NN$^+$X$^-$, where X is a halogen. In some embodiments, the halogen is a chlorine, while in other embodiments, the halogen is a fluorine, or a bromine.

In some embodiments A is oxygen, while in other embodiments A is sulfur, and in still other embodiments A is —NH.

$R_4$ and $R_5$ may be the same or different. In some embodiments, $R_4$ and $R_5$ are selected from the group consisting of a) an optionally substituted alkyl group;
b) an alkoxy of formula —(X$_1$)$_{n1}$—O—X$_2$, where
   X$_1$ is selected from the group consisting of lower alkylene, lower alkenylene, lower alkynylene, aryl, and heteroaryl;
   X$_2$ is selected from the group consisting of hydrogen, lower alkyl, aryl, and heteroaryl; and
   n1 is 0 or 1; and
c) a thioether or thiol of formula —(X$_3$)$_{n3}$—S—X$_4$, where
   X$_3$ is selected from the group consisting of lower alkylene, lower alkenylene, lower alkynylene, aryl, and heteroaryl;
   X$_4$ is selected from the group consisting of hydrogen, lower alkyl, aryl, and heteroaryl; and
   n3 is 0 or 1;
d) a carboxylic acid of formula —(X$_5$)$_{n5}$—C(=E)—E'H, where
   X$_5$ is selected from the group consisting of lower alkylene, lower alkenylene, lower alkynylene, aryl, and heteroaryl;
   E and E' are each independently selected from the group consisting of oxygen and sulfur;
   n5 is 0 or 1; and
e) an ester of formula —(X$_6$)$_{n6}$—C(=E)—E'X$_7$, or of formula —(X$_6$)$_{n6}$—E'—C(=E)—X$_7$, where
   X$_6$ is selected from the group consisting of lower alkylene, lower alkenylene, lower alkynylene, aryl, and heteroaryl;
   E and E' are each independently selected from the group consisting of oxygen and sulfur;
   X$_7$ is selected from the group consisting of hydrogen, lower alkyl, aryl, heteroaryl, hydroxy, alkoxy, amino, and —NX$_8$X$_9$,
      where X$_8$ and X$_9$ are each independently selected from the group consisting of hydrogen, alkyl, aryl, and heteroaryl; and
   n6 is 0 or 1.

In some embodiments, $R_4$ and $R_5$ are each independently lower alkyl. In certain embodiments, $R_4$ and $R_5$ are selected from the group consisting of methyl, ethyl, n-propyl, isopropyl, n-butyl, sec-butyl, and tert-butyl.

In other embodiments, where n1, n3, n5, or n6 in the above formulae is each independently 1, then X$_1$, X$_3$, X$_5$, and X$_6$ are each independently methylene (—CH$_2$—). In certain embodiments, X$_2$, X$_4$, and X$_7$ are each independently lower alkyl. The lower alkyl may be selected from the group consisting of methyl, ethyl, and isopropyl.

In certain embodiments, E and E' are each independently oxygen, whereas in other embodiments E may be sulfur and E', if it exists, oxygen.

In certain embodiments, $R_4$ and $R_5$ are each independently selected from the group consisting of —C(O)OH, —C(O)OCH$_3$, —C(O)OCH$_2$CH$_3$, —C(O)OCH(CH$_3$)$_2$, —CH$_2$OCH$_3$, —CH$_2$OCH$_2$CH$_3$, and —CH$_2$OCH(CH$_3$)$_2$.

In certain embodiments, $R_6$ is selected from the group consisting of a) hydrogen;
b) an optionally substituted alkyl group;
c) an alkoxy of formula —(X$_1$)$_{n1}$—O—X$_2$, where
   X$_1$ is selected from the group consisting of lower alkylene, lower alkenylene, lower alkynylene, aryl, and heteroaryl;
   X$_2$ is selected from the group consisting of hydrogen, lower alkyl, aryl, and heteroaryl; and
   n1 is 0 or 1; and
d) a thioether or thiol of formula —(X$_3$)$_{n3}$—S—X$_4$, where X₃ is selected from the group consisting of lower alkylene, lower alkenylene, lower alkynylene, aryl, and heteroaryl;

X₄ is selected from the group consisting of hydrogen, lower alkyl, aryl, and heteroaryl; and n3 is 0 or 1;

e) a carboxylic acid of formula —(X₅)$_{n5}$—C(=E)—E'H, where

X₅ is selected from the group consisting of lower alkylene, lower alkenylene, lower alkynylene, aryl, and heteroaryl;

E and E' are each independently selected from the group consisting of oxygen and sulfur;

n5 is 0 or 1; and f) an ester of formula —(X₆)$_{n6}$—C(=E)—E'X₇, or of formula —(X₆)$_{n6}$—E'—C(=E)—X₇, where X₆ is selected from the group consisting of lower alkylene, lower alkenylene, lower alkynylene, aryl, and heteroaryl;

E and E' are each independently selected from the group consisting of oxygen and sulfur;

X₇ is selected from the group consisting of hydrogen, lower alkyl, aryl, heteroaryl, hydroxy, alkoxy, amino, and —NX₈X₉, where X₈ and X₉ are each independently selected from the group consisting of hydrogen, alkyl, aryl, and heteroaryl; and n6 is 0 or 1.

In certain embodiments, the alkyl mentioned above is a lower alkyl. In some of these embodiments, the alkyl is selected from the group consisting of methyl, ethyl, and isopropyl. In certain other embodiments, R₆ is an alkoxy selected from the group consisting of methoxy, ethoxy, and isopropoxy.

In certain embodiments R₇–R₉ are each independently selected from the group consisting of a) hydrogen;

b) an optionally substituted alkyl group;

c) an alkoxy of formula —(X₁)$_{n1}$—O—X₂, where

X₁ is selected from the group consisting of lower alkylene, lower alkenylene, lower alkynylene, aryl, and heteroaryl;

X₂ is selected from the group consisting of hydrogen, lower alkyl, aryl, and heteroaryl; and n1 is 0 or 1; and d) a thioether or thiol of formula —(X₃)$_{n3}$—S—X₄, where X₃ is selected from the group consisting of lower alkylene, lower alkenylene, lower alkynylene, aryl, and heteroaryl;

X₄ is selected from the group consisting of hydrogen, lower alkyl, aryl, and heteroaryl; and n3 is 0 or 1;

e) a carboxylic acid of formula —(X₅)$_{n5}$—C(=E)—E'H, where

X₅ is selected from the group consisting of lower alkylene, lower alkenylene, lower alkynylene, aryl, and heteroaryl;

E and E' are each independently selected from the group consisting of oxygen and sulfur;

n5 is 0 or 1;

f) an ester of formula —(X₆)$_{n6}$—C(=E)—E'X₇, or of formula —(X₆)$_{n6}$—E'—C(=E)—X₇, where X₆ is selected from the group consisting of lower alkylene, lower alkenylene, lower alkynylene, aryl, and heteroaryl;

E and E' are each independently selected from the group consisting of oxygen and sulfur;

X₇ is selected from the group consisting of hydrogen, lower alkyl, aryl, heteroaryl, hydroxy, alkoxy, amino, and —NX₈X₉, where X₈ and X₉ are each independently selected from the group consisting of hydrogen, alkyl, aryl, and heteroaryl; and n6 is 0 or 1;

g) an amine of formula —(X₁₀)$_{n10}$—NX₁₁X₁₂, where

X₁₀ is selected from the group consisting of lower alkylene, lower alkenylene, lower alkynylene, aryl, and heteroaryl;

where X₁₀ and X₁₁ are each independently selected from the group consisting of hydrogen, alkyl, aryl, and heteroaryl; and n10 is 0 or 1;

h) NO₂;

i) halogen or perhaloalkyl; and j) CN.

In certain embodiments, the alkyl mentioned above is a lower alkyl. In some of these embodiments, the alkyl is selected from the group consisting of methyl, ethyl, and isopropyl. In certain other embodiments, R₇–R₉ are each independently hydrogen, hydroxy, cyano (CN), nitro (NO₂), amino (NH₂), methyl, ethyl, isopropyl, fluoro, and chloro. It is understood that in some embodiments R₇–R₉ are the same, whereas in other embodiments, R₇–R₉ are different.

In certain embodiments R₁₀ and R₁₁ are each independently selected from the group consisting of hydrogen and alkyl. In certain embodiments, the alkyl is a lower alkyl. In some of these embodiments, the alkyl is selected from the group consisting of methyl, ethyl, and isopropyl.

The compounds of the present invention are shown here without designating any particular stereochemistry. Some of the compounds of the present invention posses a chiral center and exhibit optical isomerism. It is understood that the scope of the present invention includes a racemic mixture of the isomer, in addition to the individual S and R isomers of the compounds disclosed herein. Separation of optical isomers from a racemic mixture can be accomplished using methods known to those of ordinary skill in the art.

In certain embodiments, the present invention relates to a compound of Formula I or II, where the compound is selected from the group consisting of diethyl 1,4-dihydro-4-(2'-ethoxy-6'-pentadecylphenyl)-2,6-dimethyl-3,5-pyridine dicarboxylate;

dimethyl 1,4-dihydro-4-(2'-ethoxy-6'-pentadecylphenyl)-2,6-dimethyl-3,5-pyridine dicarboxylate;

diisopropyl 1,4-dihydro-4-(2'-ethoxy-6'-pentadecylphenyl)-2,6-dimethyl-3,5-pyridine dicarboxylate;

diethyl 1,4-dihydro-4-(2'-methoxy-6'-pentadecylphenyl)-2,6-dimethyl-3,5-pyridine dicarboxylate;

dimethyl 1,4-dihydro-4-(2'-methoxy-6'-pentadecylphenyl)-2,6-dimethyl-3,5-pyridine dicarboxylate;

diisopropyl 1,4-dihydro-4-(2'-methoxy-6'-pentadecylphenyl)-2,6-dimethyl-3,5-carboxypyridine dicarboxylate;

diethyl 1,4-dihydro-4-(2'-isopropoxy-6'-pentadecylphenyl)-2,6-dimethyl-3,5-pyridine dicarboxylate;

dimethyl 1,4-dihydro-4-(2'-isopropoxy-6'-pentadecylphenyl)-2,6-dimethyl-3,5-pyridine dicarboxylate;

diisopropyl 1,4-dihydro-4-(2'-isopropoxy-6'-pentadecylphenyl)-2,6-dimethyl-3,5-pyridine dicarboxylate;

diethyl 1,4-dihydro-4-(2'-methoxy-6'-pentadecylphenyl)-2-methyl-6-(2'-mercapto-1'H-benzimidazolyl)methyl-3,5-pyridine dicarboxylate;

dimethyl 1,4-dihydro-4-(2'-methoxy-6'-pentadecylphenyl)-2-methyl-6-(2'-mercapto-1'H-benzimidazolyl)methyl-3,5-pyridine dicarboxylate;

diisopropyl 1,4-dihydro-4-(2'-methoxy-6'-pentadecylphenyl)-2-methyl-6-(2'-mercapto-1'H-benzimidazolyl)methyl-3,5-pyridine dicarboxylate;

diethyl 1,4-dihydro-4-(2'-isopropoxy-6'-pentadecylphenyl)-2-methyl-6-(2'-mercapto-1'H-benzimidazolyl)methyl-3,5-pyridine dicarboxylate;

dimethyl 1,4-dihydro-4-(2'-isopropoxy-6'-pentadecylphenyl)-2-methyl-6-(2'-mercapto-1'H-benzimidazolyl)methyl-3,5-pyridine dicarboxylate;

diisopropyl 1,4-dihydro-4-(2'-isopropoxy-6'-pentadecylphenyl)-2-methyl-6-(2'-mercapto-1'H-benzimidazolyl)methyl-3,5-pyridine dicarboxylate;

diethyl 1,4-dihydro-4-(2'-ethoxy-6'-pentadecylphenyl)-2-methyl-6-(2'-mercapto-1'H-benzimidazolyl)methyl-3,5-pyridine dicarboxylate;

dimethyl 1,4-dihydro-4-(2'-ethoxy-6'-pentadecylphenyl)-2-methyl-6-(2'-mercapto-1'H-benzimidazolyl)methyl-3,5-pyridine dicarboxylate;

diisopropyl 1,4-dihydro-4-(2'-ethoxy-6'-pentadecylphenyl)-2-methyl-6-(2'-mercapto-1'H-benzimidazolyl)methyl-3,5-pyridine dicarboxylate;

1,4-dihydro-4-(2'-ethoxy-6'-pentadecylphenyl)-2,6-dimethyl-3-ethyl-5-(methoxyethyl)pyridine dicarboxylate;

1,4-dihydro-4-(2'-ethoxy-6'-pentadecylphenyl)-2,6-dimethyl-3-methyl-5-(methoxyethyl)pyridine dicarboxylate;

1,4-dihydro-4-(2'-ethoxy-6'-pentadecylphenyl)-2,6-dimethyl-3-isopropyl-5-(methoxyethyl)pyridine dicarboxylate;

1,4-dihydro-4-(2'-methoxy-6'-pentadecylphenyl)-2,6-dimethyl-3-ethyl-5-(methoxyethyl)pyridine dicarboxylate;

1,4-dihydro-4-(2'-isopropoxy-6'-pentadecylphenyl)-2,6-dimethyl-3-ethyl-5-(methoxyethyl)pyridine dicarboxylate;

diethyl 1,4-dihydro-4-(2'-ethoxy-6'-pentadecylphenyl)-2-(2'-aminoethoxy)methyl-6-methyl-3,5-pyridine dicarboxylate;

dimethyl 1,4-dihydro-4-(2'-ethoxy-6'-pentadecylphenyl)-2-(2'-aminoethoxy)methyl-6-methyl-3,5-pyridine dicarboxylate;

diisopropyl 1,4-dihydro-4-(2'-ethoxy-6'-pentadecylphenyl)-2-(2'-aminoethoxy)methyl-6-methyl-3,5-pyridine dicarboxylate;

diethyl 1,4-dihydro-4-(2'-methoxy-6'-pentadecylphenyl)-2-(2'-aminoethoxy)methyl-6-methyl-3,5-pyridine dicarboxylate;

dimethyl 1,4-dihydro-4-(2'-methoxy-6'-pentadecylphenyl)-2-(2'-aminoethoxy)methyl-6-methyl-3,5-pyridine dicarboxylate;

diisopropyl 1,4-dihydro-4-(2'-methoxy-6'-pentadecylphenyl)-2-(2'-aminoethoxy)methyl-6-methyl-3,5-pyridine dicarboxylate;

diethyl 1,4-dihydro-4-(2'-isopropoxy-6'-pentadecylphenyl)-2-((2'-aminoethoxy)methyl-6-methyl-3,5-pyridine dicarboxylate;

dimethyl 1,4-dihydro-4-(2'-isopropoxy-6'-pentadecylphenyl)-2-(2'-aminoethoxy)methyl-6-methyl-3,5-pyridine dicarboxylate;

diisopropyl 1,4-dihydro-4-(2'-isopropoxy-6'-pentadecylphenyl)-2-(2'-aminoethoxy)methyl-6-methyl-3,5-pyridine dicarboxylate;

diethyl 1,4-dihydro-4-(2-ethoxy-3',5'-dinitro-6'-pentadecylphenyl)-2,6-dimethyl-3,5-pyridine dicarboxylate;

dimethyl 1,4-dihydro-4-(2'-ethoxy-3',5'-dinitro-6'-pentadecylphenyl)-2,6-dimethyl-3,5-pyridine dicarboxylate;

diisopropyl 1,4-dihydro-4-(2'-ethoxy-3',5'-dinitro-6'-pentadecylphenyl)-2,6-dimethyl-3,5-pyridine dicarboxylate;

diethyl 1,4-dihydro-4-(2'-methoxy-3',5'-dinitro-6'-pentadecylphenyl)-2,6-dimethyl-3,5-pyridine dicarboxylate;

dimethyl 1,4-dihydro-4-(2'-methoxy-3',5'-dinitro-6'-pentadecylphenyl)-2,6-dimethyl-3,5-pyridine dicarboxylate;

diisopropyl 1,4-dihydro-4-(2'-methoxy-3',5'-dinitro-6'-pentadecylphenyl)-2,6-dimethyl-3,5-pyridine dicarboxylate;

diethyl 1,4-dihydro-4-(2'-isopropoxy-3',5'-dinitro-6'-pentadecylphenyl)-2,6-dimethyl-3,5-pyridine dicarboxylate;

dimethyl 1,4-dihydro-4-(2'-isopropoxy-3',5'-dinitro-6'-pentadecylphenyl)-2,6-dimethyl-3,5-pyridine dicarboxylate;

diisopropyl 1,4-dihydro-4-(2'-isopropoxy-3',5'-dinitro-6'-pentadecylphenyl)-2,6-dimethyl-3,5-pyridine dicarboxylate;

diethyl 1,4-dihydro-4-(2'-ethoxy-3',5'-diamino-6'-pentadecylphenyl)-2,6-dimethyl-3,5-pyridine dicarboxylate;

dimethyl 1,4-dihydro-4-(2'-ethoxy-3',5'-diamino-6'-pentadecylphenyl)-2,6-dimethyl-3,5-pyridine dicarboxylate;

diisopropyl 1,4-dihydro-4-(2'-ethoxy-3',5'-diamino-6'-pentadecylphenyl)-2,6-dimethyl-3,5-pyridine dicarboxylate;

diethyl 1,4-dihydro-4-(2'-methoxy-3',5'-diamino-6'-pentadecylphenyl)-2,6-dimethyl-3,5-pyridine dicarboxylate;

dimethyl 1,4-dihydro-4-(2'-methoxy-3',5'-diamino-6'-pentadecylphenyl)-2,6-dimethyl-3,5-pyridine dicarboxylate;

diisopropyl 1,4-dihydro-4-(2'-methoxy-3',5'-diamino-6'-pentadecylphenyl)-2,6-dimethyl-3,5-pyridine dicarboxylate;

diethyl 1,4-dihydro-4-(2'-isopropoxy-3',5'-diamino-6'-pentadecylphenyl)-2,6-dimethyl-3,5-pyridine dicarboxylate;

dimethyl 1,4-dihydro-4-(2'-isopropoxy-3',5'-diamino-6'-pentadecylphenyl)-2,6-dimethyl-3,5-pyridine dicarboxylate;

diisopropyl 1,4-dihydro-4-(2'-isopropoxy-3',5'-diamino-6'-pentadecylphenyl)-2,6-dimethyl-3,5-pyridine dicarboxylate;

diethyl 1,4-dihydro-4-(2'-ethoxy-6'-pentadecylphenyl)-2-methyl-6-(5"-methyl-2-mercapto-1'H-benzimidazolyl)methyl-3,5-pyridine dicarboxylate;

dimethyl 1,4-dihydro-4-(2'-ethoxy-6'-pentadecylphenyl)-2-methyl-6-(5"-methyl-2-mercapto-1'H-benzimidazolyl)methyl-3,5-pyridine dicarboxylate;

diisopropyl 1,4-dihydro-4-(2'-ethoxy-6'-pentadecylphenyl)-2-methyl-6-(5"-methyl-2-mercapto-1'H-benzimidazolyl)methyl-3,5-pyridine dicarboxylate;

diethyl 1,4-dihydro-4-(2'-methoxy-6'-pentadecylphenyl)-2-methyl-6-(5"-methyl-2-mercapto-1'H-benzimidazolyl)methyl-3,5-pyridine dicarboxylate;

dimethyl 1,4-dihydro-4-(2'-methoxy-6'-pentadecylphenyl)-2-methyl-6-(5"-methyl-2-mercapto-1'H-benzimidazolyl)methyl-3,5-pyridine dicarboxylate;

diisopropyl 1,4-dihydro-4-(2'-methoxy-6'-pentadecylphenyl)-2-methyl-6-(5"-methyl-2-mercapto-1'H-benzimidazolyl)methyl-3,5-pyridine dicarboxylate;

diethyl 1,4-dihydro-4-(2'-isopropoxy-6'-pentadecylphenyl)-2-methyl-6-(5"-methyl-2-mercapto-1'H-benzimidazolyl)methyl-3,5-pyridine dicarboxylate;

dimethyl 1,4-dihydro-4-(2'-isopropoxy-6'-pentadecylphenyl)-2-methyl-6-methyl(5'-methyl-2-mercapto-1'H-benzimidazolyl)methyl-3,5-pyridine dicarboxylate; and diisopropyl 1,4-dihydro-4-(2'-isopropoxy-6'-pentadecylphenyl)-2-methyl-6-methyl (5'-methyl-2-mercapto-1'H-benzimidazolyl)methyl-3,5-pyridine dicarboxylate.

Some of the compounds of the present invention are listed in Table I, below, and are designated DHP-1 through DHP-655.

TABLE I

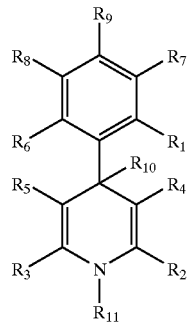 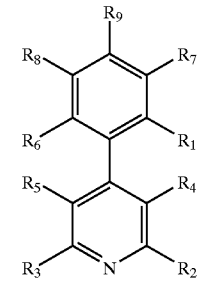

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-1  | $C_{15}H_{31}$ | $CH_3$ | $CH_3$ | $C(O)OCH_2CH_3$   | $C(O)OCH_3$       | $OCH_3$         | H | H | H |
| DHP-2  | $C_{15}H_{31}$ | $CH_3$ | $CH_3$ | $C(O)OCH_2CH_3$   | $C(O)OCH_2CH_3$   | $OCH_3$         | H | H | H |
| DHP-3  | $C_{15}H_{31}$ | $CH_3$ | $CH_3$ | $C(O)OCH_2CH_3$   | $C(O)OCH_3$       | $OCH_2CH_3$     | H | H | H |
| DHP-4  | $C_{15}H_{31}$ | $CH_3$ | $CH_3$ | $C(O)OCH_2CH_3$   | $C(O)OCH_2CH_3$   | $OCH_2CH_3$     | H | H | H |
| DHP-5  | $C_{15}H_{31}$ | $CH_3$ | $CH_3$ | $C(O)OCH_3$       | $C(O)OCH_3$       | $OCH(CH_3)_2$   | H | H | H |
| DHP-6  | $C_{15}H_{31}$ | $CH_3$ | $CH_3$ | $C(O)OCH_2CH_3$   | $C(O)OCH_3$       | $OCH(CH_3)_2$   | H | H | H |
| DHP-7  | $C_{15}H_{31}$ | $CH_3$ | $CH_3$ | $C(O)OCH_2CH_3$   | $C(O)OCH_2CH_3$   | $OCH(CH_3)_2$   | H | H | H |
| DHP-8  | $C_{15}H_{31}$ | $CH_3$ | $CH_3$ | $C(O)OCH(CH_3)_2$ | $C(O)OCH_3$       | $OCH_3$         | H | H | H |
| DHP-9  | $C_{15}H_{31}$ | $CH_3$ | $CH_3$ | $C(O)OCH(CH_3)_2$ | $C(O)OCH_2CH_3$   | $OCH_3$         | H | H | H |
| DHP-10 | $C_{15}H_{31}$ | $CH_3$ | $CH_3$ | $C(O)OCH(CH_3)_2$ | $C(O)OCH(CH_3)_2$ | $OCH_3$         | H | H | H |
| DHP-11 | $C_{15}H_{31}$ | $CH_3$ | $CH_3$ | $C(O)OCH(CH_3)_2$ | $C(O)OCH_3$       | $OCH_2CH_3$     | H | H | H |
| DHP-12 | $C_{15}H_{31}$ | $CH_3$ | $CH_3$ | $C(O)OCH(CH_3)_2$ | $C(O)OCH_2CH_3$   | $OCH_2CH_3$     | H | H | H |
| DHP-13 | $C_{15}H_{31}$ | $CH_3$ | $CH_3$ | $C(O)OCH(CH_3)_2$ | $C(O)OCH(CH_3)_2$ | $OCH_2CH_3$     | H | H | H |
| DHP-14 | $C_{15}H_{31}$ | $CH_3$ | $CH_3$ | $C(O)OCH(CH_3)_2$ | $C(O)OCH_3$       | $OCH(CH_3)_2$   | H | H | H |
| DHP-15 | $C_{15}H_{31}$ | $CH_3$ | $CH_3$ | $C(O)OCH(CH_3)_2$ | $C(O)OCH_2CH_3$   | $OCH(CH_3)_2$   | H | H | H |
| DHP-16 | $C_{15}H_{31}$ | $CH_3$ | $CH_3$ | $C(O)OCH(CH_3)_2$ | $C(O)OCH(CH_3)_2$ | $OCH(CH_3)_2$   | H | H | H |
| DHP-17 | $C_{15}H_{31}$ | $CH_3$ | $CH_3$ | $C(O)OCH_2CH_3$   | $C(O)OCH_2CH_3$   | $OCH_3$         | H | H | H |
| DHP-18 | $C_{15}H_{31}$ | $CH_3$ | $CH_3$ | $C(O)OCH_2CH_3$   | $C(O)OCH_2CH_3$   | $OCH_2CH_3$     | H | H | H |
| DHP-19 | $C_{15}H_{31}$ | $CH_3$ | $CH_3$ | $C(O)OCH_3$       | $C(O)OCH_3$       | $OCH_2CH_3$     | H | H | H |
| DHP-20 | $C_{15}H_{31}$ | $CH_3$ | $CH_3$ | $C(O)OCH_3$       | $C(O)OCH_3$       | $OCH_3$         | H | H | H |
| DHP-21 | $C_{15}H_{31}$ | $CH_3$ | A* | $C(O)OCH_2CH_3$   | $C(O)OCH_2CH_3$   | $OCH_3$         | H | H | H |
| DHP-22 | $C_{15}H_{31}$ | $CH_3$ | A  | $C(O)OCH_2CH_3$   | $C(O)OCH_3$       | $OCH_3$         | H | H | H |
| DHP-23 | $C_{15}H_{31}$ | $CH_3$ | A  | $C(O)OCH_2CH_3$   | $C(O)OCH(CH_3)_2$ | $OCH_3$         | H | H | H |
| DHP-24 | $C_{15}H_{31}$ | $CH_3$ | A  | $C(O)OCH_2CH_3$   | $C(O)OCH_2CH_3$   | $OCH(CH_3)_2$   | H | H | H |
| DHP-25 | $C_{15}H_{31}$ | $CH_3$ | A  | $C(O)OCH_2CH_3$   | $C(O)OCH_3$       | $OCH(CH_3)_2$   | H | H | H |
| DHP-26 | $C_{15}H_{31}$ | $CH_3$ | A  | $C(O)OCH_2CH_3$   | $C(O)OCH(CH_3)_2$ | $OCH(CH_3)_2$   | H | H | H |
| DHP-27 | $C_{15}H_{31}$ | $CH_3$ | A  | $C(O)OCH_2CH_3$   | $C(O)OCH_2CH_3$   | $OCH_2CH_3$     | H | H | H |
| DHP-28 | $C_{15}H_{31}$ | $CH_3$ | A  | $C(O)OCH_2CH_3$   | $C(O)OCH_3$       | $OCH_2CH_3$     | H | H | H |
| DHP-29 | $C_{15}H_{31}$ | $CH_3$ | A  | $C(O)OCH_2CH_3$   | $C(O)OCH(CH_3)_2$ | $OCH_2CH_3$     | H | H | H |
| DHP-30 | $C_{15}H_{31}$ | $CH_3$ | A  | $C(O)OCH_3$       | $C(O)OCH_3$       | $OCH_3$         | H | H | H |
| DHP-31 | $C_{15}H_{31}$ | $CH_3$ | A  | $C(O)OCH_3$       | $C(O)OCH_2CH_3$   | $OCH_3$         | H | H | H |
| DHP-32 | $C_{15}H_{31}$ | $CH_3$ | A  | $C(O)OCH_3$       | $C(O)OCH(CH_3)_2$ | $OCH_3$         | H | H | H |
| DHP-33 | $C_{15}H_{31}$ | $CH_3$ | A  | $C(O)OCH_3$       | $C(O)OCH_3$       | $OCH(CH_3)_2$   | H | H | H |
| DHP-34 | $C_{15}H_{31}$ | $CH_3$ | A  | $C(O)OCH_3$       | $C(O)OCH_2CH_3$   | $OCH(CH_3)_2$   | H | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-35 | $C_{15}H_{31}$ | $CH_3$ | A | $C(O)OCH_3$ | $C(O)OCH(CH_3)_2$ | $OCH(CH_3)_2$ | H | H | H |
| DHP-36 | $C_{15}H_{31}$ | $CH_3$ | A | $C(O)OCH_3$ | $C(O)OCH_3$ | $OCH_2CH_3$ | H | H | H |
| DHP-37 | $C_{15}H_{31}$ | $CH_3$ | A | $C(O)OCH_3$ | $C(O)OCH_2CH_3$ | $OCH_2CH_3$ | H | H | H |
| DHP-38 | $C_{15}H_{31}$ | $CH_3$ | A | $C(O)OCH_3$ | $C(O)OCH(CH_3)_2$ | $OCH_2CH_3$ | H | H | H |
| DHP-39 | $C_{15}H_{31}$ | $CH_3$ | A | $C(O)OCH(CH_3)_2$ | $C(O)OCH(CH_3)_2$ | $OCH_3$ | H | H | H |
| DHP-40 | $C_{15}H_{31}$ | $CH_3$ | A | $C(O)OCH(CH_3)_2$ | $C(O)OCH_3$ | $OCH_3$ | H | H | H |
| DHP-41 | $C_{15}H_{31}$ | $CH_3$ | A | $C(O)OCH(CH_3)_2$ | $C(O)OCH_2CH_3$ | $OCH_3$ | H | H | H |
| DHP-42 | $C_{15}H_{31}$ | $CH_3$ | A | $C(O)OCH(CH_3)_2$ | $C(O)OCH(CH_3)_2$ | $OCH(CH_3)_2$ | H | H | H |
| DHP-43 | $C_{15}H_{31}$ | $CH_3$ | A | $C(O)OCH(CH_3)_2$ | $C(O)OCH_3$ | $OCH(CH_3)_2$ | H | H | H |
| DHP-44 | $C_{15}H_{31}$ | $CH_3$ | A | $C(O)OCH(CH_3)_2$ | $C(O)OCH_2CH_3$ | $OCH(CH_3)_2$ | H | H | H |
| DHP-45 | $C_{15}H_{31}$ | $CH_3$ | A | $C(O)OCH(CH_3)_2$ | $C(O)OCH(CH_3)_2$ | $OCH_2CH_3$ | H | H | H |
| DHP-46 | $C_{15}H_{31}$ | $CH_3$ | A | $C(O)OCH(CH_3)_2$ | $C(O)OCH_3$ | $OCH_2CH_3$ | H | H | H |
| DHP-47 | $C_{15}H_{31}$ | $CH_3$ | A | $C(O)OCH(CH_3)_2$ | $C(O)OCH_2CH_3$ | $OCH_2CH_3$ | H | H | H |
| DHP-48 | $C_{15}H_{31}$ | $CH_3$ | A | $C(O)OH$ | $C(O)OH$ | $OCH_3$ | H | H | H |
| DHP-49 | $C_{15}H_{31}$ | $CH_3$ | A | $C(O)OH$ | $C(O)OCH_3$ | $OCH_3$ | H | H | H |
| DHP-50 | $C_{15}H_{31}$ | $CH_3$ | A | $C(O)OH$ | $C(O)OCH_2CH_3$ | $OCH_3$ | H | H | H |
| DHP-51 | $C_{15}H_{31}$ | $CH_3$ | A | $C(O)OH$ | $C(O)OCH(CH_3)_2$ | $OCH_3$ | H | H | H |
| DHP-52 | $C_{15}H_{31}$ | $CH_3$ | A | $C(O)OH$ | $C(O)OH$ | $OCH(CH_3)_2$ | H | H | H |
| DHP-53 | $C_{15}H_{31}$ | $CH_3$ | A | $C(O)OH$ | $C(O)OCH_3$ | $OCH(CH_3)_2$ | H | H | H |
| DHP-54 | $C_{15}H_{31}$ | $CH_3$ | A | $C(O)OH$ | $C(O)OCH_2CH_3$ | $OCH(CH_3)_2$ | H | H | H |
| DHP-55 | $C_{15}H_{31}$ | $CH_3$ | A | $C(O)OH$ | $C(O)OCH(CH_3)_2$ | $OCH(CH_3)_2$ | H | H | H |
| DHP-56 | $C_{15}H_{31}$ | $CH_3$ | A | $C(O)OH$ | $C(O)OH$ | $OCH_2CH_3$ | H | H | H |
| DHP-57 | $C_{15}H_{31}$ | $CH_3$ | A | $C(O)OH$ | $C(O)OCH_3$ | $OCH_2CH_3$ | H | H | H |
| DHP-58 | $C_{15}H_{31}$ | $CH_3$ | A | $C(O)OH$ | $C(O)OCH_2CH_3$ | $OCH_2CH_3$ | H | H | H |
| DHP-59 | $C_{15}H_{31}$ | $CH_3$ | A | $C(O)OH$ | $C(O)OCH(CH_3)_2$ | $OCH_2CH_3$ | H | H | H |
| DHP-60 | $C_{15}H_{31}$ | $CH_3$ | A | $C(O)OCH_3$ | $C(O)OH$ | $OCH_3$ | H | H | H |
| DHP-61 | $C_{15}H_{31}$ | $CH_3$ | A | $C(O)OCH_2CH_3$ | $C(O)OH$ | $OCH_3$ | H | H | H |
| DHP-62 | $C_{15}H_{31}$ | $CH_3$ | A | $C(O)OCH(CH_3)_2$ | $C(O)OH$ | $OCH_3$ | H | H | H |
| DHP-63 | $C_{15}H_{31}$ | $CH_3$ | A | $C(O)OCH_3$ | $C(O)OH$ | $OCH(CH_3)_2$ | H | H | H |
| DHP-64 | $C_{15}H_{31}$ | $CH_3$ | A | $C(O)OCH_2CH_3$ | $C(O)OH$ | $OCH(CH_3)_2$ | H | H | H |
| DHP-65 | $C_{15}H_{31}$ | $CH_3$ | A | $C(O)OCHCH_3)_2$ | $C(O)OH$ | $OCH(CH_3)_2$ | H | H | H |
| DHP-66 | $C_{15}H_{31}$ | $CH_3$ | A | $C(O)OCH_3$ | $C(O)OH$ | $OCH_2CH_3$ | H | H | H |
| DHP-67 | $C_{15}H_{31}$ | $CH_3$ | A | $C(O)OCH_2CH_3$ | $C(O)OH$ | $OCH_2CH_3$ | H | H | H |
| DHP-68 | $C_{15}H_{31}$ | $CH_3$ | A | $C(O)OCH(CH_3)_2$ | $C(O)OH$ | $OCH_2CH_3$ | H | H | H |
| DHP-69 | $C_{15}H_{31}$ | $CH_3$ | $CH_3$ | $C(O)OCH_2CH_2OCH_3$ | $C(O)OCH_2CH_3$ | $OCH_2CH_3$ | H | H | H |
| DHP-70 | $C_{15}H_{31}$ | $CH_3$ | $CH_3$ | $C(O)OCH_2CH_2OCH_3$ | $C(O)OCH_3$ | $OCH_2CH_3$ | H | H | H |
| DHP-71 | $C_{15}H_{31}$ | $CH_3$ | $CH_3$ | $C(O)OCH_2CH_2OCH_3$ | $C(O)OCH(CH_3)_2$ | $OCH_2CH_3$ | H | H | H |
| DHP-72 | $C_{15}H_{31}$ | $CH_3$ | $CH_3$ | $C(O)OCH_2CH_2OCH_3$ | $C(O)OCH_2CH_3$ | $OCH(CH_3)_2$ | H | H | H |
| DHP-73 | $C_{15}H_{31}$ | $CH_3$ | $CH_3$ | $C(O)OCH_2CH_2OCH_3$ | $C(O)OCH_3$ | $OCH(CH_3)_2$ | H | H | H |
| DHP-74 | $C_{15}H_{31}$ | $CH_3$ | $CH_3$ | $C(O)OCH_2CH_2OCH_3$ | $C(O)OCH(CH_3)_2$ | $OCH(CH_3)_2$ | H | H | H |
| DHP-75 | $C_{15}H_{31}$ | $CH_3$ | $CH_3$ | $C(O)OCH_2CH_2OCH_3$ | $C(O)OCH_2CH_3$ | $OCH_3$ | H | H | H |
| DHP-76 | $C_{15}H_{31}$ | $CH_3$ | $CH_3$ | $C(O)OCH_2CH_2OCH_3$ | $C(O)OCH_3$ | $OCH_3$ | H | H | H |
| DHP-77 | $C_{15}H_{31}$ | $CH_3$ | $CH_3$ | $C(O)OCH_2CH_2OCH_3$ | $C(O)OCH(CH_3)_2$ | $OCH_3$ | H | H | H |
| DHP-78 | $C_{15}H_{31}$ | B** | $CH_3$ | $C(O)OCH_2CH_3$ | $C(O)OCH_3$ | $OCH_3$ | H | H | H |
| DHP-79 | $C_{15}H_{31}$ | B | $CH_3$ | $C(O)OCH_2CH_3$ | $C(O)OCH_3$ | $OCH_3$ | H | H | H |
| DHP-80 | $C_{15}H_{31}$ | B | $CH_3$ | $C(O)OCH_2CH_3$ | $C(O)OCH(CH_3)_2$ | $OCH_3$ | H | H | H |
| DHP-81 | $C_{15}H_{31}$ | B | $CH_3$ | $C(O)OCH_2CH_3$ | $C(O)OCH_2CH_3$ | $OCH(CH_3)_2$ | H | H | H |
| DHP-82 | $C_{15}H_{31}$ | B | $CH_3$ | $C(O)OCH_2CH_3$ | $C(O)OCH_3$ | $OCH(CH_3)_2$ | H | H | H |
| DHP-83 | $C_{15}H_{31}$ | B | $CH_3$ | $C(O)OCH_2CH_3$ | $C(O)OCH(CH_3)_2$ | $OCH(CH_3)_2$ | H | H | H |
| DHP-84 | $C_{15}H_{31}$ | B | $CH_3$ | $C(O)OCH_2CH_3$ | $C(O)OCH_2CH_3$ | $OCH_2CH_3$ | H | H | H |
| DHP-85 | $C_{15}H_{31}$ | B | $CH_3$ | $C(O)OCH_2CH_3$ | $C(O)OCH_3$ | $OCH_2CH_3$ | H | H | H |
| DHP-86 | $C_{15}H_{31}$ | B | $CH_3$ | $C(O)OCH_2CH_3$ | $C(O)OCH(CH_3)_2$ | $OCH_2CH_3$ | H | H | H |
| DHP-87 | $C_{15}H_{31}$ | B | $CH_3$ | $C(O)OCH_3$ | $C(O)OCH_3$ | $OCH_3$ | H | H | H |
| DHP-88 | $C_{15}H_{31}$ | B | $CH_3$ | $C(O)OCH_3$ | $C(O)OCH_2CH_3$ | $OCH_3$ | H | H | H |
| DHP-89 | $C_{15}H_{31}$ | B | $CH_3$ | $C(O)OCH_3$ | $C(O)OCH(CH_3)_2$ | $OCH_3$ | H | H | H |
| DHP-90 | $C_{15}H_{31}$ | B | $CH_3$ | $C(O)OCH_3$ | $C(O)OCH_3$ | $OCH(CH_3)_2$ | H | H | H |
| DHP-91 | $C_{15}H_{31}$ | B | $CH_3$ | $C(O)OCH_3$ | $C(O)OCH_2CH_3$ | $OCH(CH_3)_2$ | H | H | H |
| DHP-92 | $C_{15}H_{31}$ | B | $CH_3$ | $C(O)OCH_3$ | $C(O)OCH(CH_3)_2$ | $OCH(CH_3)_2$ | H | H | H |
| DHP-93 | $C_{15}H_{31}$ | B | $CH_3$ | $C(O)OCH_3$ | $C(O)OCH_3$ | $OCH_2CH_3$ | H | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-94 | $C_{15}H_{31}$ | B | $CH_3$ | $C(O)OCH_3$ | $C(O)OCH_2CH_3$ | $OCH_2CH_3$ | H | H | H |
| DHP-95 | $C_{15}H_{31}$ | B | $CH_3$ | $C(O)OCH_3$ | $C(O)OCH(CH_3)_2$ | $OCH_2CH_3$ | H | H | H |
| DHP-96 | $C_{15}H_{31}$ | B | $CH_3$ | $C(O)OCH(CH_3)_2$ | $C(O)OCH(CH_3)_2$ | $OCH_3$ | H | H | H |
| DHP-97 | $C_{15}H_{31}$ | B | $CH_3$ | $C(O)OCH(CH_3)_2$ | $C(O)OCH_3$ | $OCH_3$ | H | H | H |
| DHP-98 | $C_{15}H_{31}$ | B | $CH_3$ | $C(O)OCH(CH_3)_2$ | $C(O)OCH_2CH_3$ | $OCH_3$ | H | H | H |
| DHP-99 | $C_{15}H_{31}$ | B | $CH_3$ | $C(O)OCH(CH_3)_2$ | $C(O)OCH(CH_3)_2$ | $OCH(CH_3)_2$ | H | H | H |
| DHP-100 | $C_{15}H_{31}$ | B | $CH_3$ | $C(O)OCH(CH_3)_2$ | $C(O)OCH_3$ | $OCH(CH_3)_2$ | H | H | H |
| DHP-101 | $C_{15}H_{31}$ | B | $CH_3$ | $C(O)OCH(CH_3)_2$ | $C(O)OCH_2CH_3$ | $OCH(CH_3)_2$ | H | H | H |
| DHP-102 | $C_{15}H_{31}$ | B | $CH_3$ | $C(O)OCH(CH_3)_2$ | $C(O)OCH(CH_3)_2$ | $OCH_2CH_3$ | H | H | H |
| DHP-103 | $C_{15}H_{31}$ | B | $CH_3$ | $C(O)OCH(CH_3)_2$ | $C(O)OCH_3$ | $OCH_2CH_3$ | H | H | H |
| DHP-104 | $C_{15}H_{31}$ | B | $CH_3$ | $C(O)OCH(CH_3)_2$ | $C(O)OCH_2CH_3$ | $OCH_2CH_3$ | H | H | H |
| DHP-105 | $C_{15}H_{31}$ | B | $CH_3$ | $C(O)OH$ | $C(O)OH$ | $OCH_3$ | H | H | H |
| DHP-106 | $C_{15}H_{31}$ | B | $CH_3$ | $C(O)OH$ | $C(O)OCH_3$ | $OCH_3$ | H | H | H |
| DHP-107 | $C_{15}H_{31}$ | B | $CH_3$ | $C(O)OH$ | $C(O)OCH_2CH_3$ | $OCH_3$ | H | H | H |
| DHP-108 | $C_{15}H_{31}$ | B | $CH_3$ | $C(O)OH$ | $C(O)OCH(CH_3)_2$ | $OCH_3$ | H | H | H |
| DHP-109 | $C_{15}H_{31}$ | B | $CH_3$ | $C(O)OH$ | $C(O)OH$ | $OCH(CH_3)_2$ | H | H | H |
| DHP-110 | $C_{15}H_{31}$ | B | $CH_3$ | $C(O)OH$ | $C(O)OCH_3$ | $OCH(CH_3)_2$ | H | H | H |
| DHP-111 | $C_{15}H_{31}$ | B | $CH_3$ | $C(O)OH$ | $C(O)OCH_2CH_3$ | $OCH(CH_3)_2$ | H | H | H |
| DHP-112 | $C_{15}H_{31}$ | B | $CH_3$ | $C(O)OH$ | $C(O)OCH(CH_3)_2$ | $OCH(CH_3)_2$ | H | H | H |
| DHP-113 | $C_{15}H_{31}$ | B | $CH_3$ | $C(O)OH$ | $C(O)OH$ | $OCH_2CH_3$ | H | H | H |
| DHP-114 | $C_{15}H_{31}$ | B | $CH_3$ | $C(O)OH$ | $C(O)OCH_3$ | $OCH_2CH_3$ | H | H | H |
| DHP-115 | $C_{15}H_{31}$ | B | $CH_3$ | $C(O)OH$ | $C(O)OCH_2CH_3$ | $OCH_2CH_3$ | H | H | H |
| DHP-116 | $C_{15}H_{31}$ | B | $CH_3$ | $C(O)OH$ | $C(O)OCH(CH_3)_2$ | $OCH_2CH_3$ | H | H | H |
| DHP-117 | $C_{15}H_{31}$ | B | $CH_3$ | $C(O)OCH_3$ | $C(O)OH$ | $OCH_3$ | H | H | H |
| DHP-118 | $C_{15}H_{31}$ | B | $CH_3$ | $C(O)OCH_2CH_3$ | $C(O)OH$ | $OCH_3$ | H | H | H |
| DHP-119 | $C_{15}H_{31}$ | B | $CH_3$ | $C(O)OCH(CH_3)_2$ | $C(O)OH$ | $OCH_3$ | H | H | H |
| DHP-120 | $C_{15}H_{31}$ | B | $CH_3$ | $C(O)OCH_3$ | $C(O)OH$ | $OCH(CH_3)_2$ | H | H | H |
| DHP-121 | $C_{15}H_{31}$ | B | $CH_3$ | $C(O)OCH_2CH_3$ | $C(O)OH$ | $OCH(CH_3)_2$ | H | H | H |
| DHP-122 | $C_{15}H_{31}$ | B | $CH_3$ | $C(O)OCH(CH_3)_2$ | $C(O)OH$ | $OCH(CH_3)_2$ | H | H | H |
| DHP-123 | $C_{15}H_{31}$ | B | $CH_3$ | $C(O)OCH_3$ | $C(O)OH$ | $OCH_2CH_3$ | H | H | H |
| DHP-124 | $C_{15}H_{31}$ | B | $CH_3$ | $C(O)OCH_2CH_3$ | $C(O)OH$ | $OCH_2CH_3$ | H | H | H |
| DHP-125 | $C_{15}H_{31}$ | B | $CH_3$ | $C(O)OCH(CH_3)_2$ | $C(O)OH$ | $OCH_2CH_3$ | H | H | H |
| DHP-126 | $C_{15}H_{31}$ | $CH_3$ | $CH_3$ | $C(O)OCH_2CH_3$ | $C(O)OCH_2CH_3$ | $OCH_3$ | $NO_2$ | $NO_2$ | H |
| DHP-127 | $C_{15}H_{31}$ | $CH_3$ | $CH_3$ | $C(O)OCH_2CH_3$ | $C(O)OCH_3$ | $OCH_3$ | $NO_2$ | $NO_2$ | H |
| DHP-128 | $C_{15}H_{31}$ | $CH_3$ | $CH_3$ | $C(O)OCH_2CH_3$ | $C(O)OCH(CH_3)_2$ | $OCH_3$ | $NO_2$ | $NO_2$ | H |
| DHP-129 | $C_{15}H_{31}$ | $CH_3$ | $CH_3$ | $C(O)OCH_2CH_3$ | $C(O)OCH_2CH_3$ | $OCH(CH_3)_2$ | $NO_2$ | $NO_2$ | H |
| DHP-130 | $C_{15}H_{31}$ | $CH_3$ | $CH_3$ | $C(O)OCH_2CH_3$ | $C(O)OCH_3$ | $OCH(CH_3)_2$ | $NO_2$ | $NO_2$ | H |
| DHP-131 | $C_{15}H_{31}$ | $CH_3$ | $CH_3$ | $C(O)OCH_2CH_3$ | $C(O)OCH(CH_3)_2$ | $OCH(CH_3)_2$ | $NO_2$ | $NO_2$ | H |
| DHP-132 | $C_{15}H_{31}$ | $CH_3$ | $CH_3$ | $C(O)OCH_2CH_3$ | $C(O)OCH_2CH_3$ | $OCH_2CH_3$ | $NO_2$ | $NO_2$ | H |
| DHP-133 | $C_{15}H_{31}$ | $CH_3$ | $CH_3$ | $C(O)OCH_2CH_3$ | $C(O)OCH_3$ | $OCH_2CH_3$ | $NO_2$ | $NO_2$ | H |
| DHP-134 | $C_{15}H_{31}$ | $CH_3$ | $CH_3$ | $C(O)OCH_2CH_3$ | $C(O)OCH(CH_3)_2$ | $OCH_2CH_3$ | $NO_2$ | $NO_2$ | H |
| DHP-135 | $C_{15}H_{31}$ | $CH_3$ | $CH_3$ | $C(O)OCH_3$ | $C(O)OCH_3$ | $OCH_3$ | $NO_2$ | $NO_2$ | H |
| DHP-136 | $C_{15}H_{31}$ | $CH_3$ | $CH_3$ | $C(O)OCH_3$ | $C(O)OCH_2CH_3$ | $OCH_3$ | $NO_2$ | $NO_2$ | H |
| DHP-137 | $C_{15}H_{31}$ | $CH_3$ | $CH_3$ | $C(O)OCH_3$ | $C(O)OCH(CH_3)_2$ | $OCH_3$ | $NO_2$ | $NO_2$ | H |
| DHP-138 | $C_{15}H_{31}$ | $CH_3$ | $CH_3$ | $C(O)OCH_3$ | $C(O)OCH_3$ | $OCH(CH_3)_2$ | $NO_2$ | $NO_2$ | H |
| DHP-139 | $C_{15}H_{31}$ | $CH_3$ | $CH_3$ | $C(O)OCH_3$ | $C(O)OCH_2CH_3$ | $OCH(CH_3)_2$ | $NO_2$ | $NO_2$ | H |
| DHP-140 | $C_{15}H_{31}$ | $CH_3$ | $CH_3$ | $C(O)OCH_3$ | $C(O)OCH(CH_3)_2$ | $OCH(CH_3)_2$ | $NO_2$ | $NO_2$ | H |
| DHP-141 | $C_{15}H_{31}$ | $CH_3$ | $CH_3$ | $C(O)OCH_3$ | $C(O)OCH_3$ | $OCH_2CH_3$ | $NO_2$ | $NO_2$ | H |
| DHP-142 | $C_{15}H_{31}$ | $CH_3$ | $CH_3$ | $C(O)OCH_3$ | $C(O)OCH_2CH_3$ | $OCH_2CH_3$ | $NO_2$ | $NO_2$ | H |
| DHP-143 | $C_{15}H_{31}$ | $CH_3$ | $CH_3$ | $C(O)OCH_3$ | $C(O)OCH(CH_3)_2$ | $OCH_2CH_3$ | $NO_2$ | $NO_2$ | H |
| DHP-144 | $C_{15}H_{31}$ | $CH_3$ | $CH_3$ | $C(O)OCH(CH_3)_2$ | $C(O)OCH(CH_3)_2$ | $OCH_3$ | $NO_2$ | $NO_2$ | H |
| DHP-145 | $C_{15}H_{31}$ | $CH_3$ | $CH_3$ | $C(O)OCH(CH_3)_2$ | $C(O)OCH_3$ | $OCH_3$ | $NO_2$ | $NO_2$ | H |
| DHP-146 | $C_{15}H_{31}$ | $CH_3$ | $CH_3$ | $C(O)OCH(CH_3)_2$ | $C(O)OCH_2CH_3$ | $OCH_3$ | $NO_2$ | $NO_2$ | H |
| DHP-147 | $C_{15}H_{31}$ | $CH_3$ | $CH_3$ | $C(O)OCH(CH_3)_2$ | $C(O)OCH(CH_3)_2$ | $OCH(CH_3)_2$ | $NO_2$ | $NO_2$ | H |
| DHP-148 | $C_{15}H_{31}$ | $CH_3$ | $CH_3$ | $C(O)OCH(CH_3)_2$ | $C(O)OCH_3$ | $OCH(CH_3)_2$ | $NO_2$ | $NO_2$ | H |
| DHP-149 | $C_{15}H_{31}$ | $CH_3$ | $CH_3$ | $C(O)OCH(CH_3)_2$ | $C(O)OCH_2CH_3$ | $OCH(CH_3)_2$ | $NO_2$ | $NO_2$ | H |
| DHP-150 | $C_{15}H_{31}$ | $CH_3$ | $CH_3$ | $C(O)OCH(CH_3)_2$ | $C(O)OCH(CH_3)_2$ | $OCH_2CH_3$ | $NO_2$ | $NO_2$ | H |
| DHP-151 | $C_{15}H_{31}$ | $CH_3$ | $CH_3$ | $C(O)OCH(CH_3)_2$ | $C(O)OCH_3$ | $OCH_2CH_3$ | $NO_2$ | $NO_2$ | H |
| DHP-152 | $C_{15}H_{31}$ | $CH_3$ | $CH_3$ | $C(O)OCH(CH_3)_2$ | $C(O)OCH_2CH_3$ | $OCH_2CH_3$ | $NO_2$ | $NO_2$ | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-153 | $C_{15}H_{31}$ | $CH_3$ | $CH_3$ | C(O)OH | C(O)OH | $OCH_3$ | $NO_2$ | $NO_2$ | H |
| DHP-154 | $C_{15}H_{31}$ | $CH_3$ | $CH_3$ | C(O)OH | $C(O)OCH_3$ | $OCH_3$ | $NO_2$ | $NO_2$ | H |
| DHP-155 | $C_{15}H_{31}$ | $CH_3$ | $CH_3$ | C(O)OH | $C(O)OCH_2CH_3$ | $OCH_3$ | $NO_2$ | $NO_2$ | H |
| DHP-156 | $C_{15}H_{31}$ | $CH_3$ | $CH_3$ | C(O)OH | $C(O)OCH(CH_3)_2$ | $OCH_3$ | $NO_2$ | $NO_2$ | H |
| DHP-157 | $C_{15}H_{31}$ | $CH_3$ | $CH_3$ | C(O)OH | C(O)OH | $OCH(CH_3)_2$ | $NO_2$ | $NO_2$ | H |
| DHP-158 | $C_{15}H_{31}$ | $CH_3$ | $CH_3$ | C(O)OH | $C(O)OCH_3$ | $OCH(CH_3)_2$ | $NO_2$ | $NO_2$ | H |
| DHP-159 | $C_{15}H_{31}$ | $CH_3$ | $CH_3$ | C(O)OH | $C(O)OCH_2CH_3$ | $OCH(CH_3)_2$ | $NO_2$ | $NO_2$ | H |
| DHP-160 | $C_{15}H_{31}$ | $CH_3$ | $CH_3$ | C(O)OH | $C(O)OCH(CH_3)_2$ | $OCH(CH_3)_2$ | $NO_2$ | $NO_2$ | H |
| DHP-161 | $C_{15}H_{31}$ | $CH_3$ | $CH_3$ | C(O)OH | C(O)OH | $OCH_2CH_3$ | $NO_2$ | $NO_2$ | H |
| DHP-162 | $C_{15}H_{31}$ | $CH_3$ | $CH_3$ | C(O)OH | $C(O)OCH_3$ | $OCH_2CH_3$ | $NO_2$ | $NO_2$ | H |
| DHP-163 | $C_{15}H_{31}$ | $CH_3$ | $CH_3$ | C(O)OH | $C(O)OCH_2CH_3$ | $OCH_2CH_3$ | $NO_2$ | $NO_2$ | H |
| DHP-164 | $C_{15}H_{31}$ | $CH_3$ | $CH_3$ | C(O)OH | $C(O)OCH(CH_3)_2$ | $OCH_2CH_3$ | $NO_2$ | $NO_2$ | H |
| DHP-165 | $C_{15}H_{31}$ | $CH_3$ | $CH_3$ | $C(O)OCH_3$ | C(O)OH | $OCH_3$ | $NO_2$ | $NO_2$ | H |
| DHP-166 | $C_{15}H_{31}$ | $CH_3$ | $CH_3$ | $C(O)OCH_2CH_3$ | C(O)OH | $OCH_3$ | $NO_2$ | $NO_2$ | H |
| DHP-167 | $C_{15}H_{31}$ | $CH_3$ | $CH_3$ | $C(O)OCH(CH_3)_2$ | C(O)OH | $OCH_3$ | $NO_2$ | $NO_2$ | H |
| DHP-168 | $C_{15}H_{31}$ | $CH_3$ | $CH_3$ | $C(O)OCH_3$ | C(O)OH | $OCH(CH_3)_2$ | $NO_2$ | $NO_2$ | H |
| DHP-169 | $C_{15}H_{31}$ | $CH_3$ | $CH_3$ | $C(O)OCH_2CH_3$ | C(O)OH | $OCH(CH_3)_2$ | $NO_2$ | $NO_2$ | H |
| DHP-170 | $C_{15}H_{31}$ | $CH_3$ | $CH_3$ | $C(O)OCH(CH_3)_2$ | C(O)OH | $OCH(CH_3)_2$ | $NO_2$ | $NO_2$ | H |
| DHP-171 | $C_{15}H_{31}$ | $CH_3$ | $CH_3$ | $C(O)OCH_3$ | C(O)OH | $OCH_2CH_3$ | $NO_2$ | $NO_2$ | H |
| DHP-172 | $C_{15}H_{31}$ | $CH_3$ | $CH_3$ | $C(O)OCH_2CH_3$ | C(O)OH | $OCH_2CH_3$ | $NO_2$ | $NO_2$ | H |
| DHP-173 | $C_{15}H_{31}$ | $CH_3$ | $CH_3$ | $C(O)OCH(CH_3)_2$ | C(O)OH | $OCH_2CH_3$ | $NO_2$ | $NO_2$ | H |
| DHP-174 | $C_{15}H_{31}$ | $CH_3$ | $CH_3$ | $C(O)OCH_2CH_3$ | $C(O)OCH_2CH_3$ | $OCH_3$ | $NO_2$ | H | H |
| DHP-175 | $C_{15}H_{31}$ | $CH_3$ | $CH_3$ | $C(O)OCH_2CH_3$ | $C(O)OCH_3$ | $OCH_3$ | $NO_2$ | H | H |
| DHP-176 | $C_{15}H_{31}$ | $CH_3$ | $CH_3$ | $C(O)OCH_2CH_3$ | $C(O)OCH(CH_3)_2$ | $OCH_3$ | $NO_2$ | H | H |
| DHP-177 | $C_{15}H_{31}$ | $CH_3$ | $CH_3$ | $C(O)OCH_2CH_3$ | $C(O)OCH_2CH_3$ | $OCH(CH_3)_2$ | $NO_2$ | H | H |
| DHP-178 | $C_{15}H_{31}$ | $CH_3$ | $CH_3$ | $C(O)OCH_2CH_3$ | $C(O)OCH_3$ | $OCH(CH_3)_2$ | $NO_2$ | H | H |
| DHP-179 | $C_{15}H_{31}$ | $CH_3$ | $CH_3$ | $C(O)OCH_2CH_3$ | $C(O)OCH(CH_3)_2$ | $OCH(CH_3)_2$ | $NO_2$ | H | H |
| DHP-180 | $C_{15}H_{31}$ | $CH_3$ | $CH_3$ | $C(O)OCH_2CH_3$ | $C(O)OCH_2CH_3$ | $OCH_2CH_3$ | $NO_2$ | H | H |
| DHP-181 | $C_{15}H_{31}$ | $CH_3$ | $CH_3$ | $C(O)OCH_2CH_3$ | $C(O)OCH_3$ | $OCH_2CH_3$ | $NO_2$ | H | H |
| DHP-182 | $C_{15}H_{31}$ | $CH_3$ | $CH_3$ | $C(O)OCH_2CH_3$ | $C(O)OCH(CH_3)_2$ | $OCH_2CH_3$ | $NO_2$ | H | H |
| DHP-183 | $C_{15}H_{31}$ | $CH_3$ | $CH_3$ | $C(O)OCH_3$ | $C(O)OCH_3$ | $OCH_3$ | $NO_2$ | H | H |
| DHP-184 | $C_{15}H_{31}$ | $CH_3$ | $CH_3$ | $C(O)OCH_3$ | $C(O)OCH_2CH_3$ | $OCH_3$ | $NO_2$ | H | H |
| DHP-185 | $C_{15}H_{31}$ | $CH_3$ | $CH_3$ | $C(O)OCH_3$ | $C(O)OCH(CH_3)_2$ | $OCH_3$ | $NO_2$ | H | H |
| DHP-186 | $C_{15}H_{31}$ | $CH_3$ | $CH_3$ | $C(O)OCH_3$ | $C(O)OCH_3$ | $OCH(CH_3)_2$ | $NO_2$ | H | H |
| DHP-187 | $C_{15}H_{31}$ | $CH_3$ | $CH_3$ | $C(O)OCH_3$ | $C(O)OCH_2CH_3$ | $OCH(CH_3)_2$ | $NO_2$ | H | H |
| DHP-188 | $C_{15}H_{31}$ | $CH_3$ | $CH_3$ | $C(O)OCH_3$ | $C(O)OCH(CH_3)_2$ | $OCH(CH_3)_2$ | $NO_2$ | H | H |
| DHP-189 | $C_{15}H_{31}$ | $CH_3$ | $CH_3$ | $C(O)OCH_3$ | $C(O)OCH_3$ | $OCH_2CH_3$ | $NO_2$ | H | H |
| DHP-190 | $C_{15}H_{31}$ | $CH_3$ | $CH_3$ | $C(O)OCH_3$ | $C(O)OCH_2CH_3$ | $OCH_2CH_3$ | $NO_2$ | H | H |
| DHP-191 | $C_{15}H_{31}$ | $CH_3$ | $CH_3$ | $C(O)OCH_3$ | $C(O)OCH(CH_3)_2$ | $OCH_2CH_3$ | $NO_2$ | H | H |
| DHP-192 | $C_{15}H_{31}$ | $CH_3$ | $CH_3$ | $C(O)OCH(CH_3)_2$ | $C(O)OCH(CH_3)_2$ | $OCH_3$ | $NO_2$ | H | H |
| DHP-193 | $C_{15}H_{31}$ | $CH_3$ | $CH_3$ | $C(O)OCH(CH_3)_2$ | $C(O)OCH_3$ | $OCH_3$ | $NO_2$ | H | H |
| DHP-194 | $C_{15}H_{31}$ | $CH_3$ | $CH_3$ | $C(O)OCH(CH_3)_2$ | $C(O)OCH_2CH_3$ | $OCH_3$ | $NO_2$ | H | H |
| DHP-195 | $C_{15}H_{31}$ | $CH_3$ | $CH_3$ | $C(O)OCH(CH_3)_2$ | $C(O)OCH(CH_3)_2$ | $OCH(CH_3)_2$ | $NO_2$ | H | H |
| DHP-196 | $C_{15}H_{31}$ | $CH_3$ | $CH_3$ | $C(O)OCH(CH_3)_2$ | $C(O)OCH_3$ | $OCH(CH_3)_2$ | $NO_2$ | H | H |
| DHP-197 | $C_{15}H_{31}$ | $CH_3$ | $CH_3$ | $C(O)OCH(CH_3)_2$ | $C(O)OCH_2CH_3$ | $OCH(CH_3)_2$ | $NO_2$ | H | H |
| DHP-198 | $C_{15}H_{31}$ | $CH_3$ | $CH_3$ | $C(O)OCH(CH_3)_2$ | $C(O)OCH(CH_3)_2$ | $OCH_2CH_3$ | $NO_2$ | H | H |
| DHP-199 | $C_{15}H_{31}$ | $CH_3$ | $CH_3$ | $C(O)OCH(CH_3)_2$ | $C(O)OCH_3$ | $OCH_2CH_3$ | $NO_2$ | H | H |
| DHP-200 | $C_{15}H_{31}$ | $CH_3$ | $CH_3$ | $C(O)OCH(CH_3)_2$ | $C(O)OCH_2CH_3$ | $OCH_2CH_3$ | $NO_2$ | H | H |
| DHP-201 | $C_{15}H_{31}$ | $CH_3$ | $CH_3$ | C(O)OH | C(O)OH | $OCH_3$ | $NO_2$ | H | H |
| DHP-202 | $C_{15}H_{31}$ | $CH_3$ | $CH_3$ | C(O)OH | $C(O)OCH_3$ | $OCH_3$ | $NO_2$ | H | H |
| DHP-203 | $C_{15}H_{31}$ | $CH_3$ | $CH_3$ | C(O)OH | $C(O)OCH_2CH_3$ | $OCH_3$ | $NO_2$ | H | H |
| DHP-204 | $C_{15}H_{31}$ | $CH_3$ | $CH_3$ | C(O)OH | $C(O)OCH(CH_3)_2$ | $OCH_2$ | $NO_2$ | H | H |
| DHP-205 | $C_{15}H_{31}$ | $CH_3$ | $CH_3$ | C(O)OH | C(O)OH | $OCH(CH_3)_2$ | $NO_2$ | H | H |
| DHP-206 | $C_{15}H_{31}$ | $CH_3$ | $CH_3$ | C(O)OH | $C(O)OCH_3$ | $OCH(CH_3)_2$ | $NO_2$ | H | H |
| DHP-207 | $C_{15}H_{31}$ | $CH_3$ | $CH_3$ | C(O)OH | $C(O)OCH_2CH_3$ | $OCH(CH_3)_2$ | $NO_2$ | H | H |
| DHP-208 | $C_{15}H_{31}$ | $CH_3$ | $CH_3$ | C(O)OH | $C(O)OCH(CH_3)_2$ | $OCH(CH_3)_2$ | $NO_2$ | H | H |
| DHP-209 | $C_{15}H_{31}$ | $CH_3$ | $CH_3$ | C(O)OH | C(O)OH | $OCH_2CH_3$ | $NO_2$ | H | H |
| DHP-210 | $C_{15}H_{31}$ | $CH_3$ | $CH_3$ | C(O)OH | $C(O)OCH_3$ | $OCH_2CH_3$ | $NO_2$ | H | H |
| DHP-211 | $C_{15}H_{31}$ | $CH_3$ | $CH_3$ | C(O)OH | $C(O)OCH_2CH_3$ | $OCH_2CH_3$ | $NO_2$ | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-212 | $C_{15}H_{31}$ | $CH_3$ | $CH_3$ | C(O)OH | C(O)OCH(CH$_3$)$_2$ | OCH$_2$CH$_3$ | NO$_2$ | H | H |
| DHP-213 | $C_{15}H_{31}$ | $CH_3$ | $CH_3$ | C(O)OCH$_3$ | C(O)OH | OCH$_3$ | NO$_2$ | H | H |
| DHP-214 | $C_{15}H_{31}$ | $CH_3$ | $CH_3$ | C(O)OCH$_2$CH$_3$ | C(O)OH | OCH$_3$ | NO$_2$ | H | H |
| DHP-215 | $C_{15}H_{31}$ | $CH_3$ | $CH_3$ | C(O)OCH(CH$_3$)$_2$ | C(O)OH | OCH$_3$ | NO$_2$ | H | H |
| DHP-216 | $C_{15}H_{31}$ | $CH_3$ | $CH_3$ | C(O)OCH$_3$ | C(O)OH | OCH(CH$_3$)$_2$ | NO$_2$ | H | H |
| DHP-217 | $C_{15}H_{31}$ | $CH_3$ | $CH_3$ | C(O)OCH$_2$CH$_3$ | C(O)OH | OCH(CH$_3$)$_2$ | NO$_2$ | H | H |
| DHP-218 | $C_{15}H_{31}$ | $CH_3$ | $CH_3$ | C(O)OCH(CH$_3$)$_2$ | C(O)OH | OCH(CH$_3$)$_2$ | NO$_2$ | H | H |
| DHP-219 | $C_{15}H_{31}$ | $CH_3$ | $CH_3$ | C(O)OCH$_3$ | C(O)OH | OCH$_2$CH$_3$ | NO$_2$ | H | H |
| DHP-220 | $C_{15}H_{31}$ | $CH_3$ | $CH_3$ | C(O)OCH$_2$CH$_3$ | C(O)OH | OCH$_2$CH$_3$ | NO$_2$ | H | H |
| DHP-221 | $C_{15}H_{31}$ | $CH_3$ | $CH_3$ | C(O)OCH(CH$_3$)$_2$ | C(O)OH | OCH$_2$CH$_3$ | NO$_2$ | H | H |
| DHP-222 | $C_{15}H_{31}$ | $CH_3$ | $CH_3$ | C(O)OCH$_2$CH$_3$ | C(O)OCH$_2$CH$_3$ | OCH$_3$ | H | NO$_2$ | H |
| DHP-223 | $C_{15}H_{31}$ | $CH_3$ | $CH_3$ | C(O)OCH$_2$CH$_3$ | C(O)OCH$_3$ | OCH$_3$ | H | NO$_2$ | H |
| DHP-224 | $C_{15}H_{31}$ | $CH_3$ | $CH_3$ | C(O)OCH$_2$CH$_3$ | C(O)OCH(CH$_3$)$_2$ | OCH$_3$ | H | NO$_2$ | H |
| DHP-225 | $C_{15}H_{31}$ | $CH_3$ | $CH_3$ | C(O)OCH$_2$CH$_3$ | C(O)OCH$_2$CH$_3$ | OCH(CH$_3$)$_2$ | H | NO$_2$ | H |
| DHP-226 | $C_{15}H_{31}$ | $CH_3$ | $CH_3$ | C(O)OCH$_2$CH$_3$ | C(O)OCH$_3$ | OCH(CH$_3$)$_2$ | H | NO$_2$ | H |
| DHP-227 | $C_{15}H_{31}$ | $CH_3$ | $CH_3$ | C(O)OCH$_2$CH$_3$ | C(O)OCH(CH$_3$)$_2$ | OCH(CH$_3$)$_2$ | H | NO$_2$ | H |
| DHP-228 | $C_{15}H_{31}$ | $CH_3$ | $CH_3$ | C(O)OCH$_2$CH$_3$ | C(O)OCH$_2$CH$_3$ | OCH$_2$CH$_3$ | H | NO$_2$ | H |
| DHP-229 | $C_{15}H_{31}$ | $CH_3$ | $CH_3$ | C(O)OCH$_2$CH$_3$ | C(O)OCH$_3$ | OCH$_2$CH$_3$ | H | NO$_2$ | H |
| DHP-230 | $C_{15}H_{31}$ | $CH_3$ | $CH_3$ | C(O)OCH$_2$CH$_3$ | C(O)OCH(CH$_3$)$_2$ | OCH$_2$CH$_3$ | H | NO$_2$ | H |
| DHP-231 | $C_{15}H_{31}$ | $CH_3$ | $CH_3$ | C(O)OCH$_3$ | C(O)OCH$_3$ | OCH$_3$ | H | NO$_2$ | H |
| DHP-232 | $C_{15}H_{31}$ | $CH_3$ | $CH_3$ | C(O)OCH$_3$ | C(O)OCH$_2$CH$_3$ | OCH$_3$ | H | NO$_2$ | H |
| DHP-233 | $C_{15}H_{31}$ | $CH_3$ | $CH_3$ | C(O)OCH$_3$ | C(O)OCH(CH$_3$)$_2$ | OCH$_3$ | H | NO$_2$ | H |
| DHP-234 | $C_{15}H_{31}$ | $CH_3$ | $CH_3$ | C(O)OCH$_3$ | C(O)OCH$_3$ | OCH(CH$_3$)$_2$ | H | NO$_2$ | H |
| DHP-235 | $C_{15}H_{31}$ | $CH_3$ | $CH_3$ | C(O)OCH$_3$ | C(O)OCH$_2$CH$_3$ | OCH(CH$_3$)$_2$ | H | NO$_2$ | H |
| DHP-236 | $C_{15}H_{31}$ | $CH_3$ | $CH_3$ | C(O)OCH$_3$ | C(O)OCH(CH$_3$)$_2$ | OCH(CH$_3$)$_2$ | H | NO$_2$ | H |
| DHP-237 | $C_{15}H_{31}$ | $CH_3$ | $CH_3$ | C(O)OCH$_3$ | C(O)OCH$_3$ | OCH$_2$CH$_3$ | H | NO$_2$ | H |
| DHP-238 | $C_{15}H_{31}$ | $CH_3$ | $CH_3$ | C(O)OCH$_3$ | C(O)OCH$_2$CH$_3$ | OCH$_2$CH$_3$ | H | NO$_2$ | H |
| DHP-239 | $C_{15}H_{31}$ | $CH_3$ | $CH_3$ | C(O)OCH$_3$ | C(O)OCH(CH$_3$)$_2$ | OCH$_2$CH$_3$ | H | NO$_2$ | H |
| DHP-240 | $C_{15}H_{31}$ | $CH_3$ | $CH_3$ | C(O)OCH(CH$_3$)$_2$ | C(O)OCH(CH$_3$)$_2$ | OCH$_3$ | H | NO$_2$ | H |
| DHP-241 | $C_{15}H_{31}$ | $CH_3$ | $CH_3$ | C(O)OCH(CH$_3$)$_2$ | C(O)OCH$_3$ | OCH$_3$ | H | NO$_2$ | H |
| DHP-242 | $C_{15}H_{31}$ | $CH_3$ | $CH_3$ | C(O)OCH(CH$_3$)$_2$ | C(O)OCH$_2$CH$_3$ | OCH$_3$ | H | NO$_2$ | H |
| DHP-243 | $C_{15}H_{31}$ | $CH_3$ | $CH_3$ | C(O)OCH(CH$_3$)$_2$ | C(O)OCH(CH$_3$)$_2$ | OCH(CH$_3$)$_2$ | H | NO$_2$ | H |
| DHP-244 | $C_{15}H_{31}$ | $CH_3$ | $CH_3$ | C(O)OCH(CH$_3$)$_2$ | C(O)OCH$_3$ | OCH(CH$_3$)$_2$ | H | NO$_2$ | H |
| DHP-245 | $C_{15}H_{31}$ | $CH_3$ | $CH_3$ | C(O)OCH(CH$_3$)$_2$ | C(O)OCH$_2$CH$_3$ | OCH(CH$_3$)$_2$ | H | NO$_2$ | H |
| DHP-246 | $C_{15}H_{31}$ | $CH_3$ | $CH_3$ | C(O)OCH(CH$_3$)$_2$ | C(O)OCH(CH$_3$)$_2$ | OCH$_2$CH$_3$ | H | NO$_2$ | H |
| DHP-247 | $C_{15}H_{31}$ | $CH_3$ | $CH_3$ | C(O)OCH(CH$_3$)$_2$ | C(O)OCH$_3$ | OCH$_2$CH$_3$ | H | NO$_2$ | H |
| DHP-248 | $C_{15}H_{31}$ | $CH_3$ | $CH_3$ | C(O)OCH(CH$_3$)$_2$ | C(O)OCH$_2$CH$_3$ | OCH$_2$CH$_3$ | H | NO$_2$ | H |
| DHP-249 | $C_{15}H_{31}$ | $CH_3$ | $CH_3$ | C(O)OH | C(O)OH | OCH$_3$ | H | NO$_2$ | H |
| DHP-250 | $C_{15}H_{31}$ | $CH_3$ | $CH_3$ | C(O)OH | C(O)OCH$_3$ | OCH$_3$ | H | NO$_2$ | H |
| DHP-251 | $C_{15}H_{31}$ | $CH_3$ | $CH_3$ | C(O)OH | C(O)OCH$_2$CH$_3$ | OCH$_3$ | H | NO$_2$ | H |
| DHP-252 | $C_{15}H_{31}$ | $CH_3$ | $CH_3$ | C(O)OH | C(O)OCH(CH$_3$)$_2$ | OCH$_3$ | H | NO$_2$ | H |
| DHP-253 | $C_{15}H_{31}$ | $CH_3$ | $CH_3$ | C(O)OH | C(O)OH | OCH(CH$_3$)$_2$ | H | NO$_2$ | H |
| DHP-254 | $C_{15}H_{31}$ | $CH_3$ | $CH_3$ | C(O)OH | C(O)OCH$_3$ | OCH(CH$_3$)$_2$ | H | NO$_2$ | H |
| DHP-255 | $C_{15}H_{31}$ | $CH_3$ | $CH_3$ | C(O)OH | C(O)OCH$_2$CH$_3$ | OCH(CH$_3$)$_2$ | H | NO$_2$ | H |
| DHP-256 | $C_{15}H_{31}$ | $CH_3$ | $CH_3$ | C(O)OH | C(O)OCH(CH$_3$)$_2$ | OCH(CH$_3$)$_2$ | H | NO$_2$ | H |
| DHP-257 | $C_{15}H_{31}$ | $CH_3$ | $CH_3$ | C(O)OH | C(O)OH | OCH$_2$CH$_3$ | H | NO$_2$ | H |
| DHP-258 | $C_{15}H_{31}$ | $CH_3$ | $CH_3$ | C(O)OH | C(O)OCH$_3$ | OCH$_2$CH$_3$ | H | NO$_2$ | H |
| DHP-259 | $C_{15}H_{31}$ | $CH_3$ | $CH_3$ | C(O)OH | C(O)OCH$_2$CH$_3$ | OCH$_2$CH$_3$ | H | NO$_2$ | H |
| DHP-260 | $C_{15}H_{31}$ | $CH_3$ | $CH_3$ | C(O)OH | C(O)OCH(CH$_3$)$_2$ | OCH$_2$CH$_3$ | H | NO$_2$ | H |
| DHP-261 | $C_{15}H_{31}$ | $CH_3$ | $CH_3$ | C(O)OCH$_3$ | C(O)OH | OCH$_3$ | H | NO$_2$ | H |
| DHP-262 | $C_{15}H_{31}$ | $CH_3$ | $CH_3$ | C(O)OCH$_2$CH$_3$ | C(O)OH | OCH$_3$ | H | NO$_2$ | H |
| DHP-263 | $C_{15}H_{31}$ | $CH_3$ | $CH_3$ | C(O)OCH(CH$_3$)$_2$ | C(O)OH | OCH$_3$ | H | NO$_2$ | H |
| DHP-264 | $C_{15}H_{31}$ | $CH_3$ | $CH_3$ | C(O)OCH$_3$ | C(O)OH | OCH(CH$_3$)$_2$ | H | NO$_2$ | H |
| DHP-265 | $C_{15}H_{31}$ | $CH_3$ | $CH_3$ | C(O)OCH$_2$CH$_3$ | C(O)OH | OCH(CH$_3$)$_2$ | H | NO$_2$ | H |
| DHP-266 | $C_{15}H_{31}$ | $CH_3$ | $CH_3$ | C(O)OCH(CH$_3$)$_2$ | C(O)OH | OCH(CH$_3$)$_2$ | H | NO$_2$ | H |
| DHP-267 | $C_{15}H_{31}$ | $CH_3$ | $CH_3$ | C(O)OCH$_3$ | C(O)OH | OCH$_2$CH$_3$ | H | NO$_2$ | H |
| DHP-268 | $C_{15}H_{31}$ | $CH_3$ | $CH_3$ | C(O)OCH$_2$CH$_3$ | C(O)OH | OCH$_2$CH$_3$ | H | NO$_2$ | H |
| DHP-269 | $C_{15}H_{31}$ | $CH_3$ | $CH_3$ | C(O)OCH(CH$_3$)$_2$ | C(O)OH | OCH$_2$CH$_3$ | H | NO$_2$ | H |
| DHP-270 | $C_{15}H_{31}$ | $CH_3$ | C# | C(O)OCH$_2$CH$_3$ | C(O)OCH$_2$CH$_3$ | OCH$_3$ | H | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-271 | $C_{15}H_{31}$ | $CH_3$ | C | $C(O)OCH_2CH_3$ | $C(O)OCH_3$ | $OCH_3$ | H | H | H |
| DHP-272 | $C_{15}H_{31}$ | $CH_3$ | C | $C(O)OCH_2CH_3$ | $C(O)OCH(CH_3)_2$ | $OCH_3$ | H | H | H |
| DHP-273 | $C_{15}H_{31}$ | $CH_3$ | C | $C(O)OCH_2CH_3$ | $C(O)OCH_2CH_3$ | $OCH(CH_3)_2$ | H | H | H |
| DHP-274 | $C_{15}H_{31}$ | $CH_3$ | C | $C(O)OCH_2CH_3$ | $C(O)OCH_3$ | $OCH(CH_3)_2$ | H | H | H |
| DHP-275 | $C_{15}H_{31}$ | $CH_3$ | C | $C(O)OCH_2CH_3$ | $C(O)OCH(CH_3)_2$ | $OCH(CH_3)_2$ | H | H | H |
| DHP-276 | $C_{15}H_{31}$ | $CH_3$ | C | $C(O)OCH_2CH_3$ | $C(O)OCH_2CH_3$ | $OCH_2CH_3$ | H | H | H |
| DHP-277 | $C_{15}H_{31}$ | $CH_3$ | C | $C(O)OCH_2CH_3$ | $C(O)OCH_3$ | $OCH_2CH_3$ | H | H | H |
| DHP-278 | $C_{15}H_{31}$ | $CH_3$ | C | $C(O)OCH_2CH_3$ | $C(O)OCH(CH_3)_2$ | $OCH_2CH_3$ | H | H | H |
| DHP-279 | $C_{15}H_{31}$ | $CH_3$ | C | $C(O)OCH_3$ | $C(O)OCH_3$ | $OCH_3$ | H | H | H |
| DHP-280 | $C_{15}H_{31}$ | $CH_3$ | C | $C(O)OCH_3$ | $C(O)OCH_2CH_3$ | $OCH_3$ | H | H | H |
| DHP-281 | $C_{15}H_{31}$ | $CH_3$ | C | $C(O)OCH_3$ | $C(O)OCH(CH_3)_2$ | $OCH_3$ | H | H | H |
| DHP-282 | $C_{15}H_{31}$ | $CH_3$ | C | $C(O)OCH_3$ | $C(O)OCH_3$ | $OCH(CH_3)_2$ | H | H | H |
| DHP-283 | $C_{15}H_{31}$ | $CH_3$ | C | $C(O)OCH_3$ | $C(O)OCH_2CH_3$ | $OCH(CH_3)_2$ | H | H | H |
| DHP-284 | $C_{15}H_{31}$ | $CH_3$ | C | $C(O)OCH_3$ | $C(O)OCH(CH_3)_2$ | $OCH(CH_3)_2$ | H | H | H |
| DHP-285 | $C_{15}H_{31}$ | $CH_3$ | C | $C(O)OCH_3$ | $C(O)OCH_3$ | $OCH_2CH_3$ | H | H | H |
| DHP-286 | $C_{15}H_{31}$ | $CH_3$ | C | $C(O)OCH_3$ | $C(O)OCH_2CH_3$ | $OCH_2CH_3$ | H | H | H |
| DHP-287 | $C_{15}H_{31}$ | $CH_3$ | C | $C(O)OCH_3$ | $C(O)OCH(CH_3)_2$ | $OCH_2CH_3$ | H | H | H |
| DHP-288 | $C_{15}H_{31}$ | $CH_3$ | C | $C(O)OCH(CH_3)_2$ | $C(O)OCH(CH_3)_2$ | $OCH_3$ | H | H | H |
| DHP-289 | $C_{15}H_{31}$ | $CH_3$ | C | $C(O)OCH(CH_3)_2$ | $C(O)OCH_3$ | $OCH_3$ | H | H | H |
| DHP-290 | $C_{15}H_{31}$ | $CH_3$ | C | $C(O)OCH(CH_3)_2$ | $C(O)OCH_2CH_3$ | $OCH_3$ | H | H | H |
| DHP-291 | $C_{15}H_{31}$ | $CH_3$ | C | $C(O)OCH(CH_3)_2$ | $C(O)OCH(CH_3)_2$ | $OCH(CH_3)_2$ | H | H | H |
| DHP-292 | $C_{15}H_{31}$ | $CH_3$ | C | $C(O)OCH(CH_3)_2$ | $C(O)OCH_3$ | $OCH(CH_3)_2$ | H | H | H |
| DHP-293 | $C_{15}H_{31}$ | $CH_3$ | C | $C(O)OCH(CH_3)_2$ | $C(O)OCH_2CH_3$ | $OCH(CH_3)_2$ | H | H | H |
| DHP-294 | $C_{15}H_{31}$ | $CH_3$ | C | $C(O)OCH(CH_3)_2$ | $C(O)OCH(CH_3)_2$ | $OCH_2CH_3$ | H | H | H |
| DHP-295 | $C_{15}H_{31}$ | $CH_3$ | C | $C(O)OCH(CH_3)_2$ | $C(O)OCH_3$ | $OCH_2CH_3$ | H | H | H |
| DHP-296 | $C_{15}H_{31}$ | $CH_3$ | C | $C(O)OCH(CH_3)_2$ | $C(O)OCH_2CH_3$ | $OCH_2CH_3$ | H | H | H |
| DHP-297 | $C_{15}H_{31}$ | $CH_3$ | C | $C(O)OH$ | $C(O)OH$ | $OCH_3$ | H | H | H |
| DHP-298 | $C_{15}H_{31}$ | $CH_3$ | C | $C(O)OH$ | $C(O)OCH_3$ | $OCH_3$ | H | H | H |
| DHP-299 | $C_{15}H_{31}$ | $CH_3$ | C | $C(O)OH$ | $C(O)OCH_2CH_3$ | $OCH_3$ | H | H | H |
| DHP-300 | $C_{15}H_{31}$ | $CH_3$ | C | $C(O)OH$ | $C(O)OCH(CH_3)_2$ | $OCH_3$ | H | H | H |
| DHP-301 | $C_{15}H_{31}$ | $CH_3$ | C | $C(O)OH$ | $C(O)OH$ | $OCH(CH_3)_2$ | H | H | H |
| DHP-302 | $C_{15}H_{31}$ | $CH_3$ | C | $C(O)OH$ | $C(O)OCH_3$ | $OCH(CH_3)_2$ | H | H | H |
| DHP-303 | $C_{15}H_{31}$ | $CH_3$ | C | $C(O)OH$ | $C(O)OCH_2CH_3$ | $OCH(CH_3)_2$ | H | H | H |
| DHP-304 | $C_{15}H_{31}$ | $CH_3$ | C | $C(O)OH$ | $C(O)OCH(CH_3)_2$ | $OCH(CH_3)_2$ | H | H | H |
| DHP-305 | $C_{15}H_{31}$ | $CH_3$ | C | $C(O)OH$ | $C(O)OH$ | $OCH_2CH_3$ | H | H | H |
| DHP-306 | $C_{15}H_{31}$ | $CH_3$ | C | $C(O)OH$ | $C(O)OCH_3$ | $OCH_2CH_3$ | H | H | H |
| DHP-307 | $C_{15}H_{31}$ | $CH_3$ | C | $C(O)OH$ | $C(O)OCH_2CH_3$ | $OCH_2CH_3$ | H | H | H |
| DHP-308 | $C_{15}H_{31}$ | $CH_3$ | C | $C(O)OH$ | $C(O)OCH(CH_3)_2$ | $OCH_2CH_3$ | H | H | H |
| DHP-309 | $C_{15}H_{31}$ | $CH_3$ | C | $C(O)OCH_3$ | $C(O)OH$ | $OCH_3$ | H | H | H |
| DHP-310 | $C_{15}H_{31}$ | $CH_3$ | C | $C(O)OCH_2CH_3$ | $C(O)OH$ | $OCH_3$ | H | H | H |
| DHP-311 | $C_{15}H_{31}$ | $CH_3$ | C | $C(O)OCH(CH_3)_2$ | $C(O)OH$ | $OCH_3$ | H | H | H |
| DHP-312 | $C_{15}H_{31}$ | $CH_3$ | C | $C(O)OCH_3$ | $C(O)OH$ | $OCH(CH_3)_2$ | H | H | H |
| DHP-313 | $C_{15}H_{31}$ | $CH_3$ | C | $C(O)OCH_2CH_3$ | $C(O)OH$ | $OCH(CH_3)_2$ | H | H | H |
| DHP-314 | $C_{15}H_{31}$ | $CH_3$ | C | $C(O)OCH(CH_3)_2$ | $C(O)OH$ | $OCH(CH_3)_2$ | H | H | H |
| DHP-315 | $C_{15}H_{31}$ | $CH_3$ | C | $C(O)OCH_3$ | $C(O)OH$ | $OCH_2CH_3$ | H | H | H |
| DHP-316 | $C_{15}H_{31}$ | $CH_3$ | C | $C(O)OCH_2CH_3$ | $C(O)OH$ | $OCH_2CH_3$ | H | H | H |
| DHP-317 | $C_{15}H_{31}$ | $CH_3$ | C | $C(O)OCH(CH_3)_2$ | $C(O)OH$ | $OCH_2CH_3$ | H | H | H |
| DHP-318 | $C_{15}H_{31}$ | $CH_3$ | $CH_3$ | $CH_2OCH_3$ | $CH_2OCH_3$ | $OCH_3$ | H | H | H |
| DHP-319 | $C_{15}H_{31}$ | $CH_3$ | $CH_3$ | $CH_2OCH_3$ | $CH_2OCH_2CH_3$ | $OCH_3$ | H | H | H |
| DHP-320 | $C_{15}H_{31}$ | $CH_3$ | $CH_3$ | $CH_2OCH_3$ | $CH_2OCH(CH_3)_2$ | $OCH_3$ | H | H | H |
| DHP-321 | $C_{15}H_{31}$ | $CH_3$ | $CH_3$ | $CH_2OCH_2CH_3$ | $CH_2OCH_3$ | $OCH(CH_3)_2$ | H | H | H |
| DHP-322 | $C_{15}H_{31}$ | $CH_3$ | $CH_3$ | $CH_2OCH_2CH_3$ | $CH_2OCH_2CH_3$ | $OCH(CH_3)_2$ | H | H | H |
| DHP-323 | $C_{15}H_{31}$ | $CH_3$ | $CH_3$ | $CH_2OCH_2CH_3$ | $CH_2OCH(CH_3)_2$ | $OCH(CH_3)_2$ | H | H | H |
| DHP-324 | $C_{15}H_{31}$ | $CH_3$ | $CH_3$ | $CH_2OCH(CH_3)_2$ | $CH_2OCH_3$ | $OCH_2CH_3$ | H | H | H |
| DHP-325 | $C_{15}H_{31}$ | $CH_3$ | $CH_3$ | $CH_2OCH(CH_3)_2$ | $CH_2OCH_2CH_3$ | $OCH_2CH_3$ | H | H | H |
| DHP-326 | $C_{15}H_{31}$ | $CH_3$ | $CH_3$ | $CH_2OCH(CH_3)_2$ | $CH_2OCH(CH_3)_2$ | $OCH_2CH_3$ | H | H | H |
| DHP-327 | $C_{10}H_{21}$ | $CH_3$ | $CH_3$ | $C(O)OCH_2CH_3$ | $C(O)OCH_3$ | $OCH_3$ | H | H | H |
| DHP-328 | $C_{10}H_{21}$ | $CH_3$ | $CH_3$ | $C(O)OCH_2CH_3$ | $C(O)OCH_2CH_3$ | $OCH_3$ | H | H | H |
| DHP-329 | $C_{10}H_{21}$ | $CH_3$ | $CH_3$ | $C(O)OCH_2CH_3$ | $C(O)OCH_3$ | $OCH_2CH_3$ | H | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-330 | $C_{10}H_{21}$ | $CH_3$ | $CH_3$ | $C(O)OCH_2CH_3$ | $C(O)OCH_2CH_3$ | $OCH_2CH_3$ | H | H | H |
| DHP-331 | $C_{10}H_{21}$ | $CH_3$ | $CH_3$ | $C(O)OCH_3$ | $C(O)OCH_3$ | $OCH(CH_3)_2$ | H | H | H |
| DHP-332 | $C_{10}H_{21}$ | $CH_3$ | $CH_3$ | $C(O)OCH_2CH_3$ | $C(O)OCH_3$ | $OCH(CH_3)_2$ | H | H | H |
| DHP-333 | $C_{10}H_{21}$ | $CH_3$ | $CH_3$ | $C(O)OCH_2CH_3$ | $C(O)OCH_2CH_3$ | $OCH(CH_3)_2$ | H | H | H |
| DHP-334 | $C_{10}H_{21}$ | $CH_3$ | $CH_3$ | $C(O)OCH(CH_3)_2$ | $C(O)OCH_3$ | $OCH_3$ | H | H | H |
| DHP-335 | $C_{10}H_{21}$ | $CH_3$ | $CH_3$ | $C(O)OCH(CH_3)_2$ | $C(O)OCH_2CH_3$ | $OCH_3$ | H | H | H |
| DHP-336 | $C_{10}H_{21}$ | $CH_3$ | $CH_3$ | $C(O)OCH(CH_3)_2$ | $C(O)OCH(CH_3)_2$ | $OCH_3$ | H | H | H |
| DHP-337 | $C_{10}H_{21}$ | $CH_3$ | $CH_3$ | $C(O)OCH(CH_3)_2$ | $C(O)OCH_3$ | $OCH_2CH_3$ | H | H | H |
| DHP-338 | $C_{10}H_{21}$ | $CH_3$ | $CH_3$ | $C(O)OCH(CH_3)_2$ | $C(O)OCH_2CH_3$ | $OCH_2CH_3$ | H | H | H |
| DHP-339 | $C_{10}H_{21}$ | $CH_3$ | $CH_3$ | $C(O)OCH(CH_3)_2$ | $C(O)OCH(CH_3)_2$ | $OCH_2CH_3$ | H | H | H |
| DHP-340 | $C_{10}H_{21}$ | $CH_3$ | $CH_3$ | $C(O)OCH(CH_3)_2$ | $C(O)OCH_3$ | $OCH(CH_3)_2$ | H | H | H |
| DHP-341 | $C_{10}H_{21}$ | $CH_3$ | $CH_3$ | $C(O)OCH(CH_3)_2$ | $C(O)OCH_2CH_3$ | $OCH(CH_3)_2$ | H | H | H |
| DHP-342 | $C_{10}H_{21}$ | $CH_3$ | $CH_3$ | $C(O)OCH(CH_3)_2$ | $C(O)OCH(CH_3)_2$ | $OCH(CH_3)_2$ | H | H | H |
| DHP-343 | $C_{10}H_{21}$ | $CH_3$ | $CH_3$ | $C(O)OCH_2CH_3$ | $C(O)OCH_2CH_3$ | $OCH_3$ | H | H | H |
| DHP-344 | $C_{10}H_{21}$ | $CH_3$ | $CH_3$ | $C(O)OCH_2CH_3$ | $C(O)OCH_2CH_3$ | $OCH_2CH_3$ | H | H | H |
| DHP-345 | $C_{10}H_{21}$ | $CH_3$ | $CH_3$ | $C(O)OCH_3$ | $C(O)OCH_3$ | $OCH_2CH_3$ | H | H | H |
| DHP-346 | $C_{10}H_{21}$ | $CH_3$ | $CH_3$ | $C(O)OCH_3$ | $C(O)OCH_3$ | $OCH_3$ | H | H | H |
| DHP-347 | $C_{10}H_{21}$ | $CH_3$ | A* | $C(O)OCH_2CH_3$ | $C(O)OCH_2CH_3$ | $OCH_3$ | H | H | H |
| DHP-348 | $C_{10}H_{21}$ | $CH_3$ | A | $C(O)OCH_2CH_3$ | $C(O)OCH_3$ | $OCH_3$ | H | H | H |
| DHP-349 | $C_{10}H_{21}$ | $CH_3$ | A | $C(O)OCH_2CH_3$ | $C(O)OCH(CH_3)_2$ | $OCH_3$ | H | H | H |
| DHP-350 | $C_{10}H_{21}$ | $CH_3$ | A | $C(O)OCH_2CH_3$ | $C(O)OCH_2CH_3$ | $OCH(CH_3)_2$ | H | H | H |
| DHP-351 | $C_{10}H_{21}$ | $CH_3$ | A | $C(O)OCH_2CH_3$ | $C(O)OCH_3$ | $OCH(CH_3)_2$ | H | H | H |
| DHP-352 | $C_{10}H_{21}$ | $CH_3$ | A | $C(O)OCH_2CH_3$ | $C(O)OCH(CH_3)_2$ | $OCH(CH_3)_2$ | H | H | H |
| DHP-353 | $C_{10}H_{21}$ | $CH_3$ | A | $C(O)OCH_2CH_3$ | $C(O)OCH_2CH_3$ | $OCH_2CH_3$ | H | H | H |
| DHP-354 | $C_{10}H_{21}$ | $CH_3$ | A | $C(O)OCH_2CH_3$ | $C(O)OCH_3$ | $OCH_2CH_3$ | H | H | H |
| DHP-355 | $C_{10}H_{21}$ | $CH_3$ | A | $C(O)OCH_2CH_3$ | $C(O)OCH(CH_3)_2$ | $OCH_2CH_3$ | H | H | H |
| DHP-356 | $C_{10}H_{21}$ | $CH_3$ | A | $C(O)OCH_3$ | $C(O)OCH_3$ | $OCH_3$ | H | H | H |
| DHP-357 | $C_{10}H_{21}$ | $CH_3$ | A | $C(O)OCH_3$ | $C(O)OCH_2CH_3$ | $OCH_3$ | H | H | H |
| DHP-358 | $C_{10}H_{21}$ | $CH_3$ | A | $C(O)OCH_3$ | $C(O)OCH(CH_3)_2$ | $OCH_3$ | H | H | H |
| DHP-359 | $C_{10}H_{21}$ | $CH_3$ | A | $C(O)OCH_3$ | $C(O)OCH_3$ | $OCH(CH_3)_2$ | H | H | H |
| DHP-360 | $C_{10}H_{21}$ | $CH_3$ | A | $C(O)OCH_3$ | $C(O)OCH_2CH_3$ | $OCH(CH_3)_2$ | H | H | H |
| DHP-361 | $C_{10}H_{21}$ | $CH_3$ | A | $C(O)OCH_3$ | $C(O)OCHCH_3)_2$ | $OCH(CH_3)_2$ | H | H | H |
| DHP-362 | $C_{10}H_{21}$ | $CH_3$ | A | $C(O)OCH_3$ | $C(O)OCH_3$ | $OCH_2CH_3$ | H | H | H |
| DHP-363 | $C_{10}H_{21}$ | $CH_3$ | A | $C(O)OCH_3$ | $C(O)OCH_2CH_3$ | $OCH_2CH_3$ | H | H | H |
| DHP-364 | $C_{10}H_{21}$ | $CH_3$ | A | $C(O)OCH_3$ | $C(O)OCH(CH_3)_2$ | $OCH_2CH_3$ | H | H | H |
| DHP-365 | $C_{10}H_{21}$ | $CH_3$ | A | $C(O)OCH(CH_3)_2$ | $C(O)OCH(CH_3)_2$ | $OCH_3$ | H | H | H |
| DHP-366 | $C_{10}H_{21}$ | $CH_3$ | A | $C(O)OCH(CH_3)_2$ | $C(O)OCH_3$ | $OCH_3$ | H | H | H |
| DHP-367 | $C_{10}H_{21}$ | $CH_3$ | A | $C(O)OCH(CH_3)_2$ | $C(O)OCH_2CH_3$ | $OCH_3$ | H | H | H |
| DHP-368 | $C_{10}H_{21}$ | $CH_3$ | A | $C(O)OCH(CH_3)_2$ | $C(O)OCH(CH_3)_2$ | $OCH(CH_3)_2$ | H | H | H |
| DHP-369 | $C_{10}H_{21}$ | $CH_3$ | A | $C(O)OCH(CH_3)_2$ | $C(O)OCH_3$ | $OCH(CH_3)_2$ | H | H | H |
| DHP-370 | $C_{10}H_{21}$ | $CH_3$ | A | $C(O)OCH(CH_3)_2$ | $C(O)OCH_2CH_3$ | $OCH(CH_3)_2$ | H | H | H |
| DHP-371 | $C_{10}H_{21}$ | $CH_3$ | A | $C(O)OCH(CH_3)_2$ | $C(O)OCH(CH_3)_2$ | $OCH_2CH_3$ | H | H | H |
| DHP-372 | $C_{10}H_{21}$ | $CH_3$ | A | $C(O)OCH(CH_3)_2$ | $C(O)OCH_3$ | $OCH_2CH_3$ | H | H | H |
| DHP-373 | $C_{10}H_{21}$ | $CH_3$ | A | $C(O)OCH(CH_3)_2$ | $C(O)OCH_2CH_3$ | $OCH_2CH_3$ | H | H | H |
| DHP-374 | $C_{10}H_{21}$ | $CH_3$ | A | $C(O)OH$ | $C(O)OH$ | $OCH_3$ | H | H | H |
| DHP-375 | $C_{10}H_{21}$ | $CH_3$ | A | $C(O)OH$ | $C(O)OCH_3$ | $OCH_3$ | H | H | H |
| DHP-376 | $C_{10}H_{21}$ | $CH_3$ | A | $C(O)OH$ | $C(O)OCH_2CH_3$ | $OCH_3$ | H | H | H |
| DHP-377 | $C_{10}H_{21}$ | $CH_3$ | A | $C(O)OH$ | $C(O)OCH(CH_3)_2$ | $OCH_3$ | H | H | H |
| DHP-378 | $C_{10}H_{21}$ | $CH_3$ | A | $C(O)OH$ | $C(O)OH$ | $OCH(CH_3)_2$ | H | H | H |
| DHP-379 | $C_{10}H_{21}$ | $CH_3$ | A | $C(O)OH$ | $C(O)OCH_3$ | $OCH(CH_3)_2$ | H | H | H |
| DHP-380 | $C_{10}H_{21}$ | $CH_3$ | A | $C(O)OH$ | $C(O)OCH_2CH_3$ | $OCH(CH_3)_2$ | H | H | H |
| DHP-381 | $C_{10}H_{21}$ | $CH_3$ | A | $C(O)OH$ | $C(O)OCH(CH_3)_2$ | $OCH(CH_3)_2$ | H | H | H |
| DHP-382 | $C_{10}H_{21}$ | $CH_3$ | A | $C(O)OH$ | $C(O)OH$ | $OCH_2CH_3$ | H | H | H |
| DHP-383 | $C_{10}H_{21}$ | $CH_3$ | A | $C(O)OH$ | $C(O)OCH_3$ | $OCH_2CH_3$ | H | H | H |
| DHP-384 | $C_{10}H_{21}$ | $CH_3$ | A | $C(O)OH$ | $C(O)OCH_2CH_3$ | $OCH_2CH_3$ | H | H | H |
| DHP-385 | $C_{10}H_{21}$ | $CH_3$ | A | $C(O)OH$ | $C(O)OCH(CH_3)_2$ | $OCH_2CH_3$ | H | H | H |
| DHP-386 | $C_{10}H_{21}$ | $CH_3$ | A | $C(O)OCH_3$ | $C(O)OH$ | $OCH_3$ | H | H | H |
| DHP-387 | $C_{10}H_{21}$ | $CH_3$ | A | $C(O)OCH_2CH_3$ | $C(O)OH$ | $OCH_3$ | H | H | H |
| DHP-388 | $C_{10}H_{21}$ | $CH_3$ | A | $C(O)OCH(CH_3)_2$ | $C(O)OH$ | $OCH_3$ | H | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-389 | $C_{10}H_{21}$ | $CH_3$ | A | $C(O)OCH_3$ | $C(O)OH$ | $OCH(CH_3)_2$ | H | H | H |
| DHP-390 | $C_{10}H_{21}$ | $CH_3$ | A | $C(O)OCH_2CH_3$ | $C(O)OH$ | $OCH(CH_3)_2$ | H | H | H |
| DHP-391 | $C_{10}H_{21}$ | $CH_3$ | A | $C(O)OCH(CH_3)_2$ | $C(O)OH$ | $OCH(CH_3)_2$ | H | H | H |
| DHP-392 | $C_{10}H_{21}$ | $CH_3$ | A | $C(O)OCH_3$ | $C(O)OH$ | $OCH_2CH_3$ | H | H | H |
| DHP-393 | $C_{10}H_{21}$ | $CH_3$ | A | $C(O)OCH_2CH_3$ | $C(O)OH$ | $OCH_2CH_3$ | H | H | H |
| DHP-394 | $C_{10}H_{21}$ | $CH_3$ | A | $C(O)OCH(CH_3)_2$ | $C(O)OH$ | $OCH_2CH_3$ | H | H | H |
| DHP-395 | $C_{10}H_{21}$ | $CH_3$ | $CH_3$ | $C(O)OCH_2CH_2OCH_3$ | $C(O)OCH_2CH_3$ | $OCH_2CH_3$ | H | H | H |
| DHP-396 | $C_{10}H_{21}$ | $CH_3$ | $CH_3$ | $C(O)OCH_2CH_2OCH_3$ | $C(O)OCH_3$ | $OCH_2CH_3$ | H | H | H |
| DHP-397 | $C_{10}H_{21}$ | $CH_3$ | $CH_3$ | $C(O)OCH_2CH_2OCH_3$ | $C(O)OCH(CH_3)_2$ | $OCH_2CH_3$ | H | H | H |
| DHP-398 | $C_{10}H_{21}$ | $CH_3$ | $CH_3$ | $C(O)OCH_2CH_2OCH_3$ | $C(O)OCH_2CH_3$ | $OCH(CH_3)_2$ | H | H | H |
| DHP-399 | $C_{10}H_{21}$ | $CH_3$ | $CH_3$ | $C(O)OCH_2CH_2OCH_3$ | $C(O)OCH_3$ | $OCH(CH_3)_2$ | H | H | H |
| DHP-400 | $C_{10}H_{21}$ | $CH_3$ | $CH_3$ | $C(O)OCH_2CH_2OCH_3$ | $C(O)OCH(CH_3)_2$ | $OCH(CH_3)_2$ | H | H | H |
| DHP-401 | $C_{10}H_{21}$ | $CH_3$ | $CH_3$ | $C(O)OCH_2CH_2OCH_3$ | $C(O)OCH_2CH_3$ | $OCH_3$ | H | H | H |
| DHP-402 | $C_{10}H_{21}$ | $CH_3$ | $CH_3$ | $C(O)OCH_2CH_2OCH_3$ | $C(O)OCH_3$ | $OCH_3$ | H | H | H |
| DHP-403 | $C_{10}H_{21}$ | $CH_3$ | $CH_3$ | $C(O)OCH_2CH_2OCH_3$ | $C(O)OCH(CH_3)_2$ | $OCH_3$ | H | H | H |
| DHP-404 | $C_{10}H_{21}$ | B** | $CH_3$ | $C(O)OCH_2CH_3$ | $C(O)OCH_2CH_3$ | $OCH_3$ | H | H | H |
| DHP-405 | $C_{10}H_{21}$ | B | $CH_3$ | $C(O)OCH_2CH_3$ | $C(O)OCH_3$ | $OCH_3$ | H | H | H |
| DHP-406 | $C_{10}H_{21}$ | B | $CH_3$ | $C(O)OCH_2CH_3$ | $C(O)OCH(CH_3)_2$ | $OCH_3$ | H | H | H |
| DHP-407 | $C_{10}H_{21}$ | B | $CH_3$ | $C(O)OCH_2CH_3$ | $C(O)OCH_2CH_3$ | $OCH(CH_3)_2$ | H | H | H |
| DHP-408 | $C_{10}H_{21}$ | B | $CH_3$ | $C(O)OCH_2CH_3$ | $C(O)OCH_3$ | $OCH(CH_3)_2$ | H | H | H |
| DHP-409 | $C_{10}H_{21}$ | B | $CH_3$ | $C(O)OCH_2CH_3$ | $C(O)OCH(CH_3)_2$ | $OCH(CH_3)_2$ | H | H | H |
| DHP-410 | $C_{10}H_{21}$ | B | $CH_3$ | $C(O)OCH_2CH_3$ | $C(O)OCH_2CH_3$ | $OCH_2CH_3$ | H | H | H |
| DHP-411 | $C_{10}H_{21}$ | B | $CH_3$ | $C(O)OCH_2CH_3$ | $C(O)OCH_3$ | $OCH_2CH_3$ | H | H | H |
| DHP-412 | $C_{10}H_{21}$ | B | $CH_3$ | $C(O)OCH_2CH_3$ | $C(O)OCH(CH_3)_2$ | $OCH_2CH_3$ | H | H | H |
| DHP-413 | $C_{10}H_{21}$ | B | $CH_3$ | $C(O)OCH_3$ | $C(O)OCH_3$ | $OCH_3$ | H | H | H |
| DHP-414 | $C_{10}H_{21}$ | B | $CH_3$ | $C(O)OCH_3$ | $C(O)OCH_2CH_3$ | $OCH_3$ | H | H | H |
| DHP-415 | $C_{10}H_{21}$ | B | $CH_3$ | $C(O)OCH_3$ | $C(O)OCH(CH_3)_2$ | $OCH_3$ | H | H | H |
| DHP-416 | $C_{10}H_{21}$ | B | $CH_3$ | $C(O)OCH_3$ | $C(O)OCH_3$ | $OCH(CH_3)_2$ | H | H | H |
| DHP-417 | $C_{10}H_{21}$ | B | $CH_3$ | $C(O)OCH_3$ | $C(O)OCH_2CH_3$ | $OCH(CH_3)_2$ | H | H | H |
| DHP-418 | $C_{10}H_{21}$ | B | $CH_3$ | $C(O)OCH_3$ | $C(O)OCH(CH_3)_2$ | $OCH(CH_3)_2$ | H | H | H |
| DHP-419 | $C_{10}H_{21}$ | B | $CH_3$ | $C(O)OCH_3$ | $C(O)OCH_3$ | $OCH_2CH_3$ | H | H | H |
| DHP-420 | $C_{10}H_{21}$ | B | $CH_3$ | $C(O)OCH_3$ | $C(O)OCH_2CH_3$ | $OCH_2CH_3$ | H | H | H |
| DHP-421 | $C_{10}H_{21}$ | B | $CH_3$ | $C(O)OCH_3$ | $C(O)OCH(CH_3)_2$ | $OCH_2CH_3$ | H | H | H |
| DHP-422 | $C_{10}H_{21}$ | B | $CH_3$ | $C(O)OCH(CH_3)_2$ | $C(O)OCH(CH_3)_2$ | $OCH_3$ | H | H | H |
| DHP-423 | $C_{10}H_{21}$ | B | $CH_3$ | $C(O)OCH(CH_3)_2$ | $C(O)OCH_3$ | $OCH_3$ | H | H | H |
| DHP-424 | $C_{10}H_{21}$ | B | $CH_3$ | $C(O)OCH(CH_3)_2$ | $C(O)OCH_2CH_3$ | $OCH_3$ | H | H | H |
| DHP-425 | $C_{10}H_{21}$ | B | $CH_3$ | $C(O)OCH(CH_3)_2$ | $C(O)OCH(CH_3)_2$ | $OCH(CH_3)_2$ | H | H | H |
| DHP-426 | $C_{10}H_{21}$ | B | $CH_3$ | $C(O)OCH(CH_3)_2$ | $C(O)OCH_3$ | $OCH(CH_3)_2$ | H | H | H |
| DHP-427 | $C_{10}H_{21}$ | B | $CH_3$ | $C(O)OCH(CH_3)_2$ | $C(O)OCH_2CH_3$ | $OCH(CH_3)_2$ | H | H | H |
| DHP-428 | $C_{10}H_{21}$ | B | $CH_3$ | $C(O)OCH(CH_3)_2$ | $C(O)OCH(CH_3)_2$ | $OCH_2CH_3$ | H | H | H |
| DHP-429 | $C_{10}H_{21}$ | B | $CH_3$ | $C(O)OCH(CH_3)_2$ | $C(O)OCH_3$ | $OCH_2CH_3$ | H | H | H |
| DHP-430 | $C_{10}H_{21}$ | B | $CH_3$ | $C(O)OCH(CH_3)_2$ | $C(O)OCH_2CH_3$ | $OCH_2CH_3$ | H | H | H |
| DHP-431 | $C_{10}H_{21}$ | B | $CH_3$ | $C(O)OH$ | $C(O)OH$ | $OCH_3$ | H | H | H |
| DHP-432 | $C_{10}H_{21}$ | B | $CH_3$ | $C(O)OH$ | $C(O)OCH_3$ | $OCH_3$ | H | H | H |
| DHP-433 | $C_{10}H_{21}$ | B | $CH_3$ | $C(O)OH$ | $C(O)OCH_2CH_3$ | $OCH_3$ | H | H | H |
| DHP-434 | $C_{10}H_{21}$ | B | $CH_3$ | $C(O)OH$ | $C(O)OCH(CH_3)_2$ | $OCH_3$ | H | H | H |
| DHP-435 | $C_{10}H_{21}$ | B | $CH_3$ | $C(O)OH$ | $C(O)OH$ | $OCH(CH_3)_2$ | H | H | H |
| DHP-436 | $C_{10}H_{21}$ | B | $CH_3$ | $C(O)OH$ | $C(O)OCH_3$ | $OCH(CH_3)_2$ | H | H | H |
| DHP-437 | $C_{10}H_{21}$ | B | $CH_3$ | $C(O)OH$ | $C(O)OCH_2CH_3$ | $OCH(CH_3)_2$ | H | H | H |
| DHP-438 | $C_{10}H_{21}$ | B | $CH_3$ | $C(O)OH$ | $C(O)OCH(CH_3)_2$ | $OCH(CH_3)_2$ | H | H | H |
| DHP-439 | $C_{10}H_{21}$ | B | $CH_3$ | $C(O)OH$ | $C(O)OH$ | $OCH_2CH_3$ | H | H | H |
| DHP-440 | $C_{10}H_{21}$ | B | $CH_3$ | $C(O)OH$ | $C(O)OCH_3$ | $OCH_2CH_3$ | H | H | H |
| DHP-441 | $C_{10}H_{21}$ | B | $CH_3$ | $C(O)OH$ | $C(O)OCH_2CH_3$ | $OCH_2CH_3$ | H | H | H |
| DHP-442 | $C_{10}H_{21}$ | B | $CH_3$ | $C(O)OH$ | $C(O)OCH(CH_3)_2$ | $OCH_2CH_3$ | H | H | H |
| DHP-443 | $C_{10}H_{21}$ | B | $CH_3$ | $C(O)OCH_3$ | $C(O)OH$ | $OCH_3$ | H | H | H |
| DHP-444 | $C_{10}H_{21}$ | B | $CH_3$ | $C(O)OCH_2CH_3$ | $C(O)OH$ | $OCH_3$ | H | H | H |
| DHP-445 | $C_{10}H_{21}$ | B | $CH_3$ | $C(O)OCH(CH_3)_2$ | $C(O)OH$ | $OCH_3$ | H | H | H |
| DHP-446 | $C_{10}H_{21}$ | B | $CH_3$ | $C(O)OCH_3$ | $C(O)OH$ | $OCH(CH_3)_2$ | H | H | H |
| DHP-447 | $C_{10}H_{21}$ | B | $CH_3$ | $C(O)OCH_2CH_3$ | $C(O)OH$ | $OCH(CH_3)_2$ | H | H | H |

TABLE I-continued

| Comp'd Number | R₁ | R₂ | R₃ | R₄ | R₅ | R₆ | R₇ | R₈ | R₉ |
|---|---|---|---|---|---|---|---|---|---|
| DHP-448 | $C_{10}H_{21}$ | B | $CH_3$ | $C(O)OCH(CH_3)_2$ | $C(O)OH$ | $OCH(CH_3)_2$ | H | H | H |
| DHP-449 | $C_{10}H_{21}$ | B | $CH_3$ | $C(O)OCH_3$ | $C(O)OH$ | $OCH_2CH_3$ | H | H | H |
| DHP-450 | $C_{10}H_{21}$ | B | $CH_3$ | $C(O)OCH_2CH_3$ | $C(O)OH$ | $OCH_2CH_3$ | H | H | H |
| DHP-451 | $C_{10}H_{21}$ | B | $CH_3$ | $C(O)OCH(CH_3)_2$ | $C(O)OH$ | $OCH_2CH_3$ | H | H | H |
| DHP-452 | $C_{10}H_{21}$ | $CH_3$ | $CH_3$ | $C(O)OCH_2CH_3$ | $C(O)OCH_2CH_3$ | $OCH_3$ | $NO_2$ | $NO_2$ | H |
| DHP-453 | $C_{10}H_{21}$ | $CH_3$ | $CH_3$ | $C(O)OCH_2CH_3$ | $C(O)OCH_3$ | $OCH_3$ | $NO_2$ | $NO_2$ | H |
| DHP-454 | $C_{10}H_{21}$ | $CH_3$ | $CH_3$ | $C(O)OCH_2CH_3$ | $C(O)OCH(CH_3)_2$ | $OCH_3$ | $NO_2$ | $NO_2$ | H |
| DHP-455 | $C_{10}H_{21}$ | $CH_3$ | $CH_3$ | $C(O)OCH_2CH_3$ | $C(O)OCH_2CH_3$ | $OCH(CH_3)_2$ | $NO_2$ | $NO_2$ | H |
| DHP-456 | $C_{10}H_{21}$ | $CH_3$ | $CH_3$ | $C(O)OCH_2CH_3$ | $C(O)OCH_3$ | $OCH(CH_3)_2$ | $NO_2$ | $NO_2$ | H |
| DHP-457 | $C_{10}H_{21}$ | $CH_3$ | $CH_3$ | $C(O)OCH_2CH_3$ | $C(O)OCH(CH_3)_2$ | $OCH(CH_3)_2$ | $NO_2$ | $NO_2$ | H |
| DHP-458 | $C_{10}H_{21}$ | $CH_3$ | $CH_3$ | $C(O)OCH_2CH_3$ | $C(O)OCH_2CH_3$ | $OCH_2CH_3$ | $NO_2$ | $NO_2$ | H |
| DHP-459 | $C_{10}H_{21}$ | $CH_3$ | $CH_3$ | $C(O)OCH_2CH_3$ | $C(O)OCH_3$ | $OCH_2CH_3$ | $NO_2$ | $NO_2$ | H |
| DHP-460 | $C_{10}H_{21}$ | $CH_3$ | $CH_3$ | $C(O)OCH_2CH_3$ | $C(O)OCH(CH_3)_2$ | $OCH_2CH_3$ | $NO_2$ | $NO_2$ | H |
| DHP-461 | $C_{10}H_{21}$ | $CH_3$ | $CH_3$ | $C(O)OCH_3$ | $C(O)OCH_3$ | $OCH_3$ | $NO_2$ | $NO_2$ | H |
| DHP-462 | $C_{10}H_{21}$ | $CH_3$ | $CH_3$ | $C(O)OCH_3$ | $C(O)OCH_2CH_3$ | $OCH_3$ | $NO_2$ | $NO_2$ | H |
| DHP-463 | $C_{10}H_{21}$ | $CH_3$ | $CH_3$ | $C(O)OCH_3$ | $C(O)OCH(CH_3)_2$ | $OCH_3$ | $NO_2$ | $NO_2$ | H |
| DHP-464 | $C_{10}H_{21}$ | $CH_3$ | $CH_3$ | $C(O)OCH_3$ | $C(O)OCH_3$ | $OCH(CH_3)_2$ | $NO_2$ | $NO_2$ | H |
| DHP-465 | $C_{10}H_{21}$ | $CH_3$ | $CH_3$ | $C(O)OCH_3$ | $C(O)OCH_2CH_3$ | $OCH(CH_3)_2$ | $NO_2$ | $NO_2$ | H |
| DHP-466 | $C_{10}H_{21}$ | $CH_3$ | $CH_3$ | $C(O)OCH_3$ | $C(O)OCH(CH_3)_2$ | $OCH(CH_3)_2$ | $NO_2$ | $NO_2$ | H |
| DHP-467 | $C_{10}H_{21}$ | $CH_3$ | $CH_3$ | $C(O)OCH_3$ | $C(O)OCH_3$ | $OCH_2CH_3$ | $NO_2$ | $NO_2$ | H |
| DHP-468 | $C_{10}H_{21}$ | $CH_3$ | $CH_3$ | $C(O)OCH_3$ | $C(O)OCH_2CH_3$ | $OCH_2CH_3$ | $NO_2$ | $NO_2$ | H |
| DHP-469 | $C_{10}H_{21}$ | $CH_3$ | $CH_3$ | $C(O)OCH_3$ | $C(O)OCH(CH_3)_2$ | $OCH_2CH_3$ | $NO_2$ | $NO_2$ | H |
| DHP-470 | $C_{10}H_{21}$ | $CH_3$ | $CH_3$ | $C(O)OCH(CH_3)_2$ | $C(O)OCH(CH_3)_2$ | $OCH_3$ | $NO_2$ | $NO_2$ | H |
| DHP-471 | $C_{10}H_{21}$ | $CH_3$ | $CH_3$ | $C(O)OCH(CH_3)_2$ | $C(O)OCH_3$ | $OCH_3$ | $NO_2$ | $NO_2$ | H |
| DHP-472 | $C_{10}H_{21}$ | $CH_3$ | $CH_3$ | $C(O)OCH(CH_3)_2$ | $C(O)OCH_2CH_3$ | $OCH_3$ | $NO_2$ | $NO_2$ | H |
| DHP-473 | $C_{10}H_{21}$ | $CH_3$ | $CH_3$ | $C(O)OCH(CH_3)_2$ | $C(O)OCH(CH_3)_2$ | $OCH(CH_3)_2$ | $NO_2$ | $NO_2$ | H |
| DHP-474 | $C_{10}H_{21}$ | $CH_3$ | $CH_3$ | $C(O)OCH(CH_3)_2$ | $C(O)OCH_3$ | $OCH(CH_3)_2$ | $NO_2$ | $NO_2$ | H |
| DHP-475 | $C_{10}H_{21}$ | $CH_3$ | $CH_3$ | $C(O)OCH(CH_3)_2$ | $C(O)OCH_2CH_3$ | $OCH(CH_3)_2$ | $NO_2$ | $NO_2$ | H |
| DHP-476 | $C_{10}H_{21}$ | $CH_3$ | $CH_3$ | $C(O)OCH(CH_3)_2$ | $C(O)OCH(CH_3)_2$ | $OCH_2CH_3$ | $NO_2$ | $NO_2$ | H |
| DHP-477 | $C_{10}H_{21}$ | $CH_3$ | $CH_3$ | $C(O)OCH(CH_3)_2$ | $C(O)OCH_3$ | $OCH_2CH_3$ | $NO_2$ | $NO_2$ | H |
| DHP-478 | $C_{10}H_{21}$ | $CH_3$ | $CH_3$ | $C(O)OCH(CH_3)_2$ | $C(O)OCH_2CH_3$ | $OCH_2CH_3$ | $NO_2$ | $NO_2$ | H |
| DHP-479 | $C_{10}H_{21}$ | $CH_3$ | $CH_3$ | $C(O)OH$ | $C(O)OH$ | $OCH_3$ | $NO_2$ | $NO_2$ | H |
| DHP-480 | $C_{10}H_{21}$ | $CH_3$ | $CH_3$ | $C(O)OH$ | $C(O)OCH_3$ | $OCH_3$ | $NO_2$ | $NO_2$ | H |
| DHP-481 | $C_{10}H_{21}$ | $CH_3$ | $CH_3$ | $C(O)OH$ | $C(O)OCH_2CH_3$ | $OCH_3$ | $NO_2$ | $NO_2$ | H |
| DHP-482 | $C_{10}H_{21}$ | $CH_3$ | $CH_3$ | $C(O)OH$ | $C(O)OCH(CH_3)_2$ | $OCH_3$ | $NO_2$ | $NO_2$ | H |
| DHP-483 | $C_{10}H_{21}$ | $CH_3$ | $CH_3$ | $C(O)OH$ | $C(O)OH$ | $OCH(CH_3)_2$ | $NO_2$ | $NO_2$ | H |
| DHP-484 | $C_{10}H_{21}$ | $CH_3$ | $CH_3$ | $C(O)OH$ | $C(O)OCH_3$ | $OCH(CH_3)_2$ | $NO_2$ | $NO_2$ | H |
| DHP-485 | $C_{10}H_{21}$ | $CH_3$ | $CH_3$ | $C(O)OH$ | $C(O)OCH_2CH_3$ | $OCH(CH_3)_2$ | $NO_2$ | $NO_2$ | H |
| DHP-486 | $C_{10}H_{21}$ | $CH_3$ | $CH_3$ | $C(O)OH$ | $C(O)OCH(CH_3)_2$ | $OCH(CH_3)_2$ | $NO_2$ | $NO_2$ | H |
| DHP-487 | $C_{10}H_{21}$ | $CH_3$ | $CH_3$ | $C(O)OH$ | $C(O)OH$ | $OCH_2CH_3$ | $NO_2$ | $NO_2$ | H |
| DHP-488 | $C_{10}H_{21}$ | $CH_3$ | $CH_3$ | $C(O)OH$ | $C(O)OCH_3$ | $OCH_2CH_3$ | $NO_2$ | $NO_2$ | H |
| DHP-489 | $C_{10}H_{21}$ | $CH_3$ | $CH_3$ | $C(O)OH$ | $C(O)OCH_2CH_3$ | $OCH_2CH_3$ | $NO_2$ | $NO_2$ | H |
| DHP-490 | $C_{10}H_{21}$ | $CH_3$ | $CH_3$ | $C(O)OH$ | $C(O)OCH(CH_3)_2$ | $OCH_2CH_3$ | $NO_2$ | $NO_2$ | H |
| DHP-491 | $C_{10}H_{21}$ | $CH_3$ | $CH_3$ | $C(O)OCH_3$ | $C(O)OH$ | $OCH_3$ | $NO_2$ | $NO_2$ | H |
| DHP-492 | $C_{10}H_{21}$ | $CH_3$ | $CH_3$ | $C(O)OCH_2CH_3$ | $C(O)OH$ | $OCH_3$ | $NO_2$ | $NO_2$ | H |
| DHP-493 | $C_{10}H_{21}$ | $CH_3$ | $CH_3$ | $C(O)OCH(CH_3)_2$ | $C(O)OH$ | $OCH_3$ | $NO_2$ | $NO_2$ | H |
| DHP-494 | $C_{10}H_{21}$ | $CH_3$ | $CH_3$ | $C(O)OCH_3$ | $C(O)OH$ | $OCH(CH_3)_2$ | $NO_2$ | $NO_2$ | H |
| DHP-495 | $C_{10}H_{21}$ | $CH_3$ | $CH_3$ | $C(O)OCH_2CH_3$ | $C(O)OH$ | $OCH(CH_3)_2$ | $NO_2$ | $NO_2$ | H |
| DHP-496 | $C_{10}H_{21}$ | $CH_3$ | $CH_3$ | $C(O)OCH(CH_3)_2$ | $C(O)OH$ | $OCH(CH_3)_2$ | $NO_2$ | $NO_2$ | H |
| DHP-497 | $C_{10}H_{21}$ | $CH_3$ | $CH_3$ | $C(O)OCH_3$ | $C(O)OH$ | $OCH_2CH_3$ | $NO_2$ | $NO_2$ | H |
| DHP-498 | $C_{10}H_{21}$ | $CH_3$ | $CH_3$ | $C(O)OCH_2CH_3$ | $C(O)OH$ | $OCH_2CH_3$ | $NO_2$ | $NO_2$ | H |
| DHP-499 | $C_{10}H_{21}$ | $CH_3$ | $CH_3$ | $C(O)OCH(CH_3)_2$ | $C(O)OH$ | $OCH_2CH_3$ | $NO_2$ | $NO_2$ | H |
| DHP-500 | $C_{10}H_{21}$ | $CH_3$ | $CH_3$ | $C(O)OCH_2CH_3$ | $C(O)OCH_2CH_3$ | $OCH_3$ | $NO_2$ | H | H |
| DHP-501 | $C_{10}H_{21}$ | $CH_3$ | $CH_3$ | $C(O)OCH_2CH_3$ | $C(O)OCH_3$ | $OCH_3$ | $NO_2$ | H | H |
| DHP-502 | $C_{10}H_{21}$ | $CH_3$ | $CH_3$ | $C(O)OCH_2CH_3$ | $C(O)OCH(CH_3)_2$ | $OCH_3$ | $NO_2$ | H | H |
| DHP-503 | $C_{10}H_{21}$ | $CH_3$ | $CH_3$ | $C(O)OCH_2CH_3$ | $C(O)OCH_2CH_3$ | $OCH(CH_3)_2$ | $NO_2$ | H | H |
| DHP-504 | $C_{10}H_{21}$ | $CH_3$ | $CH_3$ | $C(O)OCH_2CH_3$ | $C(O)OCH_3$ | $OCH(CH_3)_2$ | $NO_2$ | H | H |
| DHP-505 | $C_{10}H_{21}$ | $CH_3$ | $CH_3$ | $C(O)OCH_2CH_3$ | $C(O)OCH(CH_3)_2$ | $OCH(CH_3)_2$ | $NO_2$ | H | H |
| DHP-506 | $C_{10}H_{21}$ | $CH_3$ | $CH_3$ | $C(O)OCH_2CH_3$ | $C(O)OCH_2CH_3$ | $OCH_2CH_3$ | $NO_2$ | H | H |

TABLE I-continued

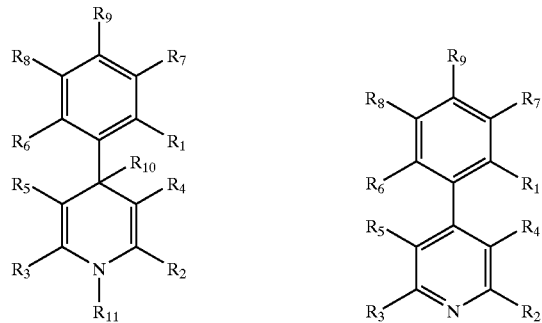

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-507 | $C_{10}H_{21}$ | $CH_3$ | $CH_3$ | $C(O)OCH_2CH_3$ | $C(O)OCH_3$ | $OCH_2CH_3$ | $NO_2$ | H | H |
| DHP-508 | $C_{10}H_{21}$ | $CH_3$ | $CH_3$ | $C(O)OCH_2CH_3$ | $C(O)OCH(CH_3)_2$ | $OCH_2CH_3$ | $NO_2$ | H | H |
| DHP-509 | $C_{10}H_{21}$ | $CH_3$ | $CH_3$ | $C(O)OCH_3$ | $C(O)OCH_3$ | $OCH_3$ | $NO_2$ | H | H |
| DHP-510 | $C_{10}H_{21}$ | $CH_3$ | $CH_3$ | $C(O)OCH_3$ | $C(O)OCH_2CH_3$ | $OCH_3$ | $NO_2$ | H | H |
| DHP-511 | $C_{10}H_{21}$ | $CH_3$ | $CH_3$ | $C(O)OCH_3$ | $C(O)OCH(CH_3)_2$ | $OCH_3$ | $NO_2$ | H | H |
| DHP-512 | $C_{10}H_{21}$ | $CH_3$ | $CH_3$ | $C(O)OCH_3$ | $C(O)OCH_3$ | $OCH(CH_3)_2$ | $NO_2$ | H | H |
| DHP-513 | $C_{10}H_{21}$ | $CH_3$ | $CH_3$ | $C(O)OCH_3$ | $C(O)OCH_2CH_3$ | $OCH(CH_3)_2$ | $NO_2$ | H | H |
| DHP-514 | $C_{10}H_{21}$ | $CH_3$ | $CH_3$ | $C(O)OCH_3$ | $C(O)OCH(CH_3)_2$ | $OCH(CH_3)_2$ | $NO_2$ | H | H |
| DHP-515 | $C_{10}H_{21}$ | $CH_3$ | $CH_3$ | $C(O)OCH_3$ | $C(O)CH_3$ | $OCH_2CH_3$ | $NO_2$ | H | H |
| DHP-516 | $C_{10}H_{21}$ | $CH_3$ | $CH_3$ | $C(O)OCH_3$ | $C(O)OCH_2CH_3$ | $OCH_2CH_3$ | $NO_2$ | H | H |
| DHP-517 | $C_{10}H_{21}$ | $CH_3$ | $CH_3$ | $C(O)OCH_3$ | $C(O)OCH(CH_3)_2$ | $OCH_2CH_3$ | $NO_2$ | H | H |
| DHP-518 | $C_{10}H_{21}$ | $CH_3$ | $CH_3$ | $C(O)OCH(CH_3)_2$ | $C(O)OCH(CH_3)_2$ | $OCH_3$ | $NO_2$ | H | H |
| DHP-519 | $C_{10}H_{21}$ | $CH_3$ | $CH_3$ | $C(O)OCH(CH_3)_2$ | $C(O)OCH_3$ | $OCH_3$ | $NO_2$ | H | H |
| DHP-520 | $C_{10}H_{21}$ | $CH_3$ | $CH_3$ | $C(O)OCH(CH_3)_2$ | $C(O)OCH_2CH_3$ | $OCH_3$ | $NO_2$ | H | H |
| DHP-521 | $C_{10}H_{21}$ | $CH_3$ | $CH_3$ | $C(O)OCH(CH_3)_2$ | $C(O)OCH(CH_3)_2$ | $OCH(CH_3)_2$ | $NO_2$ | H | H |
| DHP-522 | $C_{10}H_{21}$ | $CH_3$ | $CH_3$ | $C(O)OCH(CH_3)_2$ | $C(O)OCH_3$ | $OCH(CH_3)_2$ | $NO_2$ | H | H |
| DHP-523 | $C_{10}H_{21}$ | $CH_3$ | $CH_3$ | $C(O)OCH(CH_3)_2$ | $C(O)OCH_2CH_3$ | $OCH(CH_3)_2$ | $NO_2$ | H | H |
| DHP-524 | $C_{10}H_{21}$ | $CH_3$ | $CH_3$ | $C(O)OCH(CH_3)_2$ | $C(O)OCH(CH_3)_2$ | $OCH_2CH_3$ | $NO_2$ | H | H |
| DHP-525 | $C_{10}H_{21}$ | $CH_3$ | $CH_3$ | $C(O)OCH(CH_3)_2$ | $C(O)OCH_3$ | $OCH_2CH_3$ | $NO_2$ | H | H |
| DHP-526 | $C_{10}H_{21}$ | $CH_3$ | $CH_3$ | $C(O)OCH(CH_3)_2$ | $C(O)OCH_2CH_3$ | $OCH_2CH_3$ | $NO_2$ | H | H |
| DHP-527 | $C_{10}H_{21}$ | $CH_3$ | $CH_3$ | $C(O)OH$ | $C(O)OH$ | $OCH_3$ | $NO_2$ | H | H |
| DHP-528 | $C_{10}H_{21}$ | $CH_3$ | $CH_3$ | $C(O)OH$ | $C(O)OCH_3$ | $OCH_3$ | $NO_2$ | H | H |
| DHP-529 | $C_{10}H_{21}$ | $CH_3$ | $CH_3$ | $C(O)OH$ | $C(O)OCH_2CH_3$ | $OCH_3$ | $NO_2$ | H | H |
| DHP-530 | $C_{10}H_{21}$ | $CH_3$ | $CH_3$ | $C(O)OH$ | $C(O)OCH(CH_3)_2$ | $OCH_3$ | $NO_2$ | H | H |
| DHP-531 | $C_{10}H_{21}$ | $CH_3$ | $CH_3$ | $C(O)OH$ | $C(O)OH$ | $OCH(CH_3)_2$ | $NO_2$ | H | H |
| DHP-532 | $C_{10}H_{21}$ | $CH_3$ | $CH_3$ | $C(O)OH$ | $C(O)OCH_3$ | $OCH(CH_3)_2$ | $NO_2$ | H | H |
| DHP-533 | $C_{10}H_{21}$ | $CH_3$ | $CH_3$ | $C(O)OH$ | $C(O)OCH_2CH_3$ | $OCH(CH_3)_2$ | $NO_2$ | H | H |
| DHP-534 | $C_{10}H_{21}$ | $CH_3$ | $CH_3$ | $C(O)OH$ | $C(O)OCH(CH_3)_2$ | $OCH(CH_3)_2$ | $NO_2$ | H | H |
| DHP-535 | $C_{10}H_{21}$ | $CH_3$ | $CH_3$ | $C(O)OH$ | $C(O)OH$ | $OCH_2CH_3$ | $NO_2$ | H | H |
| DHP-536 | $C_{10}H_{21}$ | $CH_3$ | $CH_3$ | $C(O)OH$ | $C(O)OCH_3$ | $OCH_2CH_3$ | $NO_2$ | H | H |
| DHP-537 | $C_{10}H_{21}$ | $CH_3$ | $CH_3$ | $C(O)OH$ | $C(O)OCH_2CH_3$ | $OCH_2CH_3$ | $NO_2$ | H | H |
| DHP-538 | $C_{10}H_{21}$ | $CH_3$ | $CH_3$ | $C(O)OH$ | $C(O)OCH(CH_3)_2$ | $OCH_2CH_3$ | $NO_2$ | H | H |
| DHP-539 | $C_{10}H_{21}$ | $CH_3$ | $CH_3$ | $C(O)OCH_3$ | $C(O)OH$ | $OCH_3$ | $NO_2$ | H | H |
| DHP-540 | $C_{10}H_{21}$ | $CH_3$ | $CH_3$ | $C(O)OCH_2CH_3$ | $C(O)OH$ | $OCH_3$ | $NO_2$ | H | H |
| DHP-541 | $C_{10}H_{21}$ | $CH_3$ | $CH_3$ | $C(O)OCH(CH_3)_2$ | $C(O)OH$ | $OCH_3$ | $NO_2$ | H | H |
| DHP-542 | $C_{10}H_{21}$ | $CH_3$ | $CH_3$ | $C(O)OCH_3$ | $C(O)OH$ | $OCH(CH_3)_2$ | $NO_2$ | H | H |
| DHP-543 | $C_{10}H_{21}$ | $CH_3$ | $CH_3$ | $C(O)OCH_2CH_3$ | $C(O)OH$ | $OCH(CH_3)_2$ | $NO_2$ | H | H |
| DHP-544 | $C_{10}H_{21}$ | $CH_3$ | $CH_3$ | $C(O)OCH(CH_3)_2$ | $C(O)OH$ | $OCH(CH_3)_2$ | $NO_2$ | H | H |
| DHP-545 | $C_{10}H_{21}$ | $CH_3$ | $CH_3$ | $C(O)OCH_3$ | $C(O)OH$ | $OCH_2CH_3$ | $NO_2$ | H | H |
| DHP-546 | $C_{10}H_{21}$ | $CH_3$ | $CH_3$ | $C(O)OCH_2CH_3$ | $C(O)OH$ | $OCH_2CH_3$ | $NO_2$ | H | H |
| DHP-547 | $C_{10}H_{21}$ | $CH_3$ | $CH_3$ | $C(O)OCH(CH_3)_2$ | $C(O)OH$ | $OCH_2CH_3$ | $NO_2$ | H | H |
| DHP-548 | $C_{10}H_{21}$ | $CH_3$ | $CH_3$ | $C(O)OCH_2CH_3$ | $C(O)OCH_2CH_3$ | $OCH_3$ | H | $NO_2$ | H |
| DHP-549 | $C_{10}H_{21}$ | $CH_3$ | $CH_3$ | $C(O)OCH_2CH_3$ | $C(O)OCH_3$ | $OCH_3$ | H | $NO_2$ | H |
| DHP-550 | $C_{10}H_{21}$ | $CH_3$ | $CH_3$ | $C(O)OCH_2CH_3$ | $C(O)OCH(CH_3)_2$ | $OCH_3$ | H | $NO_2$ | H |
| DHP-551 | $C_{10}H_{21}$ | $CH_3$ | $CH_3$ | $C(O)OCH_2CH_3$ | $C(O)OCH_2CH_3$ | $OCH(CH_3)_2$ | H | $NO_2$ | H |
| DHP-552 | $C_{10}H_{21}$ | $CH_3$ | $CH_3$ | $C(O)OCH_2CH_3$ | $C(O)OCH_3$ | $OCH(CH_3)_2$ | H | $NO_2$ | H |
| DHP-553 | $C_{10}H_{21}$ | $CH_3$ | $CH_3$ | $C(O)OCH_2CH_3$ | $OCH(CH_3)_2$ | $OCH(CH_3)_2$ | H | $NO_2$ | H |
| DHP-554 | $C_{10}H_{21}$ | $CH_3$ | $CH_3$ | $C(O)OCH_2CH_3$ | $C(O)OCH_2CH_3$ | $OCH_2CH_3$ | H | $NO_2$ | H |
| DHP-555 | $C_{10}H_{21}$ | $CH_3$ | $CH_3$ | $C(O)OCH_2CH_3$ | $C(O)OCH_3$ | $OCH_2CH_3$ | H | $NO_2$ | H |
| DHP-556 | $C_{10}H_{21}$ | $CH_3$ | $CH_3$ | $C(O)OCH_2CH_3$ | $C(O)OCH(CH_3)_2$ | $OCH_2CH_3$ | H | $NO_2$ | H |
| DHP-557 | $C_{10}H_{21}$ | $CH_3$ | $CH_3$ | $C(O)OCH_3$ | $C(O)OCH_3$ | $OCH_3$ | H | $NO_2$ | H |
| DHP-558 | $C_{10}H_{21}$ | $CH_3$ | $CH_3$ | $C(O)OCH_3$ | $C(O)OCH_2CH_3$ | $OCH_3$ | H | $NO_2$ | H |
| DHP-559 | $C_{10}H_{21}$ | $CH_3$ | $CH_3$ | $C(O)OCH_3$ | $C(O)OCH(CH_3)_2$ | $OCH_3$ | H | $NO_2$ | H |
| DHP-560 | $C_{10}H_{21}$ | $CH_3$ | $CH_3$ | $C(O)OCH_3$ | $C(O)OCH_3$ | $OCH(CH_3)_2$ | H | $NO_2$ | H |
| DHP-561 | $C_{10}H_{21}$ | $CH_3$ | $CH_3$ | $C(O)OCH_3$ | $C(O)OCH_2CH_3$ | $OCH(CH_3)_2$ | H | $NO_2$ | H |
| DHP-562 | $C_{10}H_{21}$ | $CH_3$ | $CH_3$ | $C(O)OCH_3$ | $C(O)OCH(CH_3)_2$ | $OCH(CH_3)_2$ | H | $NO_2$ | H |
| DHP-563 | $C_{10}H_{21}$ | $CH_3$ | $CH_3$ | $C(O)OCH_3$ | $C(O)OCH_3$ | $OCH_2CH_3$ | H | $NO_2$ | H |
| DHP-564 | $C_{10}H_{21}$ | $CH_3$ | $CH_3$ | $C(O)OCH_3$ | $C(O)OCH_2CH_3$ | $OCH_2CH_3$ | H | $NO_2$ | H |
| DHP-565 | $C_{10}H_{21}$ | $CH_3$ | $CH_3$ | $C(O)OCH_3$ | $C(O)OCH(CH_3)_2$ | $OCH_2CH_3$ | H | $NO_2$ | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-566 | $C_{10}H_{21}$ | $CH_3$ | $CH_3$ | $C(O)OCH(CH_3)_2$ | $C(O)OCH(CH_3)_2$ | $OCH_3$ | H | $NO_2$ | H |
| DHP-567 | $C_{10}H_{21}$ | $CH_3$ | $CH_3$ | $C(O)OCH(CH_3)_2$ | $C(O)OCH_3$ | $OCH_3$ | H | $NO_2$ | H |
| DHP-568 | $C_{10}H_{21}$ | $CH_3$ | $CH_3$ | $C(O)OCH(CH_3)_2$ | $C(O)OCH_2CH_3$ | $OCH_3$ | H | $NO_2$ | H |
| DHP-569 | $C_{10}H_{21}$ | $CH_3$ | $CH_3$ | $C(O)OCH(CH_3)_2$ | $C(O)OCH(CH_3)_2$ | $OCH(CH_3)_2$ | H | $NO_2$ | H |
| DHP-570 | $C_{10}H_{21}$ | $CH_3$ | $CH_3$ | $C(O)OCH(CH_3)_2$ | $C(O)OCH_3$ | $OCH(CH_3)_2$ | H | $NO_2$ | H |
| DHP-571 | $C_{10}H_{21}$ | $CH_3$ | $CH_3$ | $C(O)OCH(CH_3)_2$ | $C(O)OCH_2CH_3$ | $OCH(CH_3)_2$ | H | $NO_2$ | H |
| DHP-572 | $C_{10}H_{21}$ | $CH_3$ | $CH_3$ | $C(O)OCH(CH_3)_2$ | $C(O)OCH(CH_3)_2$ | $OCH_2CH_3$ | H | $NO_2$ | H |
| DHP-573 | $C_{10}H_{21}$ | $CH_3$ | $CH_3$ | $C(O)OCH(CH_3)_2$ | $C(O)OCH_3$ | $OCH_2CH_3$ | H | $NO_2$ | H |
| DHP-574 | $C_{10}H_{21}$ | $CH_3$ | $CH_3$ | $C(O)OCH(CH_3)_2$ | $C(O)OCH_2CH_3$ | $OCH_2CH_3$ | H | $NO_2$ | H |
| DHP-575 | $C_{10}H_{21}$ | $CH_3$ | $CH_3$ | $C(O)OH$ | $C(O)OH$ | $OCH_3$ | H | $NO_2$ | H |
| DHP-576 | $C_{10}H_{21}$ | $CH_3$ | $CH_3$ | $C(O)OH$ | $C(O)OCH_3$ | $OCH_3$ | H | $NO_2$ | H |
| DHP-577 | $C_{10}H_{21}$ | $CH_3$ | $CH_3$ | $C(O)OH$ | $C(O)OCH_2CH_3$ | $OCH_3$ | H | $NO_2$ | H |
| DHP-578 | $C_{10}H_{21}$ | $CH_3$ | $CH_3$ | $C(O)OH$ | $C(O)OCH(CH_3)_2$ | $OCH_3$ | H | $NO_2$ | H |
| DHP-579 | $C_{10}H_{21}$ | $CH_3$ | $CH_3$ | $C(O)OH$ | $C(O)OH$ | $OCH(CH_3)_2$ | H | $NO_2$ | H |
| DHP-580 | $C_{10}H_{21}$ | $CH_3$ | $CH_3$ | $C(O)OH$ | $C(O)OCH_3$ | $OCH(CH_3)_2$ | H | $NO_2$ | H |
| DHP-581 | $C_{10}H_{21}$ | $CH_3$ | $CH_3$ | $C(O)OH$ | $C(O)OCH_2CH_3$ | $OCH(CH_3)_2$ | H | $NO_2$ | H |
| DHP-582 | $C_{10}H_{21}$ | $CH_3$ | $CH_3$ | $C(O)OH$ | $C(O)OCH(CH_3)_2$ | $OCH(CH_3)_2$ | H | $NO_2$ | H |
| DHP-583 | $C_{10}H_{21}$ | $CH_3$ | $CH_3$ | $C(O)OH$ | $C(O)OH$ | $OCH_2CH_3$ | H | $NO_2$ | H |
| DHP-584 | $C_{10}H_{21}$ | $CH_3$ | $CH_3$ | $C(O)OH$ | $C(O)OCH_3$ | $OCH_2CH_3$ | H | $NO_2$ | H |
| DHP-585 | $C_{10}H_{21}$ | $CH_3$ | $CH_3$ | $C(O)OH$ | $C(O)OCH_2CH_3$ | $OCH_2CH_3$ | H | $NO_2$ | H |
| DHP-586 | $C_{10}H_{21}$ | $CH_3$ | $CH_3$ | $C(O)OH$ | $C(O)OCH(CH_3)_2$ | $OCH_2CH_3$ | H | $NO_2$ | H |
| DHP-587 | $C_{10}H_{21}$ | $CH_3$ | $CH_3$ | $C(O)OCH_3$ | $C(O)OH$ | $OCH_3$ | H | $NO_2$ | H |
| DHP-588 | $C_{10}H_{21}$ | $CH_3$ | $CH_3$ | $C(O)OCH_2CH_3$ | $C(O)OH$ | $OCH_3$ | H | $NO_2$ | H |
| DHP-589 | $C_{10}H_{21}$ | $CH_3$ | $CH_3$ | $C(O)OCH(CH_3)_2$ | $C(O)OH$ | $OCH_3$ | H | $NO_2$ | H |
| DHP-590 | $C_{10}H_{21}$ | $CH_3$ | $CH_3$ | $C(O)OCH_3$ | $C(O)OH$ | $OCH(CH_3)_2$ | H | $NO_2$ | H |
| DHP-591 | $C_{10}H_{21}$ | $CH_3$ | $CH_3$ | $C(O)OCH_2CH_3$ | $C(O)OH$ | $OCH(CH_3)_2$ | H | $NO_2$ | H |
| DHP-592 | $C_{10}H_{21}$ | $CH_3$ | $CH_3$ | $C(O)OCH(CH_3)_2$ | $C(O)OH$ | $OCH(CH_3)_2$ | H | $NO_2$ | H |
| DHP-593 | $C_{10}H_{21}$ | $CH_3$ | $CH_3$ | $C(O)OCH_3$ | $C(O)OH$ | $OCH_2CH_3$ | H | $NO_2$ | H |
| DHP-594 | $C_{10}H_{21}$ | $CH_3$ | $CH_3$ | $C(O)OCH_2CH_3$ | $C(O)OH$ | $OCH_2CH_3$ | H | $NO_2$ | H |
| DHP-595 | $C_{10}H_{21}$ | $CH_3$ | $CH_3$ | $C(O)OCH(CH_3)_2$ | $C(O)OH$ | $OCH_2CH_3$ | H | $NO_2$ | H |
| DHP-596 | $C_{10}H_{21}$ | $CH_3$ | $CH_3$ | $C(O)OCH_2CH_3$ | $C(O)OCH_2CH_3$ | $OCH_3$ | H | H | H |
| DHP-597 | $C_{10}H_{21}$ | $CH_3$ | $CH_3$ | $C(O)OCH_2CH_3$ | $C(O)OCH_3$ | $OCH_3$ | H | H | H |
| DHP-598 | $C_{10}H_{21}$ | $CH_3$ | $CH_3$ | $C(O)OCH_2CH_3$ | $C(O)OCH(CH_3)_2$ | $OCH_3$ | H | H | H |
| DHP-599 | $C_{10}H_{21}$ | $CH_3$ | $CH_3$ | $C(O)OCH_2CH_3$ | $C(O)OCH_2CH_3$ | $OCH(CH_3)_2$ | H | H | H |
| DHP-600 | $C_{10}H_{21}$ | $CH_3$ | $CH_3$ | $C(O)OCH_2CH_3$ | $C(O)OCH_3$ | $OCH(CH_3)_2$ | H | H | H |
| DHP-601 | $C_{10}H_{21}$ | $CH_3$ | $CH_3$ | $C(O)OCH_2CH_3$ | $C(O)OCH(CH_3)_2$ | $OCH(CH_3)_2$ | H | H | H |
| DHP-602 | $C_{10}H_{21}$ | $CH_3$ | $CH_3$ | $C(O)OCH_2CH_3$ | $C(O)OCH_2CH_3$ | $OCH_2CH_3$ | H | H | H |
| DHP-603 | $C_{10}H_{21}$ | $CH_3$ | $CH_3$ | $C(O)OCH_2CH_3$ | $C(O)OCH_3$ | $OCH_2CH_3$ | H | H | H |
| DHP-604 | $C_{10}H_{21}$ | $CH_3$ | $CH_3$ | $C(O)OCH_2CH_3$ | $C(O)OCH(CH_3)_2$ | $OCH_2CH_3$ | H | H | H |
| DHP-605 | $C_{10}H_{21}$ | $CH_3$ | $CH_3$ | $C(O)OCH_3$ | $C(O)OCH_3$ | $OCH_3$ | H | H | H |
| DHP-606 | $C_{10}H_{21}$ | $CH_3$ | $CH_3$ | $C(O)OCH_3$ | $C(O)OCH_2CH_3$ | $OCH_3$ | H | H | H |
| DHP-607 | $C_{10}H_{21}$ | $CH_3$ | $CH_3$ | $C(O)OCH_3$ | $C(O)OCH(CH_3)_2$ | $OCH_3$ | H | H | H |
| DHP-608 | $C_{10}H_{21}$ | $CH_3$ | $CH_3$ | $C(O)OCH_3$ | $C(O)OCH_3$ | $OCH(CH_3)_2$ | H | H | H |
| DHP-609 | $C_{10}H_{21}$ | $CH_3$ | $CH_3$ | $C(O)OCH_3$ | $C(O)OCH_2CH_3$ | $OCH(CH_3)_2$ | H | H | H |
| DHP-610 | $C_{10}H_{21}$ | $CH_3$ | $CH_3$ | $C(O)OCH_3$ | $C(O)OCH(CH_3)_2$ | $OCH(CH_3)_2$ | H | H | H |
| DHP-611 | $C_{10}H_{21}$ | $CH_3$ | $CH_3$ | $C(O)OCH_3$ | $C(O)OCH_3$ | $OCH_2CH_3$ | H | H | H |
| DHP-612 | $C_{10}H_{21}$ | $CH_3$ | C | $C(O)OCH_3$ | $C(O)OCH_2CH_3$ | $OCH_2CH_3$ | H | H | H |
| DHP-613 | $C_{10}H_{21}$ | $CH_3$ | C | $C(O)OCH_3$ | $C(O)OCH(CH_3)_2$ | $OCH_2CH_3$ | H | H | H |
| DHP-614 | $C_{10}H_{21}$ | $CH_3$ | C | $C(O)OCH(CH_3)_2$ | $C(O)OCH(CH_3)_2$ | $OCH_3$ | H | H | H |
| DHP-615 | $C_{10}H_{21}$ | $CH_3$ | C | $C(O)OCH(CH_3)_2$ | $C(O)OCH_3$ | $OCH_3$ | H | H | H |
| DHP-616 | $C_{10}H_{21}$ | $CH_3$ | C | $C(O)OCH(CH_3)_2$ | $C(O)OCH_2CH_3$ | $OCH_3$ | H | H | H |
| DHP-617 | $C_{10}H_{21}$ | $CH_3$ | C | $C(O)OCH(CH_3)_2$ | $C(O)OCH(CH_3)_2$ | $OCH(CH_3)_2$ | H | H | H |
| DHP-618 | $C_{10}H_{21}$ | $CH_3$ | C | $C(O)OCH(CH_3)_2$ | $C(O)OCH_3$ | $OCH(CH_3)_2$ | H | H | H |
| DHP-619 | $C_{10}H_{21}$ | $CH_3$ | C | $C(O)OCH(CH_3)_2$ | $C(O)OCH_2CH_3$ | $OCH(CH_3)_2$ | H | H | H |
| DHP-620 | $C_{10}H_{21}$ | $CH_3$ | C | $C(O)OCH(CH_3)_2$ | $C(O)OCH(CH_3)_2$ | $OCH_2CH_3$ | H | H | H |
| DHP-621 | $C_{10}H_{21}$ | $CH_3$ | C | $C(O)OCH(CH_3)_2$ | $C(O)OCH_3$ | $OCH_2CH_3$ | H | H | H |
| DHP-622 | $C_{10}H_{21}$ | $CH_3$ | C | $C(O)OCH(CH_3)_2$ | $C(O)OCH_2CH_3$ | $OCH_2CH_3$ | H | H | H |
| DHP-623 | $C_{10}H_{21}$ | $CH_3$ | C | $C(O)OH$ | $C(O)OH$ | $OCH_3$ | H | H | H |
| DHP-624 | $C_{10}H_{21}$ | $CH_3$ | C | $C(O)OH$ | $C(O)OCH_3$ | $OCH_3$ | H | H | H |

TABLE I-continued

| Comp'd Number | $R_1$ | $R_2$ | $R_3$ | $R_4$ | $R_5$ | $R_6$ | $R_7$ | $R_8$ | $R_9$ |
|---|---|---|---|---|---|---|---|---|---|
| DHP-625 | $C_{10}H_{21}$ | $CH_3$ | C | C(O)OH | $C(O)OCH_2CH_3$ | $OCH_3$ | H | H | H |
| DHP-626 | $C_{10}H_{21}$ | $CH_3$ | C | C(O)OH | $C(O)OCH(CH_3)_2$ | $OCH_3$ | H | H | H |
| DHP-627 | $C_{10}H_{21}$ | $CH_3$ | C | C(O)OH | C(O)OH | $OCH(CH_3)_2$ | H | H | H |
| DHP-628 | $C_{10}H_{21}$ | $CH_3$ | C | C(O)OH | $C(O)OCH_3$ | $OCH(CH_3)_2$ | H | H | H |
| DHP-629 | $C_{10}H_{21}$ | $CH_3$ | C | C(O)OH | $C(O)OCH_2CH_3$ | $OCH(CH_3)_2$ | H | H | H |
| DHP-630 | $C_{10}H_{21}$ | $CH_3$ | C | C(O)OH | $C(O)OCH(CH_3)_2$ | $OCH(CH_3)_2$ | H | H | H |
| DHP-631 | $C_{10}H_{21}$ | $CH_3$ | C | C(O)OH | C(O)OH | $OCH_2CH_3$ | H | H | H |
| DHP-632 | $C_{10}H_{21}$ | $CH_3$ | C | C(O)OH | $C(O)OCH_3$ | $OCH_2CH_3$ | H | H | H |
| DHP-633 | $C_{10}H_{21}$ | $CH_3$ | C | C(O)OH | $C(O)OCH_2CH_3$ | $OCH_2CH_3$ | H | H | H |
| DHP-634 | $C_{10}H_{21}$ | $CH_3$ | C | C(O)OH | $C(O)OCH(CH_3)_2$ | $OCH_2CH_3$ | H | H | H |
| DHP-635 | $C_{10}H_{21}$ | $CH_3$ | C | $C(O)OCH_3$ | C(O)OH | $OCH_3$ | H | H | H |
| DHP-636 | $C_{10}H_{21}$ | $CH_3$ | C | $C(O)OCH_2CH_3$ | C(O)OH | $OCH_3$ | H | H | H |
| DHP-637 | $C_{10}H_{21}$ | $CH_3$ | C | $C(O)OCH(CH_3)_2$ | C(O)OH | $OCH_3$ | H | H | H |
| DHP-638 | $C_{10}H_{21}$ | $CH_3$ | C | $C(O)OCH_3$ | C(O)OH | $OCH(CH_3)_2$ | H | H | H |
| DHP-639 | $C_{10}H_{21}$ | $CH_3$ | C | $C(O)OCH_2CH_3$ | C(O)OH | $OCH(CH_3)_2$ | H | H | H |
| DHP-640 | $C_{10}H_{21}$ | $CH_3$ | C | $C(O)OCH(CH_3)_2$ | C(O)OH | $OCH(CH_3)_2$ | H | H | H |
| DHP-641 | $C_{10}H_{21}$ | $CH_3$ | C | $C(O)OCH_3$ | C(O)OH | $OCH_2CH_3$ | H | H | H |
| DHP-642 | $C_{10}H_{21}$ | $CH_3$ | C | $C(O)OCH_2CH_3$ | C(O)OH | $OCH_2CH_3$ | H | H | H |
| DHP-643 | $C_{10}H_{21}$ | $CH_3$ | C | $C(O)OCH(CH_3)_2$ | C(O)OH | $OCH_2CH_3$ | H | H | H |
| DHP-644 | $C_{10}H_{21}$ | $CH_3$ | $CH_3$ | $CH_2OCH_3$ | $CH_2OCH_3$ | $OCH_3$ | H | H | H |
| DHP-645 | $C_{10}H_{21}$ | $CH_3$ | $CH_3$ | $CH_2OCH_3$ | $CH_2OCH_2CH_3$ | $OCH_3$ | H | H | H |
| DHP-646 | $C_{10}H_{21}$ | $CH_3$ | $CH_3$ | $CH_2OCH_3$ | $CH_2OCH(CH_3)_2$ | $OCH_3$ | H | H | H |
| DHP-647 | $C_{10}H_{21}$ | $CH_3$ | $CH_3$ | $CH_2OCH_2CH_3$ | $CH_2OCH_3$ | $OCH(CH_3)_2$ | H | H | H |
| DHP-648 | $C_{10}H_{21}$ | $CH_3$ | $CH_3$ | $CH_2OCH_2CH_3$ | $CH_2OCH_2CH_3$ | $OCH(CH_3)_2$ | H | H | H |
| DHP-649 | $C_{10}H_{21}$ | $CH_3$ | $CH_3$ | $CH_2OCH_2CH_3$ | $CH_2OCH(CH_3)_2$ | $OCH(CH_3)_2$ | H | H | H |
| DHP-650 | $C_{10}H_{21}$ | $CH_3$ | $CH_3$ | $CH_2OCH(CH_3)_2$ | $CH_2OCH_3$ | $OCH_2CH_3$ | H | H | H |
| DHP-651 | $C_{10}H_{21}$ | $CH_3$ | $CH_3$ | $CH_2OCH(CH_3)_2$ | $CH_2OCH_2CH_3$ | $OCH_2CH_3$ | H | H | H |
| DHP-652 | $C_{10}H_{21}$ | $CH_3$ | $CH_3$ | $CH_2OCH(CH_3)_2$ | $CH_2OCH(CH_3)_2$ | $OCH_2CH_3$ | H | H | H |
| DHP-653 | $C_{15}H_{31}$ | $CH_3$ | $CH_3$ | $C(O)OCH_2CH_2OCH_3$ | $C(O)OCH_2CH_3$ | $OCH_2CH_3$ | H | H | H |
| DHP-654 | $C_{15}H_{31}$ | $CH_3$ | $CH_3$ | $C(O)OCH_2CH_3$ | $C(O)OCH_2CH_3$ | $OCH_2CH_2OCH_3$ | H | H | H |
| DHP-655 | $C_{15}H_{31}$ | $CH_3$ | $CH_3$ | $C(O)OCH_2CH_3$ | $C(O)OCH_2CH_3$ | $OCH_2CH_3$ | H | $NH_2$ | H |

In all of the above compounds, $R_{10} = R_{11} = H$.

*: A = 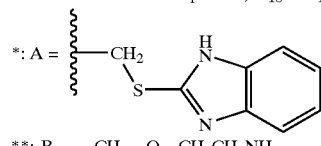

**: B = —$CH_2$—O—$CH_2CH_2NH_2$

: C = 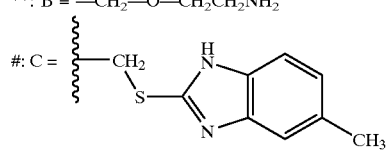

Also contemplated as part of the present invention are four other series of compounds resembling those in Table I. These series are designated by the suffixes -11, -12, -13, and -14. They are identical to DHP-1 through DHP-326 and DHP-653 through DHP-655, except that in each of the -11 series compounds $R_1$ is $C_{11}H_{23}$; in each of the -12 compounds $R_1$ is $C_{12}H_{25}$; in each of the -13 series compounds $R_1$ is $C_{13}H_{27}$; and in each of the -14 compounds $R_1$ is $C_{14}H_{29}$. Thus, the inventors specifically contemplate each of DHP-1-11 through DHP-326-11 and DHP-653-11 through DHP-655-11; DHP-1-12 through DHP-326-12 and DHP-653-12 through DHP-655-12; DHP-1-13 through DHP-326-13 and DHP-653-13 through DHP-655-13; and DHP-1-14 through DHP-326-14 and DHP-653-14 through DHP-655-14, as explicitly as if the exact formula of each was set forth herein individually.

II. Methods of Treatment

In another aspect, the invention relates to a method of modulating the activity of a calcium channel in a cell comprising the step of contacting said cell with a compound of Formula I, as described above. The calcium channel being modulated may be a low voltage activated calcium channel or a high voltage activated calcium channel.

In a further aspect, the invention relates to a method of treating a disease associated with a cellular calcium channel comprising identifying a subject in need of such treatment, and administering to the subject a therapeutically effective amount of a compound of Formula I, as described above. In certain embodiments, the subject may be a mammal. The mammal may be selected from the group consisting of mice, rats, rabbits, guinea pigs, dogs, cats, sheep, goats, cows, primates, such as monkeys, chimpanzees, and apes, and humans. In some embodiments, the subject is a human. Embodiments of the invention include those in which the disease to be treated is a cardiovascular disease or a neurological disorder.

III. Pharmaceutical Compositions

In another aspect, the invention relates to a pharmaceutical composition comprising a compound of Formula I or II, as described above, and a physiologically acceptable carrier, diluent, or excipient, or a combination thereof.

The term "pharmaceutical composition" refers to a mixture of a compound of the invention with other chemical components, such as carriers, diluents or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a nontoxic chemical compound that facilitates the incorporation of a compound into cells or tissues. For example, human serum albumin (HSA) is a commonly utilized carrier as it facilitates the uptake of many organic compounds into the cells or tissues of an organism.

The term "diluent" defines chemical compounds that are used to dilute the compound of interest prior to delivery. Diluents can also be used to stabilize compounds because they can provide a more stable environment. Salts dissolved in buffered solutions (providing pH control) are utilized as diluents in the art. One commonly used buffered solution is phosphate buffered saline. It is a buffer found naturally in the blood system. Since buffer salts can control the pH of a solution at low concentrations, a buffered diluent rarely modifies the biological activity of a compound.

The term "physiologically acceptable" defines a carrier or diluent that does not abrogate the biological activity or properties of the compound, and is nontoxic.

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," 20th ed. Edited by Alfonso Gennaro, 2000.

a) Routes of Administration

Suitable routes of administration may, for example, include oral, rectal, transmucosal, pulmonary, ophthalmic or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into an organ, often in a depot sustained release formulation. Furthermore, one may administer the drug in a targeted drug delivery system, for example, in a liposome coated with organ-specific antibody. The liposomes will be targeted to and taken up selectively by the organ.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or compression processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For intravenous injections, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For other parenteral injections, the agents of the invention may be formulated in aqueous or nonaqueous solutions, preferably with physiologically compatible buffers or excipients. Such excipients are generally known in the art.

For oral administration, the compounds can be formulated readily by combining the active compounds with pharmaceutically acceptable carriers or excipients well known in the art. Such carriers enable the compounds of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be a 10% ethanol, 10% polyethylene glycol 300, 10% polyethylene glycol 40 castor oil (PEG-40 castor oil) with 70% aqueous solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of PEG-40 castor oil, the fraction size of polyethylene glycol 300 may be varied; other biocompatible polymers may replace polyethylene glycol, e.g., polyvinyl pyrrolidone; and other sugars or polysaccharides maybe included in the aqueous solution.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient.

The daily dosage regimen for an adult human patient may be, for example, an oral dose of between 0.1 mg and 500 mg, preferably between 1 mg and 250 mg, e.g. 5 to 200 mg or an intravenous, subcutaneous, or intramuscular dose of between 0.01 mg and 100 mg, preferably between 0.1 mg and 60 mg, e.g. 1 to 40 mg of the compound of the formula (I) or a pharmaceutically acceptable salt thereof calculated as the free base, the compound being administered 1 to 4 times per day. Alternatively the compounds of the invention may be administered by continuous intravenous infusion, preferably at a dose of up to 400 mg per day. Thus, the total daily dosage by oral administration will be in the range 1 to 2000 mg and the total daily dosage by parenteral administration will be in the range 0.1 to 400 mg. Suitably the compounds will be administered for a period of continuous therapy, for example for a week or more.

Dosage amount and interval may be adjusted individually to provide plasma levels of the active moiety which are sufficient to maintain the modulating effects, or minimal effective concentration (MEC). The MEC will vary for each compound but can be estimated from in vitro data; e.g., the concentration necessary to achieve 50–90% of calcium channel blockage, using the assays known in the art. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

IV. Synthesis of the Compounds of the Invention

Some of the compounds of the present invention can be synthesized using the general synthetic procedures set forth below, in Schemes 1–12.

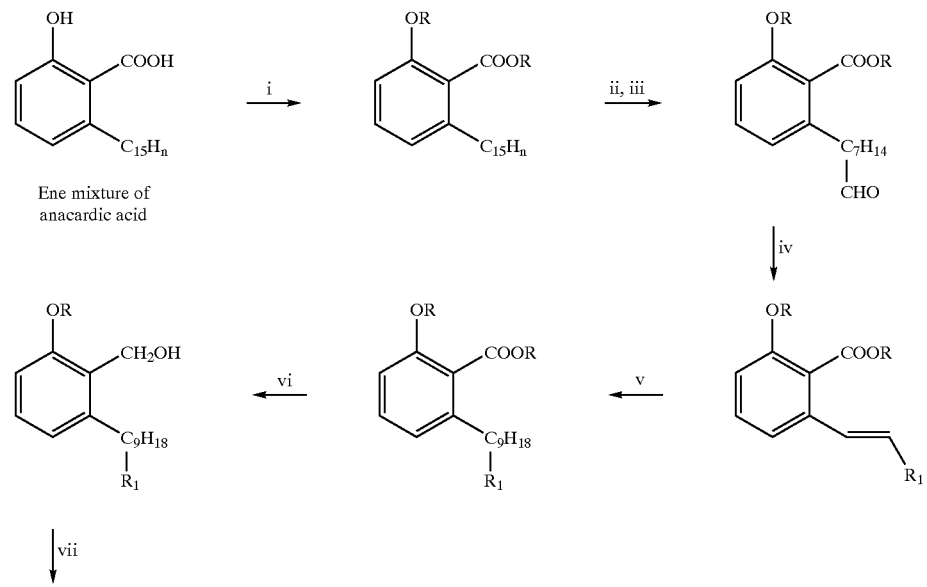

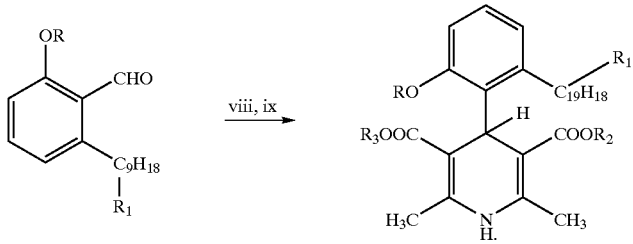

Reagents: (i) $R_2SO_4/K_2CO_3$, acetone, reflux 3 h; (ii) $H_2O_2$, HCOOH; (iii) $NaIO_4$, THF-water, 5° C., 2 h; (iv) $R_1CH=PPh_3$, potassium-t-butoxide, dichloromethane, 12 h; (v) Pd/C, $H_2$, methanol, 3 h; (vi) $LiAlH_4$, tetrahydrofuran, reflux, 3 h; (vii) PCC, dichloromethane, rt. 3 h; (viii) $CH_3COCH_2COOR_2$/piperidine, acetic acid, n-butanol, rt. 3 h; (ix) $(CH_3)(NH_2)C=CH(COOR_3)$, n-butanol, reflux, 10 h.

Scheme 2

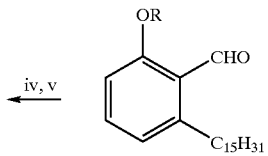

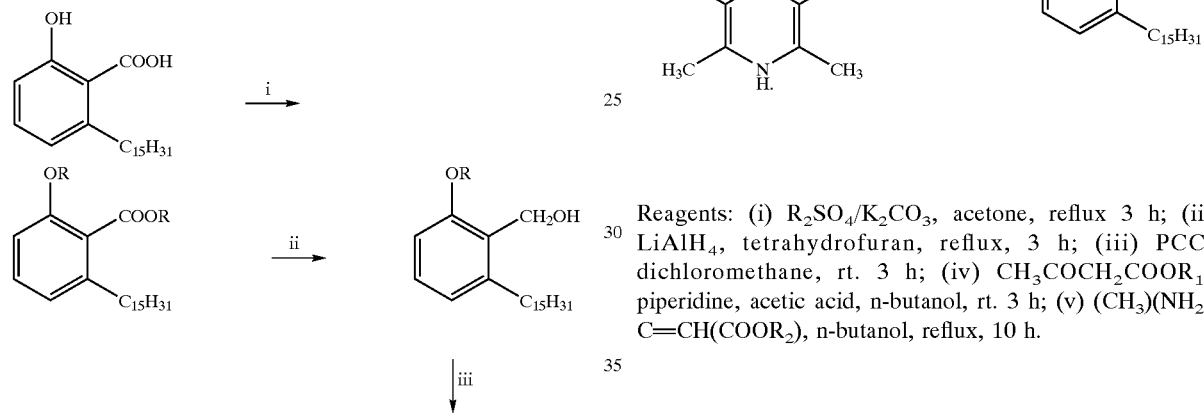

Reagents: (i) $R_2SO_4/K_2CO_3$, acetone, reflux 3 h; (ii) $LiAlH_4$, tetrahydrofuran, reflux, 3 h; (iii) PCC, dichloromethane, rt. 3 h; (iv) $CH_3COCH_2COOR_1$/piperidine, acetic acid, n-butanol, rt. 3 h; (v) $(CH_3)(NH_2)C=CH(COOR_2)$, n-butanol, reflux, 10 h.

Scheme 3

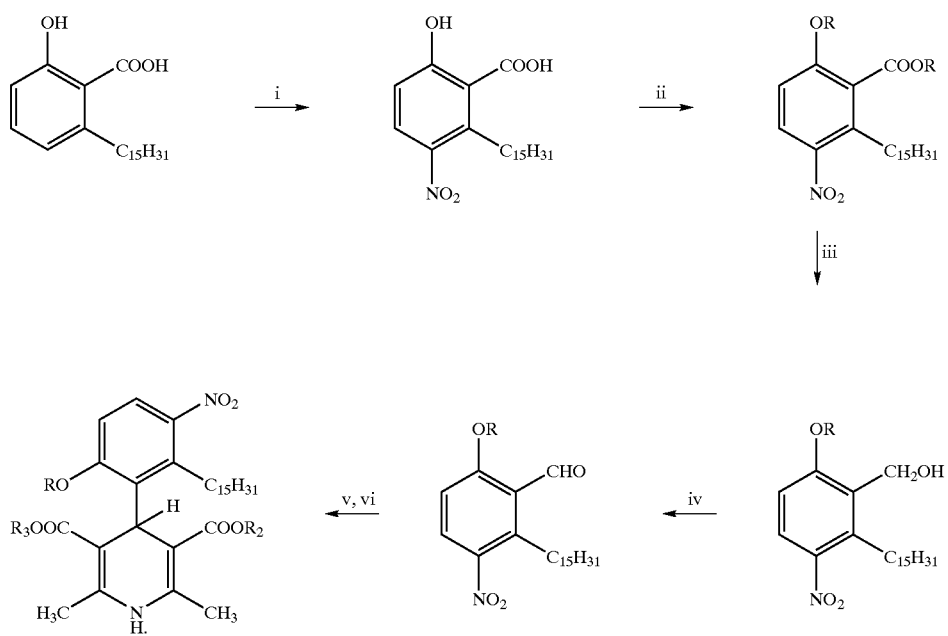

Reagents: (i) $H_2SO_4/HNO_3$, 5° C., 2 h; (ii) $R_2SO_4/K_2CO_3$, acetone, reflux 3 h; (iii) $LiAlH_4$, tetrahydrofuran, reflux, 3 h; (iv) PCC, dichloromethane, rt. 3 h; (v) $CH_3COCH_2COOR_1$/piperidine, acetic acid, n-butanol, rt. 3 h; (vi) $(CH_3)(NH_2)C=CH(COOR_2)$, n-butanol, reflux, 10 h.

Scheme 4

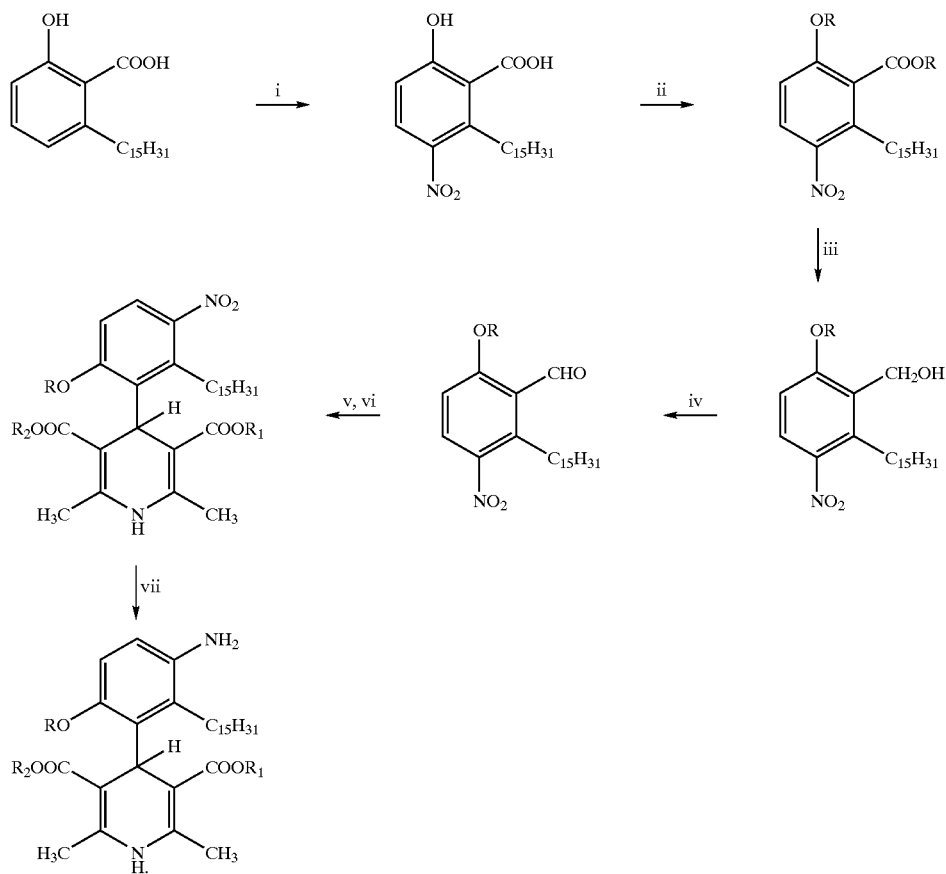

Reagents: (i) $H_2SO_4/HNO_3$, 5° C., 2 h; (ii) $R_2SO_4/K_2CO_3$, acetone, reflux 3 h; (iii) $LiAlH_4$, tetrahydrofuran, reflux, 3 h; (iv) PCC, dichloromethane, rt. 3 h; (v) $CH_3COCH_2COOR_1$/piperidine, acetic acid, n-butanol, rt. 3 h; (vi) $(CH_3)(NH_2)C=CH(COOR_2)$, n-butanol, reflux, 10 h; (vii) Sn, Conc. HCl.

Scheme 5

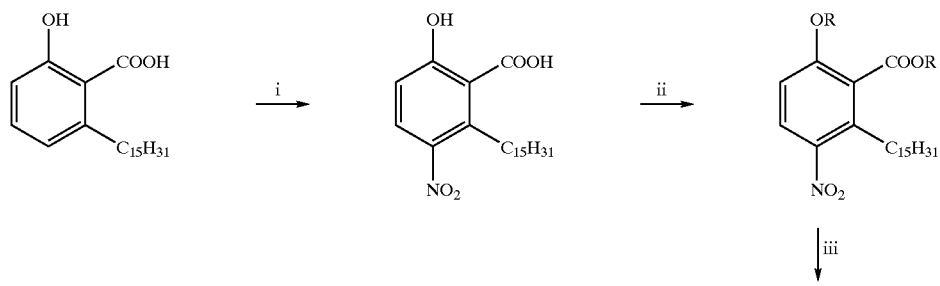

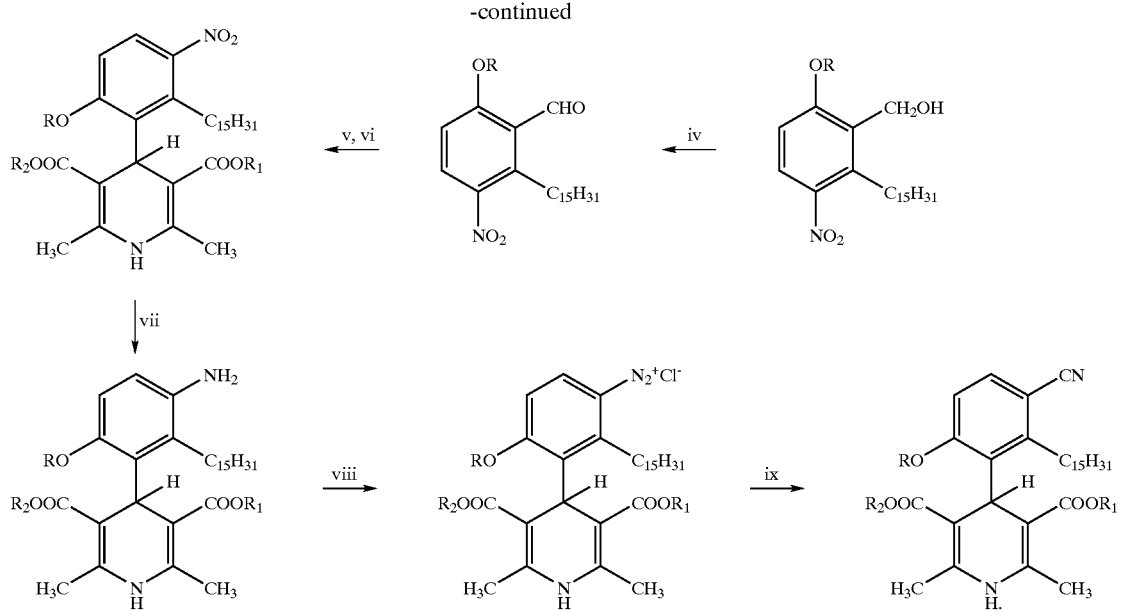
Reagents: (i) $H_2SO_4/HNO_3$, 5° C., 2 h; (ii) $R_2SO_4/K_2CO_3$, acetone, reflux 3 h; (iii) $LiAlH_4$, tetrahydrofuran, reflux, 3 h; (iv) PCC, dichloromethane, rt. 3 h; (v) $CH_3COCH_2COOR_1$/piperidine, acetic acid, n-butanol, rt. 3 h; (vi) $(CH_3)(NH_2)C=CH(COOR_2)$, n-butanol, reflux, 10 h; (vii) Sn, Conc. HCl; (viii) $NaNO_2$/Conc. HCl, 2 h; (ix) Cu(I)CN, dichloromethane, 3 h.
Scheme 6
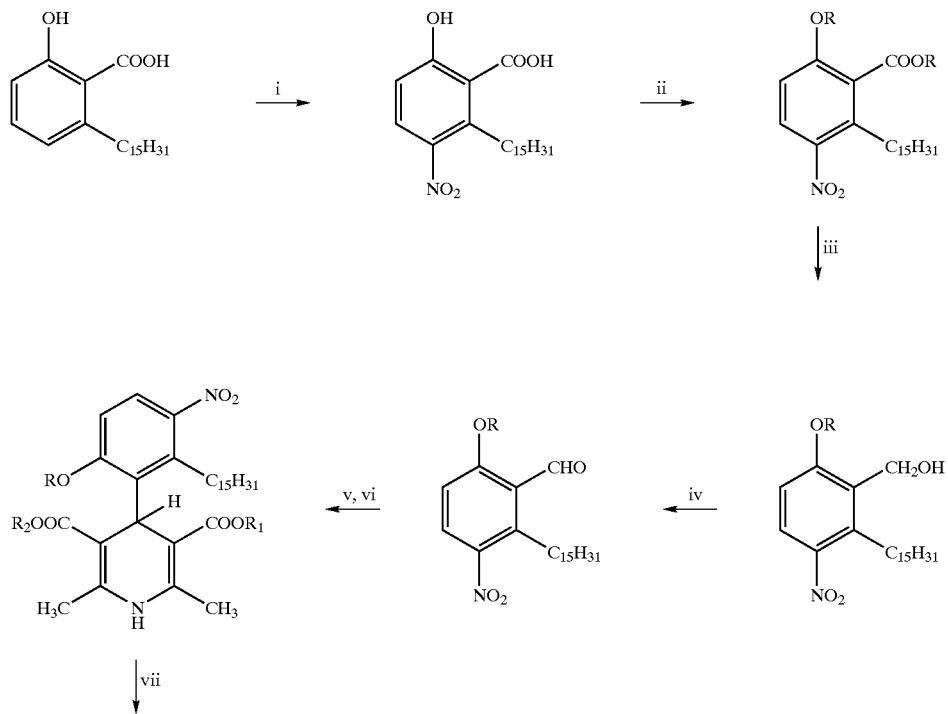

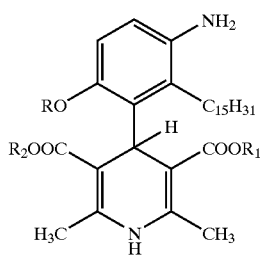
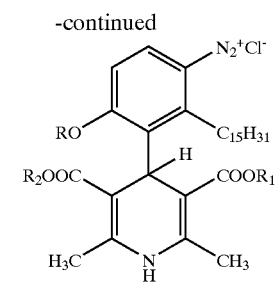
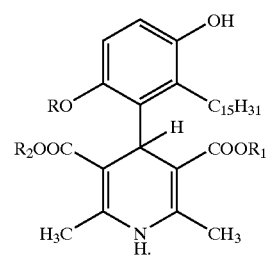

Reagents: (i) $H_2SO_4/HNO_3$, 5° C., 2 h; (ii) $R_2SO_4/K_2CO_3$, acetone, reflux 3 h; (iii) $LiAlH_4$, tetrahydrofuran, reflux, 3 h; (iv) PCC, dichloromethane, rt. 3 h; (v) $CH_3COCH_2COOR_1$/ piperidine, acetic acid, n-butanol, rt. 3 h; (vi) $(CH_3)(NH_2)C=CH(COOR_2)$, n-butanol, reflux, 10 h; (vii) Sn, Conc. HCl; (viii) $NaNO_2$/Conc. HCl, 2 h; (ix) $H_2O$ 30 min.

Scheme 7

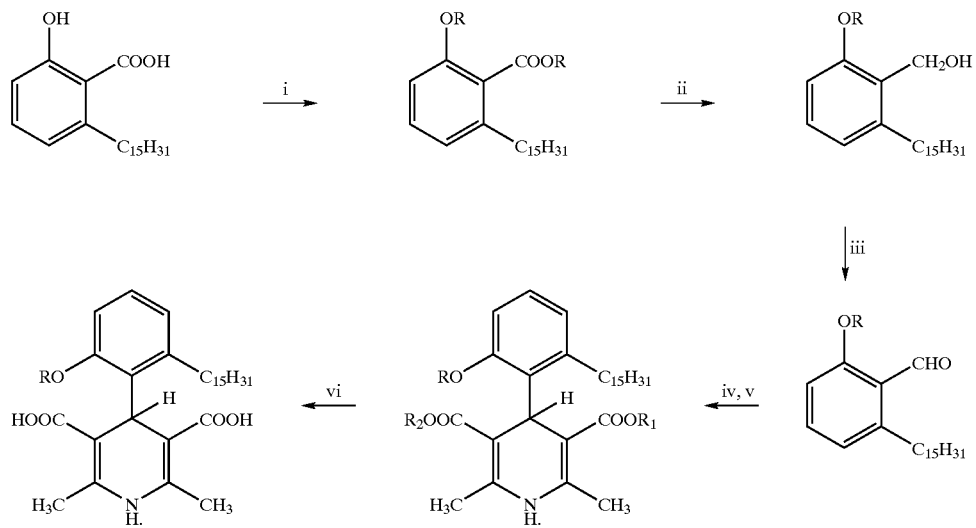

Reagents: (i) $R_2SO_4/K_2CO_3$, acetone, reflux 3 h; (ii) $LiAlH_4$, tetrahydrofuran, reflux, 3 h; (iii) PCC, dichloromethane, rt. 3 h; (iv) $CH_3COCH_2COOR_1$/ piperidine, acetic acid, n-butanol, rt. 3 h; (v) $(CH_3)(NH_2)C=CH(COOR_2)$, n-butanol, reflux, 10 h; (vi) NaOH, methanol, reflux, 4 h.

Scheme 8

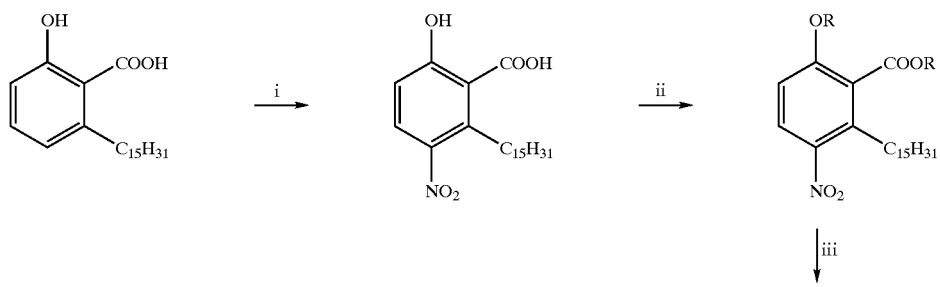

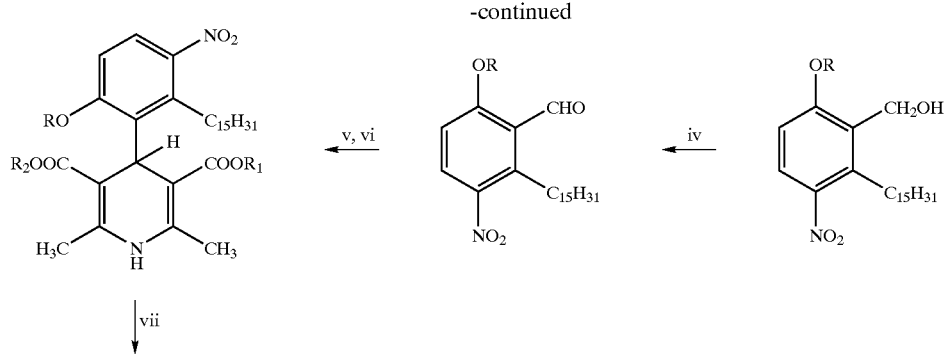

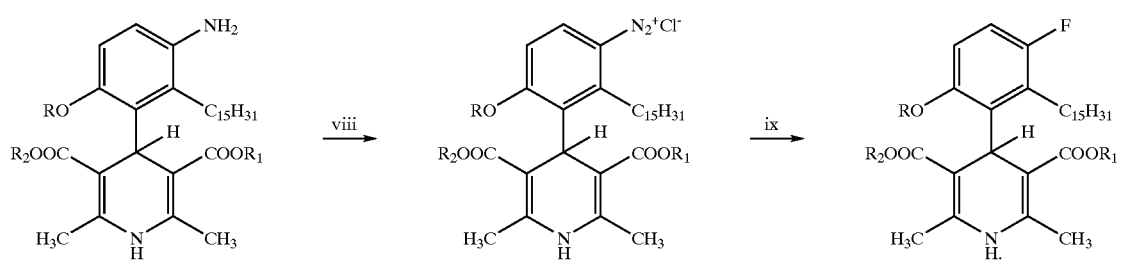

Reagents: (i) H$_2$SO$_4$/HNO$_3$, 5° C., 2 h; (ii) R$_2$SO$_4$/K$_2$CO$_3$, acetone, reflux 3 h; (iii) LiAlH$_4$, tetrahydrofuran, reflux, 3 h; (iv) PCC, dichloromethane, rt. 3 h; (v) CH$_3$COCH$_2$COOR$_1$/piperidine, acetic acid, n-butanol, rt. 3 h; (vi) (CH$_3$)(NH$_2$)C=CH(COOR$_2$), n-butanol, reflux, 10 h; (vii) Sn, Conc. HCl; (viii) NaNO$_2$/Conc. HCl, 2 h; (ix) SbF$_6$, dichloromethane, 3 h.

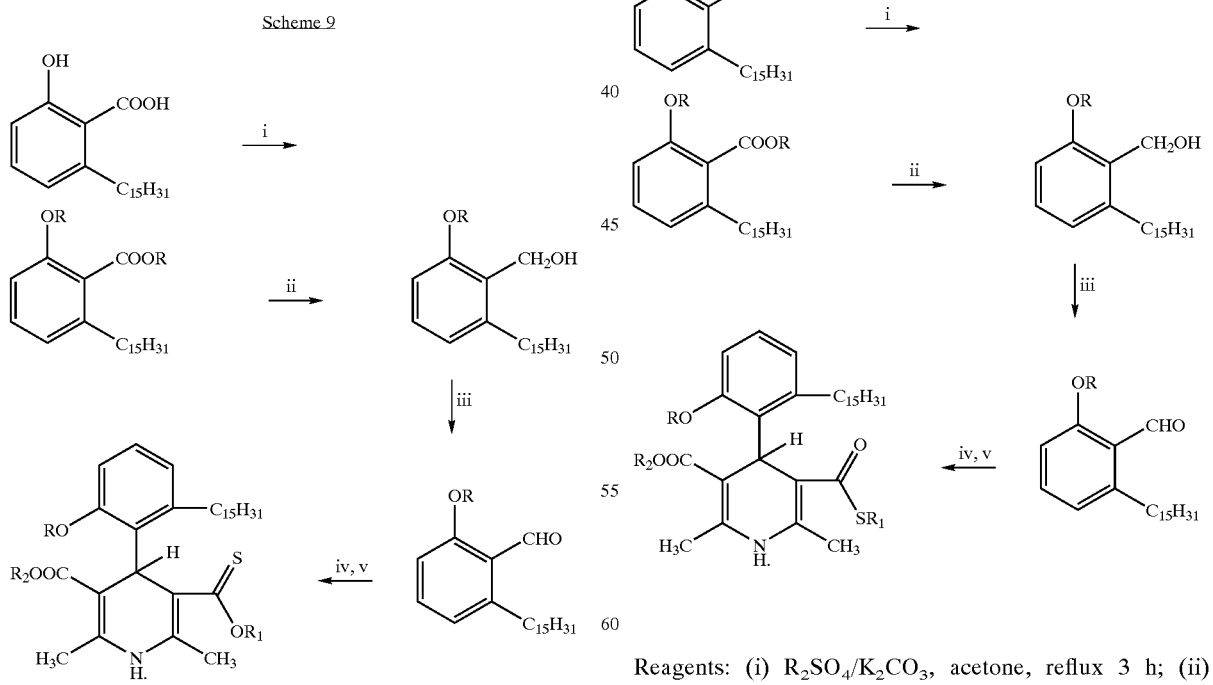

Scheme 9

Reagents: (i) R$_2$SO$_4$/K$_2$CO$_3$, acetone, reflux 3 h; (ii) LiAlH$_4$, tetrahydrofuran, reflux, 3 h; (iii) PCC, dichloromethane, rt. 3 h; (iv) CH$_3$COCH$_2$C(S)OR$_1$/piperidine, acetic acid, n-butanol, rt. 3 h; (v) (CH$_3$)(NH$_2$)C=CH(COOR$_2$), n-butanol, reflux, 10 h.

Scheme 10

Reagents: (i) R$_2$SO$_4$/K$_2$CO$_3$, acetone, reflux 3 h; (ii) LiAlH$_4$, tetrahydrofuran, reflux, 3 h; (iii) PCC, dichloromethane, rt. 3 h; (iv) CH$_3$COCH$_2$C(O)SR$_1$/piperidine, acetic acid, n-butanol, rt. 3 h; (v) (CH$_3$)(NH$_2$)C=CH(COOR$_2$), n-butanol, reflux, 10 h.

Scheme 11
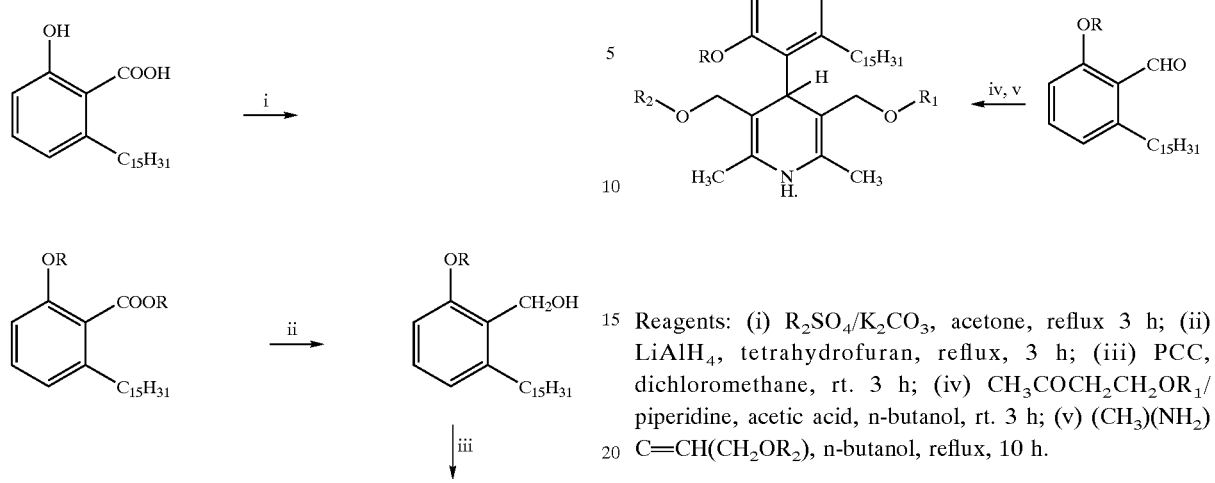
Reagents: (i) R$_2$SO$_4$/K$_2$CO$_3$, acetone, reflux 3 h; (ii) LiAlH$_4$, tetrahydrofuran, reflux, 3 h; (iii) PCC, dichloromethane, rt. 3 h; (iv) CH$_3$COCH$_2$CH$_2$OR$_1$/piperidine, acetic acid, n-butanol, rt. 3 h; (v) (CH$_3$)(NH$_2$)C=CH(CH$_2$OR$_2$), n-butanol, reflux, 10 h.
Scheme 12
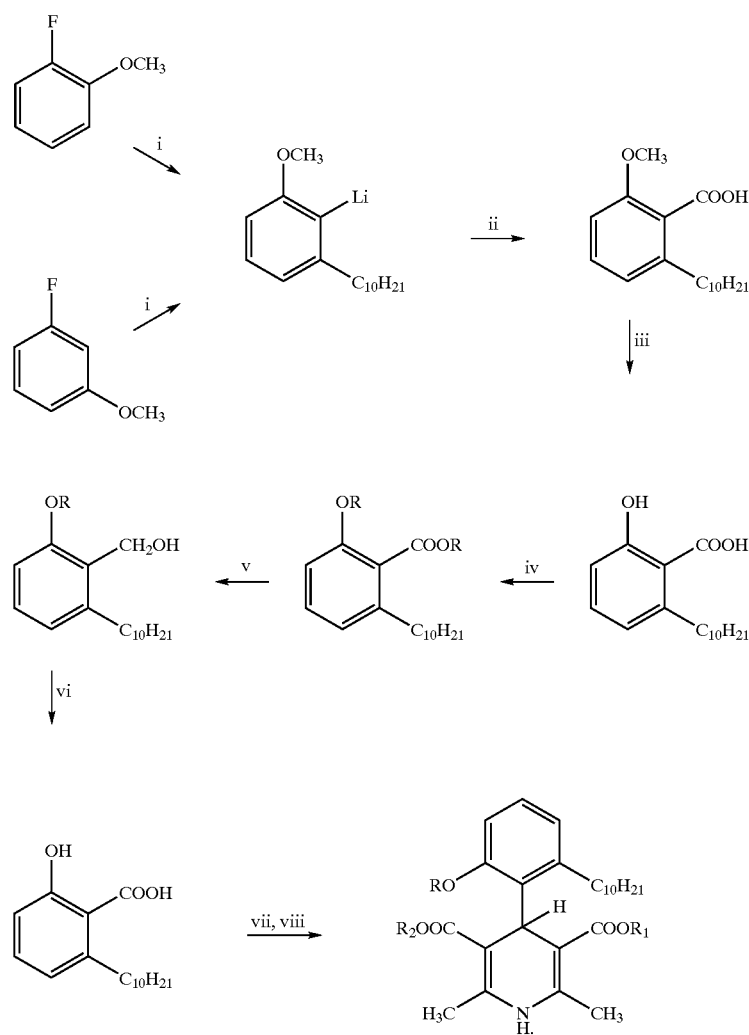

Reagents: (i) 2 $C_{10}H_{21}Li$, THF, 3 h; (ii) $CO_2$, 4 h; (iii) HI/P, dichloromethane, reflux, 6 h; (iv) $R_2SO_4/K_2CO_3$, acetone, reflux 3 h; (v) $LiAlH_4$, tetrahydrofuran, reflux, 3 h; (vi) PCC, dichloromethane, rt. 3 h; (vii) $CH_3COCH_2COOR_1$/ piperidine, acetic acid, n-butanol, rt. 3 h; (viii) $(CH_3)(NH_2)$ $C=CH(COOR_2)$, n-butanol, reflux, 10 h.

Certain of the compounds of the general Formula I or II were prepared by the well-known Hantzsch dihydropyridine synthesis. In this method appropriate aldehyde was condensed with an appropriate beta keto esters like methyl acetoacetate, ethyl acetoacetate, isopropyl acetoacetate, ethyl 4-chloro acetoacetate and like, in inert solvent such as methanol, ethanol, isopropyl alcohol, n-butanol, an ether solvent such as 1,2-dimethoxyethane or tetrahydrofuran (THF), an amide solvent such as dimethyl formamide (DMF) or N-methylpyrrolidone, a sulfoxide solvent such as dimethyl sulfoxide (DMSO) or sulfolane, an aromatic hydrocarbon solvent such as benzene, toluene or xylene in presence of piperidine and acetic acid. If required, the knoevenegal product was purified by column chromatography and reacted with appropriate amino crotonate like methyl-3-amino crotonate, ethyl 3-amino crotonate, isopropyl 3-amino crotonate. The reaction is usually conducted at temperature from room temperature to 200° C., preferably from 60 to 140° C., for from 1–100 hours, preferably from 6 to 40 hours. The corresponding Hantzsch product was purified by column chromatography using silicagel (100–200 mesh) and/or crystallised using appropriate organic solvents like hexane, petroleum ether (40–60° C.), ethanol etc. Substrates like 2-mercapto benzimidazole, (5-methyl)2-mercapto benzimidazole, 2-amino ethanol and like as mentioned in claim 1 were used for substitutions on dihydropyridine ring.

For the processes mentioned above, any desired ratio of the substances participating in the reaction can be used. In general, however, the process is carried out with molar amounts of the reactants.

The synthesis of compounds includes enantiomerically pure forms obtained by methods such as, by separating diastereomer mixtures of the compounds of the general Formula I or II, from an enantiomerically pure chiral alcohol, by a customary method, subsequently preparing the enantiomerically pure carboxylic acids and/or any methods used for separation of enantiomers, for example, methods discussed by S. Goldmann and J. Stoltefuss [S. Goldmann and J. Stoltefuss "1,4-*Dihydropyridine: Effects of chirality and conformation on the calcium antagonist and calcium agonist activities*" Angewandte Chemie International Edition (*English*) 30, 1559–1578 (1991)].

As indicated above, the compounds and compositions of this invention are useful as calcium entry blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory systems; (vi) as antihypercholestorolemic and antilipidemic agents; (vii) protection of the ischemic myocardium; (viii) inhibit irritable bowel syndrome and esophagel spasm; (ix) inhibit migraine; and, (x) epilepsy. Some of are also useful cardiotonic agents. This list also includes any cardiovascular problems related to low voltage activated (LVA) and high voltage activated (HVA) calcium channels.

The representative compounds of the present invention might inhibit vascular calcium contraction, reduce cardiac contractile force, inhibit calcium mediated tracheal contraction, inhibit calcium uptake in pituitary cells, or displace tritiated nitrendipine from membrane.

EXAMPLES

The examples below are illustrative of some of the embodiments of the invention only and should not be construed to limit the scope of the claims.

Example 1

Extraction of ene mixture of anacardic acid (2-hydroxy-6-pentadecyl benzoic acid) from solvent extracted CNSL Commercially available solvent extracted cashew nut shell liquid (CNSL) (100 g) was dissolved in 5% aqueous methanol (600 mL). To the methanolic solution was added activated charcoal (20 g), stirred for 15 minutes, then filtered over celite bed to remove any insoluble material. The clear filtrate was transferred into three neck round bottom flask fitted with a double surface reflux condenser and mechanical stirrer. Calcium hydroxide (50 g) was added in portions at room temperature and the reaction mass temperature was raised to 50° C. and allowed to maintain for 3 hrs. Progress of the reaction was monitored by thin layer chromatography (TLC) using hexane-ethyl acetate (8:2) as mobile phase. After the completion of reaction, the precipitated calcium anacardate was filtered and washed thoroughly with methanol (200 mL). The resultant cake was dried under vacuum at 45–50° C. for 2 hrs to yield calcium anacardate (120 g).

Dry cake (120 g) was suspended in distilled water (440 mL), added concentrated hydrochloric acid (33%, 60 mL) and stirred for 1 hr. Resultant solution was extracted with ethylacetate (2×150 mL). The combined organic layer was washed with distilled water (2×500 mL), dried over anhydrous sodium sulfate and concentrated under reduced pressure to yield an ene mixture of anacardic acid. (Yield: 60 g).

Example 2

Hydrogenation of Anacardic Acid Ene Mixture

Anacardic acid ene mixture (30 g,) was dissolved in methanol (120 ml). 5% Pd/C (0.75 g, 2.5%) was added slowly and this solution were transferred to 250-mL hydrogenation flask. Initially the solution was flushed with nitrogen and then with hydrogen. Hydrogenation was carried out with 2.5 $kg/cm^2$ hydrogen gas pressure for 2 hrs. Then the solution was filtered through a celite bed to obtain catalyst free solution. This was evaporated under vacuum to get crude saturated anacardic acid. It was then recrystallised from petroleum ether (Yield: 25 g).

Example 3

Synthesis of ethyl 2-ethoxy-6-pentadecyl-benzoate

Anacardic acid (10.11 g, 29 mmol) was dissolved in acetone (60 mL) and potassium carbonate (4.0 g, 29 mmol) was charged. Diethyl sulfate (8.93 g, 58 mmol) was added slowly under stirring. This solution was then transferred to a three-neck flask fitted with a reflux condenser and mechanical stirrer, and refluxed for 4 hrs. Progress of reaction was monitored by TLC (mobile phase:Hexane:EtOAc 9:1). After completion of reaction, it was filtered and acetone was evaporated under vacuum. Crude product was dissolved in dichloromethane (50 mL) and washed with water (2×50 mL), 5% sodium bicarbonate solution (50 mL), saturated brine (50 mL) and finally with distilled water (2×50 mL). The organic layer was dried over anhydrous sodium sulphate, and evaporated under vacuum to give ethyl 2-ethoxy-6-pentadecyl-benzoate as oil. This was then dissolved in minimum amount of petroleum ether (40–60° C.) and cooled to 0° C. to give light brownish crystals (Yield: 12 g).

Example 4

Synthesis of isopropyl 2-isopropoxy-6-pentadecyl-benzoate

Anacardic acid (10.11 g, 29 mmol) was dissolved in isobutyl methyl ketone (60 mL). To this, finely powdered potassium carbonate (4.0 g, 29 mmol) and benzyl tributyl ammonium chloride (1 g) was added. Slowly, isopropyl bromide (7.13 g, 58 mmol) was added and refluxed for 8 hrs. TLC was checked in hexane:EtOAc (9:1). Solution was filtered and evaporated under vacuum to give a viscous liquid. Crude product was dissolved in dichloromethane (50 mL) and washed with water (2×50 mL), 5% sodium bicarbonate solution (50 mL), saturated brine (50 mL) and finally with water (2×50 mL). The organic layer was dried over anhydrous sodium sulfate and evaporated under vacuum to give isopropyl 2-isopropoxy-6-pentadecyl-benzoate as oil (Yield: 12 g).

Example 5

Synthesis of 2-ethoxy-6-pentadecyl-benzyl alcohol

Ethyl 2-ethoxy-6-pentadecyl-benzoate (10.9 g, 27 mmol) was dissolved in dry tetrahydrofuran (60 mL). This solution was transferred to dry 250 mL three neck round bottom flask fitted with reflux condenser, mechanical stirrer and it was maintained under nitrogen atmosphere through out the reaction. To this lithium aluminum hydride (2.04 g, 54 mmol) was added slowly. Reaction was highly exothermic. After addition the solution was slowly brought to the reflux temperature and maintained at that temperature for about two hours and TLC was checked in hexane:EtOAc (8:2). After completion of reaction, excess lithium aluminium hydride was decomposed by drop-wise addition of ethylacetate (80 mL). To this 5 M HCl (100 mL) was added and organic layer was separated, dried over anhydrous sodium sulphate, concentrated under vacuum to give a light brownish solid. This was recrystallised from petroleum ether (40–60° C.) to give white solid. Yield: 8 g.

Example 6

Synthesis of 2-ethoxy-6-pentadecyl-benzaldehyde

To a 250 mL round bottom flask fitted with a reflux condenser, was added pyridinium chloro chromate (PCC) (16.1 g, 75 mmol) in anhydrous dichloromethane (100 mL). 2-Ethoxy-6-pentadecyl-benzyl alcohol (18.1 g, 50 mmol) in dichloromethane (10 mL) was added in one portion to the magnetically stirred solution. After 1.5 hr dry ether (100 mL) was added and the supernatant decanted from the black gum. The insoluble residue was washed thoroughly with diethyl ether (3×25 mL), where upon it became black granular solid. The organic solution was passed through a short pad of celite, and the solvent was removed by distillation to obtain brownish low melting solid (Yield: 15 g).

Example 7

Synthesis of diethyl 1,4-dihydro-4-(2'-ethoxy-6'-pentadecyl phenyl)-2,6-dimethyl-3,5-pyridine dicarboxylate (DHP-4)

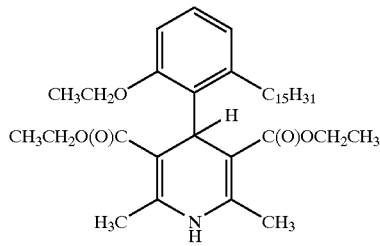

2-Ethoxy-6-pentadecyl benzaldehyde (3 g, 8.3 mmol) and ethyl acetoacetate (1.08 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give diethyl 1,4-dihydro-4-(2'-ethoxy-6'-pentadecyl phenyl)-2,6-dimethyl-3,5-pyridine dicarboxylate as white powder.

Example 8

Synthesis of ethyl isopropyl 1,4-dihydro-4-(2'-ethoxy-6'-pentadecylphenyl)-2,6-dimethyl-3,5-pyridine dicarboxylate (DHP-12)

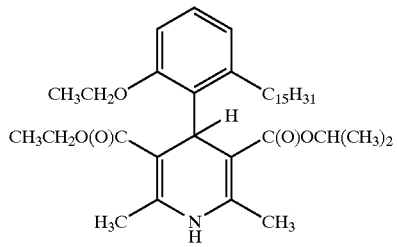

2-Ethoxy-6-pentadecyl benzaldehyde (3 g, 8.3 mmol) and isopropyl acetoacetate (1.19 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silica gel (100–200 mesh) with hexane:EtOAc (94:6) solvent system to give ethyl isopropyl 1,4-dihydro-4-(2'-ethoxy-6'-pentadecylphenyl)-2,6-dimethyl-3,5-pyridine dicarboxylate as viscous liquid.

Example 9

Synthesis of dimethyl 1,4-dihydro-4-(2'-isopropoxy-6'-pentadecylphenyl)-2,6-dimethyl-3,5-pyridine dicarboxylate (DHP-5)

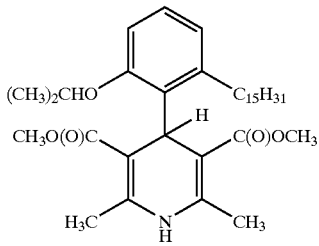

2-Isopropoxy-6-pentadecyl benzaldehyde (3.1 g, 8.3 mmol) and methyl acetoacetate (0.96 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. methyl-3-amino crotonate (0.97 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give dimethyl 1,4-dihydro-4-(2'-isopropoxy-6'-pentadecylphenyl)-2,6-dimethyl-3,5-pyridine dicarboxylate as viscous liquid.

Example 10

Synthesis of diethyl 1,4-dihydro-4-(2'-ethoxy-6'-pentadecyl phenyl)-6-methyl-2-(2'-mercapto-1'H-benzimidazolyl) methyl-3,5-pyridine dicarboxylate (DHP-27)

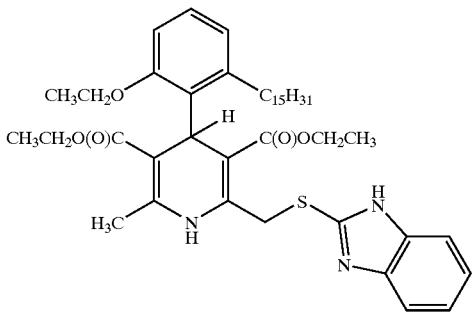

2-Ethoxy-6-pentadecylbenzaldehyde (3 g, 8.3 mmol) and 4-chloro ethyl acetoacetate (1.36 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give diethyl 1,4-dihydro-4-(2'-ethoxy-6'-pentadecylphenyl)-6-methyl-2-chloromethyl-3,5-pyridine dicarboxylate. This compound (0.6 g, 1.2 mmol) was dissolved in dichloromethane (10 mL) and then 2-mercapto-1H-benzimidazole (0.18 g, 1.2 mmol) and NaOH (0.048 g, 1.2 mmol) were charged. Catalytic amount of tetrabutyl ammonium bromide was added and magnetically stirred at room temperature for 2 hrs. The final compound was purified by column chromatography as mentioned in Example 7.

Example 11

Synthesis of ethyl 2-methoxyethyl 1,4-dihydro-4-(2'-ethoxy-6'-pentadecylphenyl)-2,6-dimethyl-3,5 pyridine dicarboxylate (DHP-653)

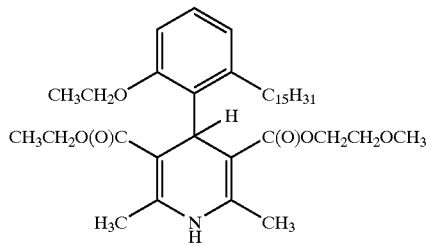

2-Ethoxy-6-pentadecyl benzaldehyde (3 g, 8.3 mmol) and methoxy ethyl acetoacetate (1.32 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give ethyl 2-methoxyethyl1,4-dihydro-4-(2'-ethoxy-6'-pentadecylphenyl)-2,6-dimethyl-3,5 pyridine dicarboxylate.

Example 12

Synthesis of diethyl 1,4-dihydro-4-(2'-(2"methoxy)ethoxy-6'-pentadecylphenyl)-2,6-dimethyl-3,5-pyridine dicarboxylate (DHP-654)

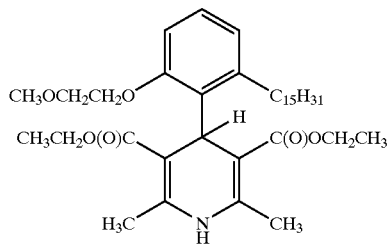

2-(2'-methoxyethoxy)-6-pentadecyl benzaldehyde (3.2 g, 8.3 mmol) and ethyl acetoacetate (1.08 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hex-

Example 13

Synthesis of diethyl 1,4-dihydro-4-(2'-ethoxy-6'-pentadecylphenyl)-2-((2'-amino ethoxy)methyl)-6-methyl-3,5-pyridine dicarboxylate (DHP-84)

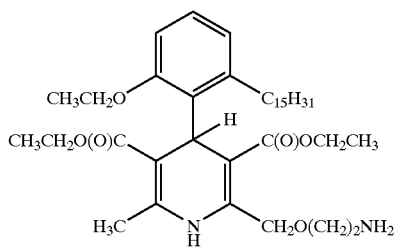

2-Ethoxy-6-pentadecyl benzaldehyde (3 g, 8.3 mmol) and 4-chloro ethyl acetoacetate (1.36 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give diethyl 1,4-dihydro-4-(2'-ethoxy-6'-pentadecylphenyl)-2-chloromethyl-6-methyl-3,5-pyridine dicarboxylate). This compound (0.6. g, 1 mmol) was dissolved in dichloromethane (10 mL) and 2-amino ethanol (0.061 g, 1 mmol) and KOH (0.06 g, 1 mmol) were added and stirred magnetically for 15 min. Then catalytic amount of dibenzo-18-crown-6 and tetrabutyl ammonium bromide was added and stirred for one hour. Then the product was purified by column chromatography as mentioned in example 7.

Example 14

Synthesis of diethyl 1,4-dihydro-4-(2'-ethoxy-3',5'-dinitro-6'-pentadecylphenyl)-2,6-dimethyl-3,5-pyridine dicarboxylate (DHP-132)

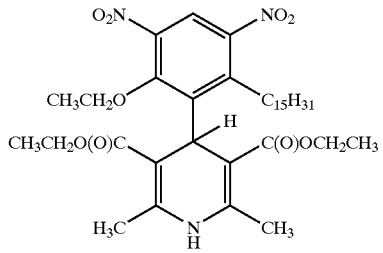

2-Ethoxy-3,5-dinitro-6-pentadecyl benzaldehyde (3.73 g, 8.3 mmol) and ethyl acetoacetate (1.08 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give diethyl 1,4-dihydro-4-(2'-ethoxy-3',5'-dinitro-6'-pentadecylphenyl)-2,6-dimethyl-3,5-pyridine dicarboxylate.

Example 15

Synthesis of diethyl 1,4-dihydro-4-(2'-ethoxy-3'-amino-6'-pentadecylphenyl)-2,6-dimethyl-3,5-pyridine dicarboxylate (DHP-655)

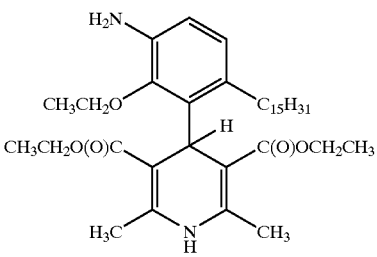

2-Ethoxy-3-acetanilido-6-pentadecyl benzaldehyde (3.46 g, 8.3 mmol) and ethyl acetoacetate (1.08 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was hydrolised and purified by column chromatography using silicagel (100–200 mesh) with hexane:EtOAc (94:6) solvent system to give diethyl 1,4-dihydro-4-(2'-ethoxy-3'-amino-6'-pentadecylphenyl)-2,6-dimethyl-3,5-pyridine.

Example 16

Synthesis of diethyl 1,4-dihydro-4-(2'-ethoxy-6'-pentadecyl phenyl)-6-methyl-2-(5"-methyl-2'-mercapto-1'H-benzimidazolyl)methyl-3,5-pyridine dicarboxylate (DHP-276)

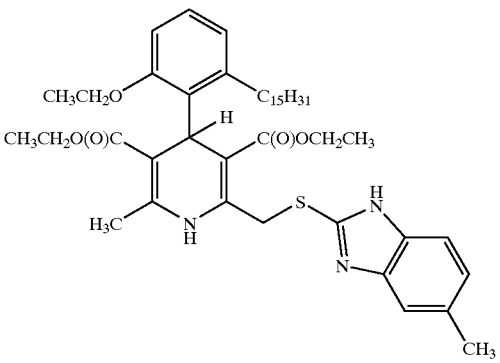

2-Ethoxy-6-pentadecyl benzaldehyde (3 g, 8.3 mmol) and 4-chloro ethyl acetoacetate (1.36 g, 8.3 mmol) were dissolved in n-butanol (20 mL). Acetic acid (0.5 g, 8.3 mmol) and piperidine (0.7 g, 8.3 mmol) were added and stirred at room temperature for 3–4 hrs. Ethyl-3-amino crotonate (1.08 g, 8.3 mmol) was then added and refluxed for 10 hrs. n-Butanol was evaporated and reaction mixture was washed with distilled water and extracted with dichloromethane (10 mL). Organic layer was dried over sodium sulfate, evaporated and compound was purified by column chromatography using silicagel (100–200 mesh) with hexane:EtOAc (94:6) solvent system to give diethyl 1,4-dihydro-4-(2'-ethoxy-6'-pentadecylphenyl)-6-methyl-2-chloromethyl-3,5-pyridine dicarboxylate. This compound (0.6 g, 1 mmol) was dissolved in dichloromethane (10 mL) and then (5'-methyl) 2-mercapto -1H-bezimidazole (0.164 g, 1 mmol) and NaOH (0.04 g, 1 mmol) were charged. Catalytic amount of tetrabutyl ammonium bromide and dibenzo-18-crown-6 were added and magnetically stirred at room temperature for 2 hrs. The final compound was purified by column chromatography as mentioned in Example 7.

Example 17

Aromatization of Hantzsch 1,4-dihydropyridines with $FeCl_3$/Acetic acid

Scheme 13

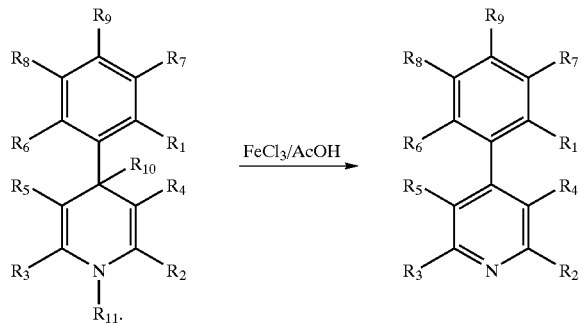

Any of the 1,4-dihydropyridine compounds of the present invention can be converted to the corresponding pyridine compound, as shown in Scheme 13, using the following procedure: A mixture of Hantzsch 1,4-dihydropyridine (10 mmol) and ferric chloride (21 mmol) in acetic acid (30 mL) at room temperature was stirred for an appropriate period (20 minutes to 2 hours). Progress of the reaction was monitored by TLC, and after completion, the reaction was quenched, by pouring it in water (300 mL). The precipitated oil was extracted with ethyl acetate (3×50 mL). Organic layer was separated and was neutralized with $NaHCO_3$ solution (2 M, 2×100 mL) and washed with saturated brine solution (100 mL) and then with distilled water (100 mL). The organic layer was dried over anhydrous sodium sulfate and concentrated to yield pyridine analogue. The resulting crude product was purified by silicagel column chromatography (100–200 mesh, EtOAc/Hexane, 7:3) to afford the corresponding pyridine.

Example 18

Expression of T-Type Channels in Mammalian Cells

T-type calcium channels (α1G) were stably expressed in HEK293 cells and maintained at 37° C. in DMEM. Cells were released from dishes using trypsin and EGTA or Accutase and studied within 4 hours of isolation. Individual cells were placed on the stage of an inverted microscope and patched with pipettes pulled from aluminasilicate glass capillary tubes, which had resistances of 0.8–1.5 Mohm. Currents were recorded using an Axopatch 200 (Axon Instruments, Inc.) and pClamp data acquisition software (8.1). The pipette solution contained (in mM): KCl 130, EGTA 11, HEPES 10, MgATP 5, pH=7.4. The bath solution contained (in mM): NaCl 140, $CaCl_2$ 1, HEPES 10, pH=7.4. Test compounds were diluted into bath solution to the desired concentration (100 nM~10 μM) from a stock solutions (3 or 10 mM in DMSO). Current measurements were made at 20–23° C. Cells were held at −110 mV in order to maximize occupancy in the closed state and depolarized for 100 ms to various potentials. Currents were capacity corrected using 16–64 subthreshold responses (voltage steps of 10 or 20 mV) and leak subtracted, based on linear interpolation between the current at the holding potential and 0 mV. Cells were moved from a control chamber to a chamber with test compound and the effect of the drug was assessed using a voltage clamp protocol that stepped to −30 mV for 100 ms from a holding potential of −110 mV once every 5 s. After each 10–13 minutes, the train protocol was interrupted and a full current voltage relationship obtained. In general for each compound, four cells were studied for a minimum of 13 minutes, two in drug at 500 nM and two at 1 μM. In some cases other concentrations were also studied. Data were analyzed using Matlab (Mathworks, Natick, Mass.). Drug efficacy was estimated using the relationship:

Blocked Fraction=[Drug]/($IC_{50}$+[Drug])

The results are set forth in the table below:

| Compound No. | % of calcium channels blocked | |
| --- | --- | --- |
| | 500 nM of comp'd | 1 μM of comp'd |
| DHP-5 | | 80 |
| DHP-12 | 5 | 77 |
| DHP-338 | 30 | 95 |
| DHP-331 | 80 | |
| Mibefradil | 75 | 90 |
| Nifedipine | 0 | 15 |

References:
Methods of Testing for Pharmacological Activities of the Compounds:
1. Against calcium T-type channels (low voltage activated calcium channels):
   a) L. Lacinova, N. Klugbauer, F. Hofmann "Regulation of the calcium channel $α_{1G}$ subunit by divalent cations and organic blockers" Neuropharmacology, 39, 1254–1266 (2000).
   b) J. P. Clozel, E. A. Ertel, S. I. Ertel "Discovery and main pharmacological properties of mibefradil (Ro 40-5967), the first selective T-type calcium channel blocker" Journal of hypertension 15, S17–S25 (1997).
   c) G. Mehrke, X. G. Zong, V. Flockerzi, F. Hofmann "The $Ca^{2+}$ channel blocker Ro 40-5967 blocks differently T-type and L-type $Ca^{2+}$ channels" Journal of Pharmacology and Experimental Therapeutics, 271, 1483–1488 (1994).
   d) S. Richard, S. Diochot, J. Nargeot, M. Baldy-Moulinier, J. Valmier "Inhibition of T-type calcium currents by dihydropyridines in mouse embryonic dorsal root ganglion neurons" Neuroscience Letters 132, 229–234 (1991).

e) R. S. I. Chaung, H. Jaffe, L. Cribbs, E. Perez-Reyes, K. J. Swartz "Inhibition of T-type voltage gated calcium channel by a new scorpion toxin" Nature Neuroscience, 1, 668–674 (1998).
2. Against calcium L-type channels (high voltage activated calcium channels):
   a) B. Z. Peterson, C. D. DeMaria, D. T. Yue "Calmodulin is the $Ca^{2+}$ sensor for Ca2+-dependent inactivation of L-type calcium channels" Neuron, 22, 549–558 (1999).
   b) G. C. Rovnyak, S. D. Kimball, B. Beyer, G. Cucinotta, J. D. DiMarco, J. Gougoutas, A. Hedberg, M. Malley, J. P. McCarthy, R. Zhang, S. Moreland "Calcium Entry Blockers and Activators: Conformational and Structural Determinants of Dihydropyrimidine Calcium Channel Modulators" Journal of Medicinal Chemistry, 38, 199–129 (1995).
3. Against N-, P/Q-, and R-types of calcium channels:
   a) Stea, A.; Soong, T. W.; Snutch, T. P. "Voltage gated calcium channels," in *Handbook of Receptors and Channels; Ligand- and Voltage-Gated Ion Channels* (North RA ed.), 1995, 113–152, CRC Press Inc., Boca Raton, Fla.
   b) Zamponi, G. W. "Antagonist sites of voltage dependent calcium channels," *Drug Development Research*, 1997, 42, 131–143.
   c) Neelands, T. R.; King, A. P.; Macdonald, R. L. "Functional expression of L-, N-, P/Q-, and R-type calcium channels in the human NT2-N cell line," *J. Neurophysiol.* 2000, 84(6), 393–401.
4. References on 1,4-dihydropyridines:
   a) Goldmann, S.; Stoltefuss, *J. Angew. Chem. Int. Ed. Engl.* 1991, 30, 1559.
   b) Loev, B.; Goodman, M. M.; Snader, K. M.; Tedeschi, R.; Macko, E. *J. Med. Chem.* 1974, 17, 956.

Conclusion

Thus, those of skill in the art will appreciate that the compounds and uses disclosed herein can be used as calcium channel blockers, providing a therapeutic effect.

One skilled in the art will appreciate that these methods and compounds are and may be adapted to carry out the objects and obtain the ends and advantages mentioned, as well as those inherent therein. The methods, procedures, and compounds described herein are presently representative of preferred embodiments and are exemplary and are not intended as limitations on the scope of the invention. Changes therein and other uses will occur to those skilled in the art which are encompassed within the spirit of the invention and are defined by the scope of the claims.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as claimed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.
What is claimed is:
1. A compound of Formula I or II

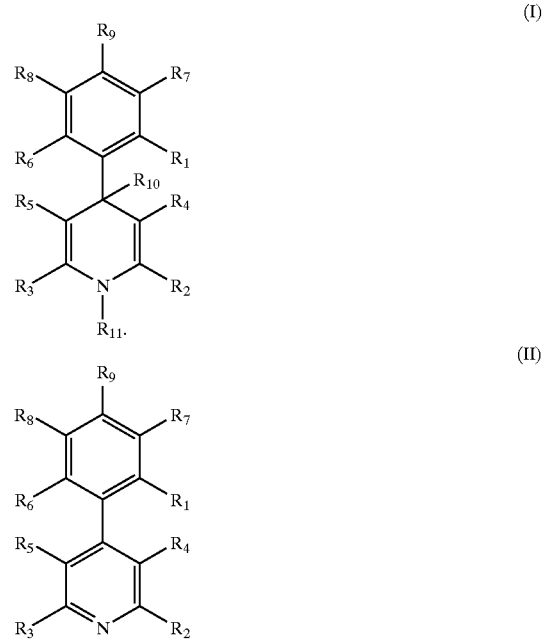

or a pharmaceutically acceptable salt, amide, ester, or prodrug thereof, where
   a) $R_1$ is an straight-chain, branched, or cyclic alkyl group having greater than eight carbon atoms;
   b) $R_2$–$R_9$ are each independently selected from the group consisting of hydrogen, halogen, perhaloalkyl, nitro, amino, a diazo salt, optionally substituted lower alkyl, optionally substituted lower alkylene, optionally substituted lower alkoxy, optionally substituted lower alkoxyalkyl, optionally substituted lower alkoxyalkoxy, optionally substituted lower mercaptyl, optionally substituted lower mercaptoalkyl, optionally substituted lower mercaptomercaptyl, —C(O)OH, —OC(O)H, —C(O)OR, —OC(O)R, —C(S)OR, —OC(S)R, —C(O)SR, —SC(O)R, —C(S)SR, —SC(S)R, C-amido, N-amido, and optionally substituted five- or six-membered heteroaryl ring or optionally substituted six-membered aryl or heteroaryl ring, where the lower alkyl and the lower alkylene moieties are each independently and optionally substituted with one or more substituents selected from the group consisting of halogen, perhaloalkyl, nitro, amino, hydroxy, alkoxy, sulfhydryl, thioether, cyano, amido, ester, and

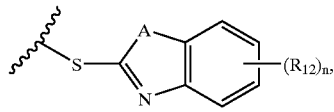

where A is selected from the group consisting of oxygen, sulfur, and —NH and $R_{12}$ is selected for the group consisting of hydrogen, hydroxy, alkoxy, haloalkoxy, halogen, haloalkyl, perhaloalkyl, nitro, amino, and a diazo salt, and n is between 0–4; and where the ring moieties are each independently and optionally substituted with one or more substituents selected from the group consisting of lower alkyl, lower alkylene, c) $R_{10}$ and $R_{11}$ in the compound of Formula I are each independently selected from the group consisting of hydrogen and lower alkyl.

2. The compound of claim 1, wherein $R_1$ is an optionally substituted alkyl group having greater than or equal to ten carbon atoms.

3. The compound of claim 2, wherein $R_1$ has greater than or equal to twelve carbon atoms.

4. The compound of claim 3, wherein $R_1$ has greater than or equal to fifteen carbon atoms.

5. The compound of claim 1, wherein $R_1$ is an optionally substituted $C_{10}$ straight-chain alkyl group.

6. The compound of claim 1, wherein $R_1$ is an optionally substituted $C_{11}$ straight-chain alkyl group.

7. The compound of claim 1, wherein $R_1$ is an optionally substituted $C_{12}$ straight-chain alkyl group.

8. The compound of claim 1, wherein $R_1$ is an optionally substituted $C_{13}$ straight-chain alkyl group.

9. The compound of claim 1, wherein $R_1$ is an optionally substituted $C_{14}$ straight-chain alkyl group.

10. The compound of claim 1, wherein $R_1$ is an optionally substituted $C_{15}$ straight-chain alkyl group.

11. The compound of claim 1, wherein $R_2$ and $R_3$ are each independently an optionally substituted alkyl group.

12. The compound of claim 11, wherein $R_2$ and $R_3$ are the same.

13. The compound of claim 11, wherein $R_2$ and $R_3$ are different.

14. The compound of claim 11, wherein said alkyl is lower alkyl.

15. The compound of claim 11, wherein $R_2$ and $R_3$ are each independently selected from the group consisting of methyl, ethyl, or isopropyl.

16. The compound of claim 11, wherein $R_2$ and $R_3$ are the same and they both are methyl.

17. The compound of claim 1, wherein $R_4$ is

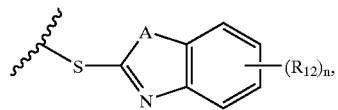

wherein A is selected from the group consisting of oxygen, sulfur, and —NH;

$R_{12}$ is selected from the group consisting of hydrogen, hydroxy, alkoxy, haloalkoxy, halogen, haloalkyl, perhaloalkyl, nitro, amino, and a diazo salt, and n is between 0–4.

18. The compound of claim 17, wherein A is oxygen.

19. The compound of claim 17, wherein A is sulfur.

20. The compound of claim 17, wherein A is —NH.

21. The compound of claim 1, wherein $R_4$ and $R_5$ are each independently selected from the group consisting of a) an optionally substituted alkyl group;

b) an alkoxy of formula —$(X_1)_{n1}$—O—$X_2$, where
   $X_1$ is selected from the group consisting of lower alkylene, lower alkenylene, lower alkynylene, aryl, and heteroaryl;
   $X_2$ is selected from the group consisting of hydrogen, lower alkyl, aryl, and heteroaryl; and
   n1 is 0 or 1; and c) a thioether or thiol of formula —$(X_3)_{n3}$—S—$X_4$, where
   $X_3$ is selected from the group consisting of lower alkylene, lower alkenylene, lower alkynylene, aryl, and heteroaryl;
   $X_4$ is selected from the group consisting of hydrogen, lower alkyl, aryl, and heteroaryl; and
   n3 is 0 or 1;

d) a carboxylic acid of formula —$(X_5)_{n5}$—C(=E)—E'H, where
   $X_5$ is selected from the group consisting of lower alkylene, lower alkenylene, lower alkynylene, aryl, and heteroaryl;
   E and E' are each independently selected from the group consisting of oxygen and sulfur;
   n5 is 0 or 1; and e) an ester of formula —$(X_6)_{n6}$—C(=E)—E'$X_7$, or of formula —$(X_6)_{n6}$—E'—C(=E)—$X_7$, where
   $X_6$ is selected from the group consisting of lower alkylene, lower alkenylene, lower alkynylene, aryl, and heteroaryl;
   E and E' are each independently selected from the group consisting of oxygen and sulfur;
   $X_7$ is selected from the group consisting of hydrogen, lower alkyl, aryl, heteroaryl, hydroxy, alkoxy, amino, and —$NX_8X_9$,
      where $X_8$ and $X_9$ are each independently selected from the group consisting of hydrogen, alkyl, aryl, and heteroaryl; and
   n6 is 0 or 1.

22. The compound of claim 1, wherein $R_4$ and $R_5$ are each independently lower alkyl.

23. The compound of claim 21, wherein $R_4$ and $R_5$ are selected from the group consisting of methyl, ethyl, n-propyl, isopropyl, n-butyl, sec-butyl, and tert-butyl.

24. The compound of claim 21, wherein n1, n3, n5, and n6 are each independently 1, and $X_1$, $X_3$, $X_5$, and $X_6$ are each independently methylene.

25. The compound of claim 21, wherein $X_2$, $X_4$, and $X_7$ are each independently lower alkyl.

26. The compound of claim 25, wherein said lower alkyl is selected from the group consisting of methyl, ethyl, and isopropyl.

27. The compound of claim 21, wherein E and E' are each independently oxygen.

28. The compound of claim 21, wherein E is sulfur and E', if it exists, is oxygen.

29. The compound of claim 21, wherein In certain embodiments, $R_4$ and $R_5$ are each independently selected from the group consisting of —C(O)OH, C(O)OCH$_3$, —C(O)OCH$_2$CH$_3$, —C(O)OCH(CH$_3$)$_2$, —CH$_2$OCH$_3$, —CH$_2$OCH$_2$CH$_3$, and —CH$_2$OCH(CH$_3$)$_2$.

30. The compound of claim 21, wherein $R_4$ and $R_5$ are the same.

31. The compound of claim 21, wherein $R_4$ and $R_5$ are different.

32. The compound of claim 1, wherein $R_6$ is selected from the group consisting of
 a) hydrogen;
 b) an optionally substituted alkyl group;
 c) an alkoxy of formula —(X$_1$)$_{n1}$—O—X$_2$, where
  X$_1$ is selected from the group consisting of lower alkylene, lower alkenylene, lower alkynylene, aryl, and heteroaryl;
  X$_2$ is selected from the group consisting of hydrogen, lower alkyl, aryl, and heteroaryl; and
  n1 is 0 or 1; and
 d) a thioether or thiol of formula —(X$_3$)$_{n3}$—S—X$_4$, where
  X$_3$ is selected from the group consisting of lower alkylene, lower alkenylene, lower alkynylene, aryl, and heteroaryl;
  X$_4$ is selected from the group consisting of hydrogen, lower alkyl, aryl, and heteroaryl; and
  n3 is 0 or 1;
 e) a carboxylic acid of formula —(X$_5$)$_{n5}$—C(=E)—E'H, where
  X$_5$ is selected from the group consisting of lower alkylene, lower alkenylene, lower alkynylene, aryl, and heteroaryl;
  E and E' are each independently selected from the group consisting of oxygen and sulfur;
  n5 is 0 or 1; and
 f) an ester of formula —(X$_6$)$_{n6}$—C(=E)—E'X$_7$, or of formula —(X$_6$)$_{n6}$—E'—C(=E)—X$_7$, where
  X$_6$ is selected from the group consisting of lower alkylene, lower alkenylene, lower alkynylene, aryl, and heteroaryl;
  E and E' are each independently selected from the group consisting of oxygen and sulfur;
  X$_7$ is selected from the group consisting of hydrogen, lower alkyl, aryl, heteroaryl, hydroxy, alkoxy, amino, and —NX$_8$X$_9$,
   where X$_8$ and X$_9$ are each independently selected from the group consisting of hydrogen, alkyl, aryl, and heteroaryl; and
  n6 is 0 or 1.

33. The compound of claim 32, wherein said alkyl is a lower alkyl.

34. The compound of claim 33, wherein said lower alkyl is selected from the group consisting of methyl, ethyl, and isopropyl.

35. The compound of claim 32, wherein $R_6$ is an alkoxy selected from the group consisting of methoxy, ethoxy, and isopropoxy.

36. The compound of claim 1, wherein $R_7$–$R_9$ are each independently selected from the group consisting of
 a) hydrogen;
 b) an optionally substituted alkyl group;
 c) an alkoxy of formula —(X$_1$)$_{n1}$—O—X$_2$, where
  X$_1$ is selected from the group consisting of lower alkylene, lower alkenylene, lower alkynylene, aryl, and heteroaryl;
  X$_2$ is selected from the group consisting of hydrogen, lower alkyl, aryl, and heteroaryl; and
  n1 is 0 or 1; and
 d) a thioether or thiol of formula —(X$_3$)$_{n3}$—S—X$_4$, where
  X$_3$ is selected from the group consisting of lower alkylene, lower alkenylene, lower alkynylene, aryl, and heteroaryl;
  X$_4$ is selected from the group consisting of hydrogen, lower alkyl, aryl, and heteroaryl; and
  n3 is 0 or 1;
 e) a carboxylic acid of formula —(X$_5$)$_{n5}$—C(=E)—E'H, where
  X$_5$ is selected from the group consisting of lower alkylene, lower alkenylene, lower alkynylene, aryl, and heteroaryl,
  E and E' are each independently selected from the group consisting of oxygen and sulfur;
  n5 is 0 or 1;
 f) an ester of formula —(X$_6$)$_{n6}$—C(=E)—E'X$_7$, or of formula —(X$_6$)$_{n6}$—E'—C(=E)—X$_7$, where
  X$_6$ is selected from the group consisting of lower alkylene, lower alkenylene, lower alkynylene, aryl, and heteroaryl;
  E and E' are each independently selected from the group consisting of oxygen and sulfur;
  X$_7$ is selected from the group consisting of hydrogen, lower alkyl, aryl, heteroaryl, hydroxy, alkoxy, amino, and —NX$_8$X$_9$,
   where X$_8$ and X$_9$ are each independently selected from the group consisting of hydrogen, alkyl, aryl, and heteroaryl; and
  n6 is 0 or 1;
 g) an amine of formula —(X$_{10}$)$_{n10}$—NX$_{11}$X$_{12}$, where
  X$_{10}$ is selected from the group consisting of lower alkylene, lower alkenylene, lower alkynylene, aryl, and heteroaryl;
  where X$_{10}$ and X$_{11}$ are each independently selected from the group consisting of hydrogen, alkyl, aryl, and heteroaryl; and
  n$_{10}$ is 0 or 1;
 h) NO$_2$;
 i) halogen or perhaloalkyl; and
 j) CN.

37. The compound of claim 36, wherein said alkyl is a lower alkyl.

38. The compound of claim 37, wherein said lower alkyl is selected from the group consisting of methyl, ethyl, and isopropyl.

39. The compound of claim 36, wherein $R_7$–$R_9$ are each independently selected from the group consisting of hydrogen, hydroxy, cyano (CN), nitro (NO$_2$), amino (NH$_2$), methyl, ethyl, isopropyl, fluoro, and chloro.

40. The compound of claim 36, wherein $R_7$–$R_9$ are the same.

41. The compound of claim 36, wherein $R_7$–$R_9$ are different.

42. The compound of claim 1, wherein $R_{10}$ and $R_{11}$ are each independently selected from the group consisting of hydrogen and alkyl.

43. The compound of claim 42, wherein said alkyl is a lower alkyl.

44. The compound of claim 43, wherein said lower alkyl is selected from the group consisting of methyl, ethyl, and isopropyl.

45. The compound of claim 42, wherein $R_{10}$ and $R_{11}$ are each hydrogen.

46. A compound selected from the group consisting of diethyl 1,4-dihydro-4-(2'-ethoxy-6'-pentadecylphenyl)-2,6-dimethyl-3,5-pyridine dicarboxylate, dimethyl 1,4-dihydro-4-(2'-ethoxy-6'-pentadecylphenyl)-2,6-dimethyl-3,5-pyridine dicarboxylate, diisopropyl 1,4-dihydro-4-(2'-ethoxy-6'-pentadecylphenyl)-2,6-dimethyl-3,5-pyridine dicarboxylate, diethyl 1,4-dihydro-4-(2'-methoxy-6'-pentadecylphenyl)-2,6-dimethyl-3,5-pyridine dicarboxylate, dimethyl 1,4-dihydro-4-(2'-methoxy-6'-pentadecylphenyl)-2,6-dimethyl-3,5-pyridine dicarboxylate, diisopropyl 1,4-dihydro-4-(2'-methoxy-6'-pentadecylphenyl)-2,6-dimethyl-3,5-carbon pyridine dicarboxylate, diethyl 1,4-dihydro-4-(2'-isopropoxy-6'-pentadecylphenyl)-2,6-dimethyl-3,5-pyridine dicarboxylate, dimethyl 1,4-dihydro-4-(2'-isopropoxy-6'-pentadecylphenyl)-2,6-dimethyl-3,5-pyridine dicarboxylate, diisopropyl 1,4-dihydro-4-(2'-isopropoxy-6'-pentadecylphenyl)-2,6-dimethyl-3,5-pyridine dicarboxylate, diethyl 1,4-dihydro-4-(2'-methoxy-6'-pentadecylphenyl)-2-methyl-6-(2'-mercapto-1'H-benzimidazolyl) methyl-3,5-pyridine dicarboxylate, dimethyl 1,4-dihydro-4-(2'-methoxy-6'-pentadecylphenyl)-2-methyl-6-(2'-mercapto-1'H-benzimidazolyl)methyl-3,5-pyridine dicarboxylate, diisopropyl 1,4-dihydro-4-(2'-methoxy-6'-pentadecylphenyl)-2-methyl-6-(2'-mercapto-1'H-benzimidazolyl)methyl-3,5-pyridine dicarboxylate, diethyl 1,4-dihydro-4-(2'-isopropoxy-6'-pentadecylphenyl)-2-methyl-6-(2'-mercapto-1'H-benzimidazolyl)methyl-3,5-pyridine dicarboxylate, dimethyl 1,4-dihydro-4-(2'-isopropoxy-6'-pentadecylphenyl)-2-methyl-6-(2'-mercapto-1'H-benzimidazolyl)methyl-3,5-pyridine dicarboxylate, diisopropyl 1,4-dihydro-4-(2'-isopropoxy-6'-pentadecylphenyl)-2-methyl-6-(2'-mercapto-1'H-benzimidazolyl)methyl-3,5-pyridine dicarboxylate, diethyl 1,4-dihydro-4-(2'-ethoxy-6'-pentadecylphenyl)-2-methyl-6-(2'-mercapto-1'H-benzimidazolyl)methyl-3,5-pyridine dicarboxylate, dimethyl 1,4-dihydro-4-(2'-ethoxy-6'-pentadecylphenyl)-2-methyl-6-(2'-mercapto-1'H-benzimidazolyl)methyl-3,5-pyridine dicarboxylate, diisopropyl 1,4-dihydro-4-(2'-ethoxy-6'-pentadecylphenyl)-2-methyl-6-(2'-mercapto-1'H-benzimidazolyl)methyl-3,5-pyridine dicarboxylate, 1,4-dihydro-4-(2'-ethoxy-6'-pentadecylphenyl)-2,6-dimethyl-3-ethyl-5-(methoxy ethyl)pyridin dicarboxylate, 1,4-dihydro-4-(2'-ethoxy-6'-pentadecylphenyl)-2,6-dimethyl-3-methyl-5-(methoxy ethyl)pyridine dicarboxylate, 1,4-dihydro-4-(2'-ethoxy-6'-pentadecylphenyl)-2,6-dimethyl-3-isopropyl-5-(methoxy ethyl)pyridine dicarboxylate, 1,4-dihydro-4-(2'-methoxy-6'-pentadecylphenyl)-2,6-dimethyl-3-ethyl-5-(methoxy ethyl)pyridine dicarboxylate, 1,4-dihydro-4-(2'-isopropoxy-6'-pentadecylphenyl)-2,6-dimethyl-3-ethyl-5-(methoxy ethyl)pyridine dicarboxylate, diethyl 1,4-dihydro-4-(2'-ethoxy-6'-pentadecylphenyl)-2-(2'-amino ethoxy)methyl-6-methyl-3,5-pyridine dicarboxylate, dimethyl 1,4-dihydro-4-(2'-ethoxy-6'-pentadecylphenyl)-2-(2'-amino ethoxy)methyl-6-methyl-3,5-pyridine dicarboxylate, diisopropyl 1,4-dihydro-4-(2'-ethoxy-6'-pentadecylphenyl)-2-(2'-amino ethoxy)methyl-6-methyl-3,5-pyridine dicarboxylate, diethyl 1,4-dihydro-4-(2'-methoxy-6'-pentadecylphenyl)-2-(2'-amino ethoxy)methyl-6-methyl-3,5-pyridine dicarboxylate, dimethyl 1,4-dihydro-4-(2'-methoxy-6'-pentadecylphenyl)-2-(2'-amino ethoxy)methyl-6-methyl-3,5-pyridine dicarboxylate, diisopropyl 1,4-dihydro-4-(2'-methoxy-6'-pentadecylphenyl)-2-(2'-amino ethoxy)methyl-6-methyl-3,5-pyridine dicarboxylate, diethyl 1,4-dihydro-4-(2'-isopropoxy-6'-pentadecylphenyl)-2-((2'-amino ethoxy) methyl-6-methyl-3,5-pyridine dicarboxylate, dimethyl 1,4-dihydro-4-(2'-isopropoxy-6'-pentadecylphenyl)-2-(2'-amino ethoxy)methyl-6-methyl-3,5-pyridine dicarboxylate, diisopropyl 1,4-dihydro-4-(2'-isopropoxy-6'-pentadecylphenyl)-2-(2'-amino ethoxy) methyl-6-methyl-3,5-pyridine dicarboxylate, diethyl 1,4-dihydro-4-(2'-ethoxy-3',5'-dinitro-6'-pentadecylphenyl)-2,6-dimethyl-3,5-pyridine dicarboxylate, dimethyl 1,4-dihydro-4-(2'-ethoxy-3',5'-dinitro-6'-pentadecylphenyl)-2,6-dimethyl-3,5-pyridine dicarboxylate, diisopropyl 1,4-dihydro-4-(2'-ethoxy-3',5'-dinitro-6'-pentadecylphenyl)-2,6-dimethyl-3,5-pyridine dicarboxylate, diethyl 1,4-dihydro-4-(2'-methoxy-3',5'-dinitro-6'-pentadecylphenyl)-2,6-dimethyl-3,5-pyridine dicarboxylate, dimethyl 1,4-dihydro-4-(2'-methoxy-3',5'-dinitro-6'-pentadecylphenyl)-2,6-dimethyl-3,5-pyridine dicarboxylate, diisopropyl 1,4-dihydro-4-(2'-methoxy-3',5'-dinitro-6'-pentadecylphenyl)-2,6-dimethyl-3,5-pyridine dicarboxylate, diethyl 1,4-dihydro-4-(2'-isopropoxy-3',5'-dinitro-6'-pentadecylphenyl)-2,6-dimethyl-3,5-pyridine dicarboxylate, dimethyl 1,4-dihydro-4-(2'-isopropoxy-3',5'-dinitro-6'-pentadecylphenyl)-2,6-dimethyl-3,5-pyridine dicarboxylate, diisopropyl 1,4-dihydro-4-(2'-isopropoxy-3',5'-dinitro-6'-pentadecylphenyl)-2,6-dimethyl-3,5-pyridine dicarboxylate, diethyl 1,4-dihydro-4-(2'-ethoxy-3',5'-diamino-6'-pentadecylphenyl)-2,6-dimethyl-3,5-pyridine dicarboxylate, dimethyl 1,4-dihydro-4-(2'-ethoxy-3',5'-diamino-6'-pentadecylphenyl)-2,6-dimethyl-3,5-pyridine dicarboxylate, diisopropyl 1,4-dihydro-4-(2'-ethoxy-3',5'-diamino-6'-pentadecylphenyl)-2,6-dimethyl-3,5-pyridine dicarboxylate, diethyl 1,4-dihydro-4-(2'-methoxy-3',5'-diamino-6'-pentadecylphenyl)-2,6-dimethyl-3,5-pyridine dicarboxylate, dimethyl 1,4-dihydro-4-(2'-methoxy-3',5'-diamino-6'-pentadecylphenyl)-2,6-dimethyl-3,5-pyridine dicarboxylate, diisopropyl 1,4-dihydro-4-(2'-methoxy-3',5'-diamino-6'-pentadecylphenyl)-2,6-dimethyl-3,5-pyridine dicarboxylate, diethyl 1,4-dihydro-4-(2'-isopropoxy-3',5'-diamino-6'-pentadecylphenyl)-2,6-dimethyl-3,5-pyridine dicarboxylate, dimethyl 1,4-dihydro-4-(2'-isopropoxy-3',5'-diamino-6'-pentadecylphenyl)-2,6-dimethyl-3,5-pyridine dicarboxylate, diisopropyl 1,4-dihydro-4-(2'-isopropoxy-3',5'-diamino-6'-pentadecylphenyl)-2,6-dimethyl-3,5-pyridine dicarboxylate, diethyl 1,4-dihydro-4-(2'-ethoxy-6'-pentadecylphenyl)-2-methyl-6-(5"-methyl-2-mercapto-1'H-benzimidazolyl)methyl-3,5-pyridine dicarboxylate, dimethyl 1,4-dihydro-4-(2'-ethoxy-6'-pentadecylphenyl)-2-methyl-6-(5"-methyl-2-mercapto-1'H-benzimidazolyl)methyl-3,5-pyridine dicarboxylate, diisopropyl 1,4-dihydro-4-(2'-ethoxy-6'-pentadecylphenyl)-2-methyl-6-(5"-methyl-2-mercapto-1'H-benzimidazolyl)methyl-3,5-pyridine dicarboxylate, diethyl 1,4-dihydro-4-(2'-methoxy-6'-pentadecylphenyl)-2-methyl-6-(5"-methyl-2-mercapto-1'H-benzimidazolyl)methyl-3,5-pyridine dicarboxylate, dimethyl 1,4-dihydro-4-(2'-methoxy-6'-pentadecylphenyl)-2-methyl-6-(5"-methyl-2-mercapto-1'H-benzimidazolyl)methyl-3,5-pyridine dicarboxylate, diisopropyl 1,4-dihydro-4-(2'-methoxy-6'-pentadecylphenyl)-2-methyl-6-(5"-methyl-2-mercapto-1'H-benzimidazolyl)methyl-3,5-pyridine dicarboxylate, diethyl 1,4-dihydro-4-(2'-isopropoxy-6'-pentadecylphenyl)-2-methyl-6-(5"-methyl-2-mercapto-1'H-benzimidazolyl)methyl-3,5-pyridine dicarboxylate, dimethyl 1,4-dihydro-4-(2'-isopropoxy-6'-pentadecylphenyl)-2-methyl-6-methyl (5'-methyl-2-mercapto-1'H-benzimidazolyl)methyl-3,5-pyridine dicarboxylate, and diisopropyl 1,4-dihydro-4-(2'-isopropoxy-6'-pentadecylphenyl)-2-methyl-6-methyl (5'-methyl-2-mercapto-1'H-benzimidazolyl)methyl-3,5-pyridine dicarboxylate.

47. A compound selected from the group consisting of DHP-1 through DHP-655, DHP-1-11 through DHP-326-11, DHP-653-11 through DHP-655-11, DHP-1-12 through DHP-326-12, DHP-653-12 through DHP-655-12, DHP-1-13 through DHP-326-13, DHP-653-13 through DHP-655-13, DHP-1-14 through DHP-326-14, and DHP-653-14 through DHP-655-14.

48. A method of antagonizing the activity of a calcium channel in a cell comprising the step of contacting said cell with a compound of claim 1.

49. The method of claim 48, wherein said calcium channel is a low voltage activated calcium channel or a high voltage activated calcium channel.

50. A method of treating a disease associated with a cellular calcium channel comprising:
   a) identifying a subject in need of such treatment;
   b) administering to said subject a effective calcium-channel antagonizing amount of a compound of claim 1, wherein said disease is a cardiovascular disease or a neurological disorder.

51. The method of claim 50, wherein said subject is a mammal.

52. The method of claim 51, wherein said subject is a human.

53. A pharmaceutical composition comprising a compound of claim 1, and a physiologically acceptable carrier, diluent, or excipient, or a combination thereof.

* * * * *